United States Patent
Drasler et al.

(10) Patent No.: US 11,826,089 B2
(45) Date of Patent: Nov. 28, 2023

(54) COMPRESSION STENT DEVICE AND METHODS

(71) Applicants: William Joseph Drasler, Minnetonka, MN (US); William Joseph Drasler, II, Minnetonka, MN (US)

(72) Inventors: William Joseph Drasler, Minnetonka, MN (US); William Joseph Drasler, II, Minnetonka, MN (US)

( * ) Notice: Subject to any disclaimer, the term of this patent is extended or adjusted under 35 U.S.C. 154(b) by 288 days.

(21) Appl. No.: 17/336,520

(22) Filed: Jun. 2, 2021

(65) Prior Publication Data

US 2021/0290294 A1 Sep. 23, 2021

Related U.S. Application Data

(63) Continuation of application No. 16/002,144, filed on Jun. 7, 2018, now Pat. No. 11,051,870.

(60) Provisional application No. 62/620,634, filed on Jan. 23, 2018, provisional application No. 62/608,007, filed on Dec. 20, 2017, provisional application No. 62/604,784, filed on Jul. 20, 2017.

(51) Int. Cl.
| | |
|---|---|
| *A61B 18/14* | (2006.01) |
| *A61F 2/82* | (2013.01) |
| *A61B 18/00* | (2006.01) |
| *A61M 29/02* | (2006.01) |
| *A61B 18/12* | (2006.01) |
| *A61F 2/958* | (2013.01) |

(52) U.S. Cl.
CPC ............... *A61B 18/14* (2013.01); *A61F 2/82* (2013.01); *A61B 2018/00267* (2013.01); *A61B 2018/00404* (2013.01); *A61B 2018/00434* (2013.01); *A61B 2018/00511* (2013.01); *A61B 2018/00577* (2013.01); *A61B 2018/126* (2013.01); *A61B 2018/1253* (2013.01); *A61B 2018/1467* (2013.01); *A61F 2/958* (2013.01); *A61M 29/02* (2013.01)

(58) Field of Classification Search
CPC .......... A61B 18/14; A61B 2018/00267; A61B 2018/00404; A61B 2018/00434; A61B 2018/00511; A61B 2018/00577; A61B 2018/1253; A61B 2018/126; A61B 2018/1467; A61F 2/82; A61F 2/958; A61M 29/02

See application file for complete search history.

(56) References Cited

U.S. PATENT DOCUMENTS

| | | | | |
|---|---|---|---|---|
| 6,442,413 | B1 * | 8/2002 | Silver ................ | A61B 5/14865 600/347 |
| 2003/0028211 | A1 * | 2/2003 | Crocker ............ | A61M 25/1027 606/192 |
| 2015/0173923 | A1 * | 6/2015 | Mayberry ............... | A61F 2/954 623/1.11 |
| 2015/0351836 | A1 * | 12/2015 | Prutchi .............. | A61B 18/1492 606/41 |

(Continued)

*Primary Examiner* — Jaymi E Della
*Assistant Examiner* — Rachel A. Vierra

(57) ABSTRACT

A device and method for compressing a renal artery prior to delivery of radiofrequency ablative energy to the renal nerves. The device includes a stent structure with a focal region that expands outwards to place the RF electrodes located on the stent structure in close proximity to the renal nerves. A covering is applied to the stent structure to prevent intimal hyperplasia.

20 Claims, 42 Drawing Sheets

(56) References Cited

U.S. PATENT DOCUMENTS

2017/0368330 A1* 12/2017 Silay .................. A61N 1/36139

* cited by examiner

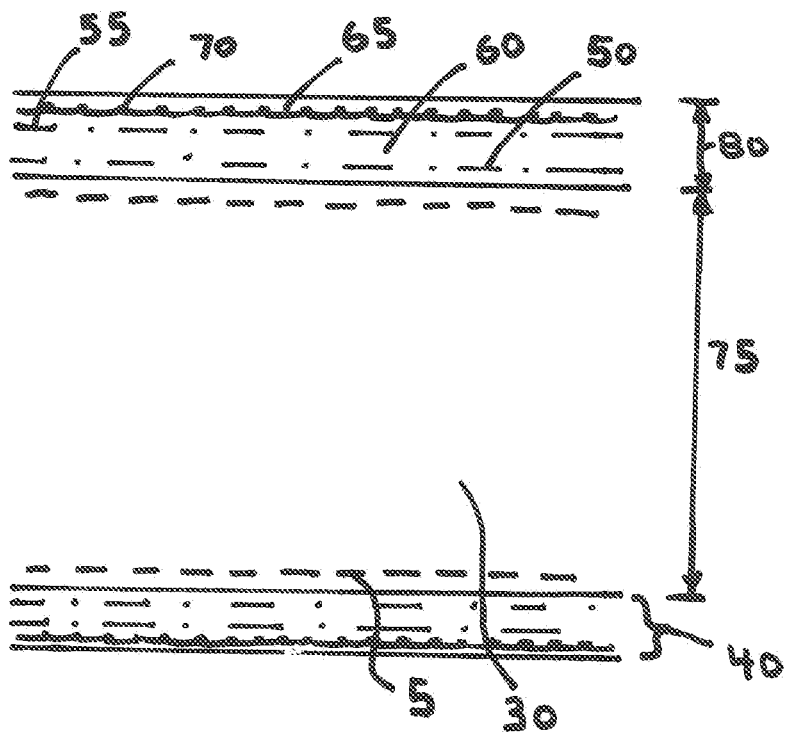
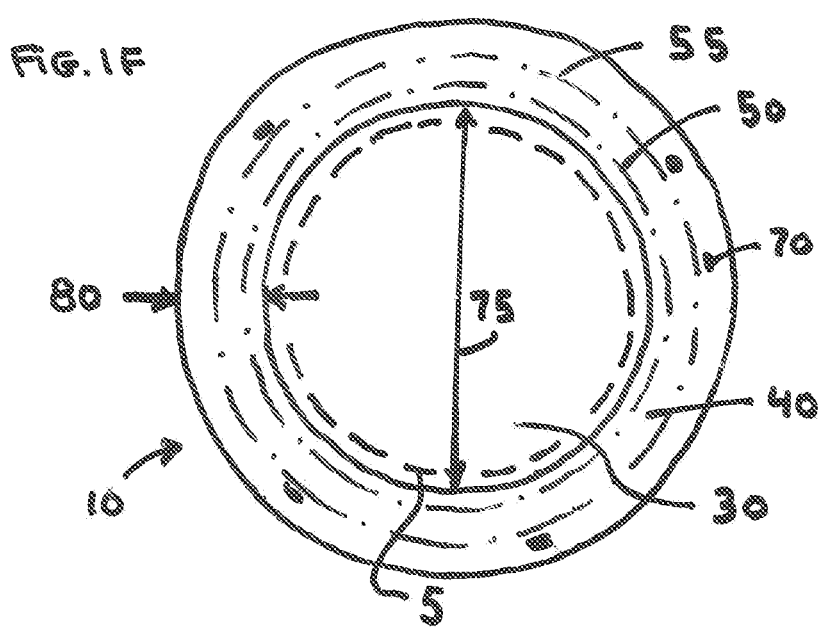

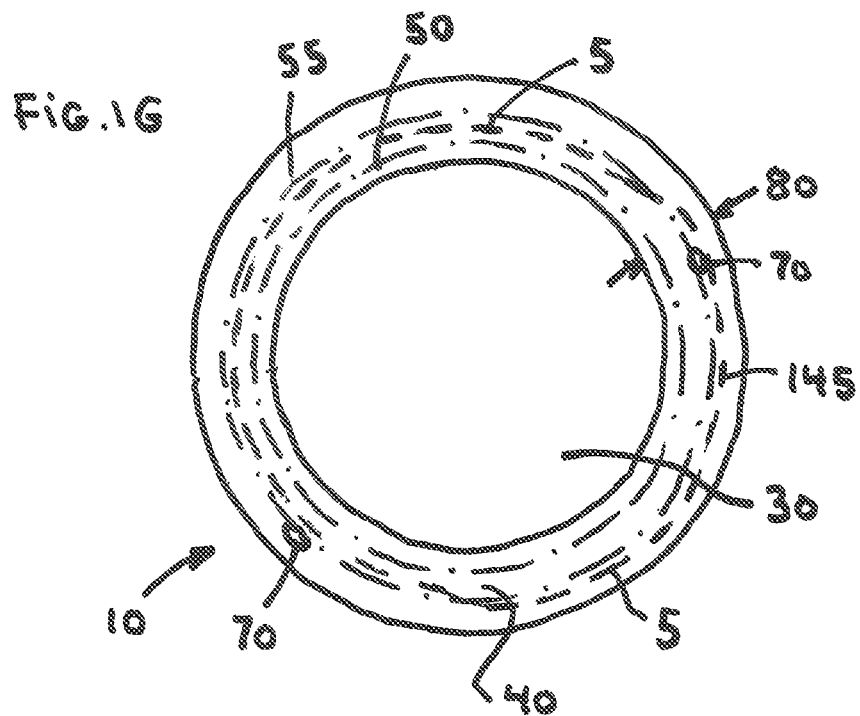

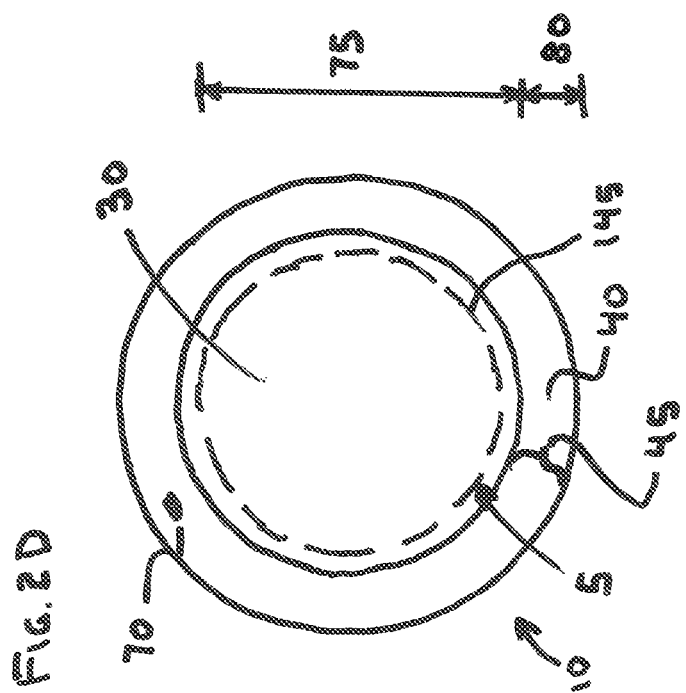
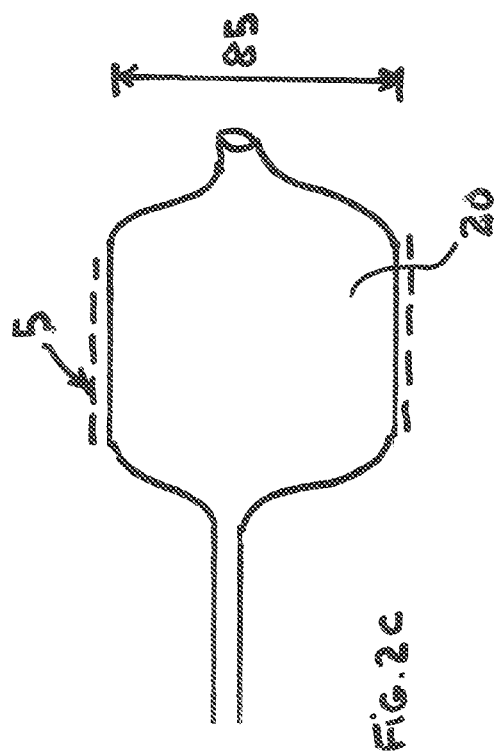

FIG. 3
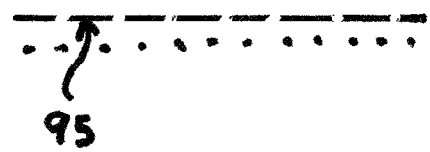
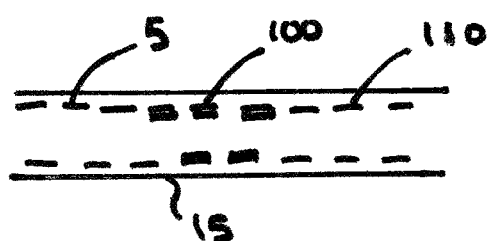
FIG. 4A
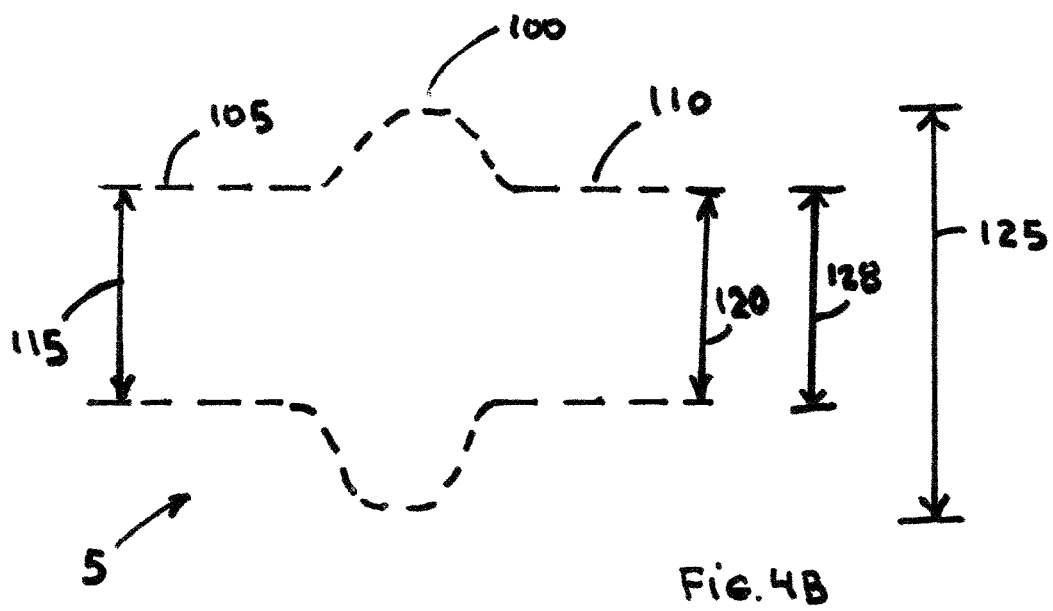
FIG. 4B

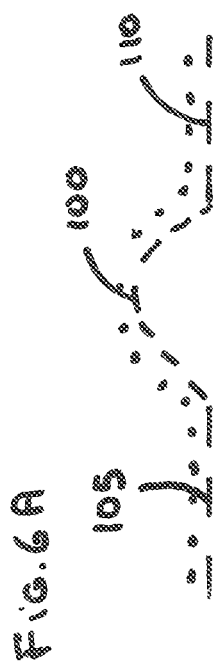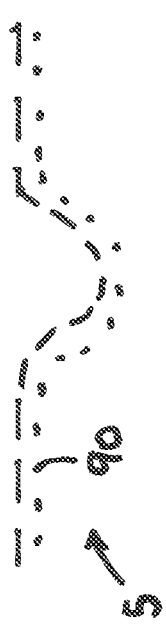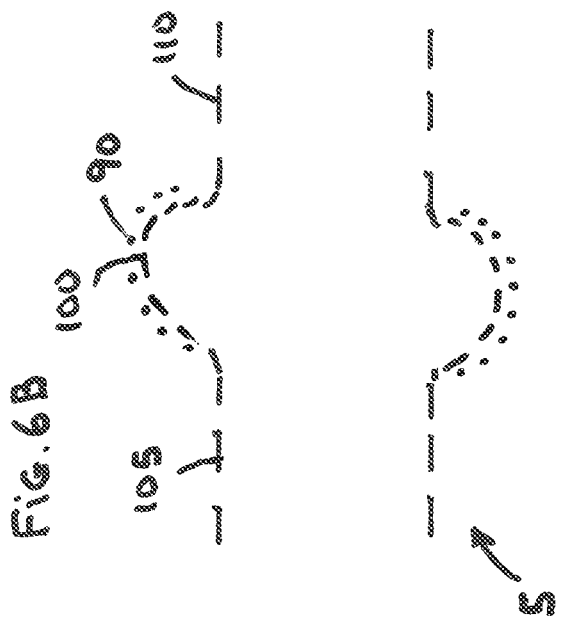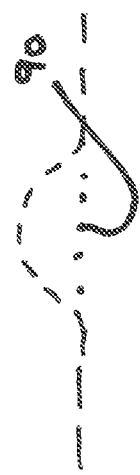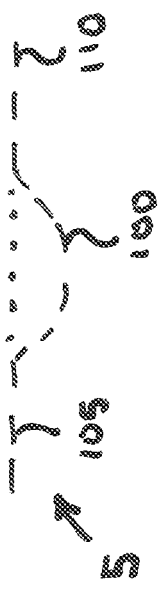
Fig. 6A, Fig. 6B, Fig. 6C

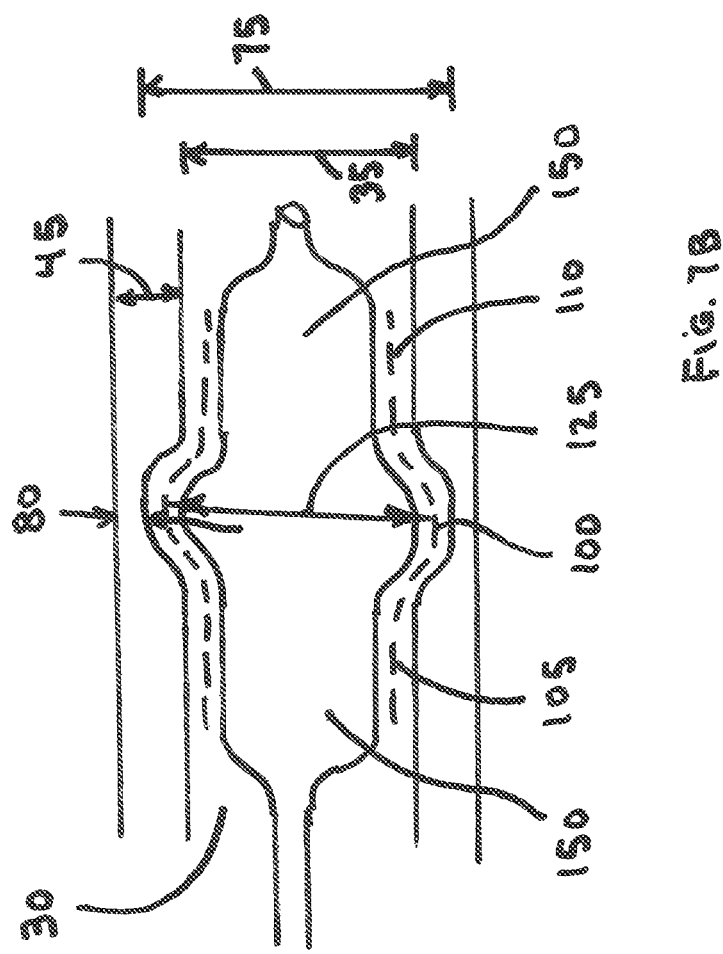

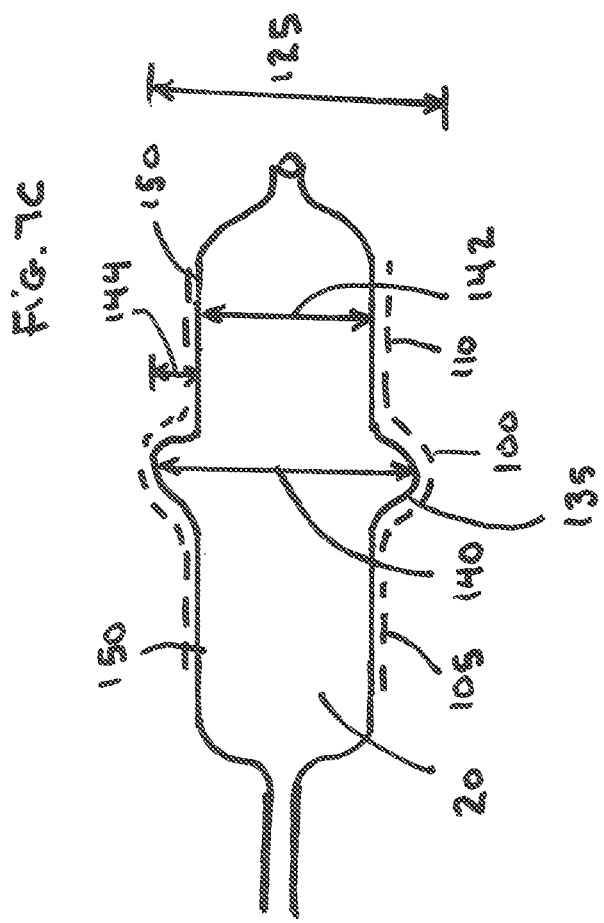

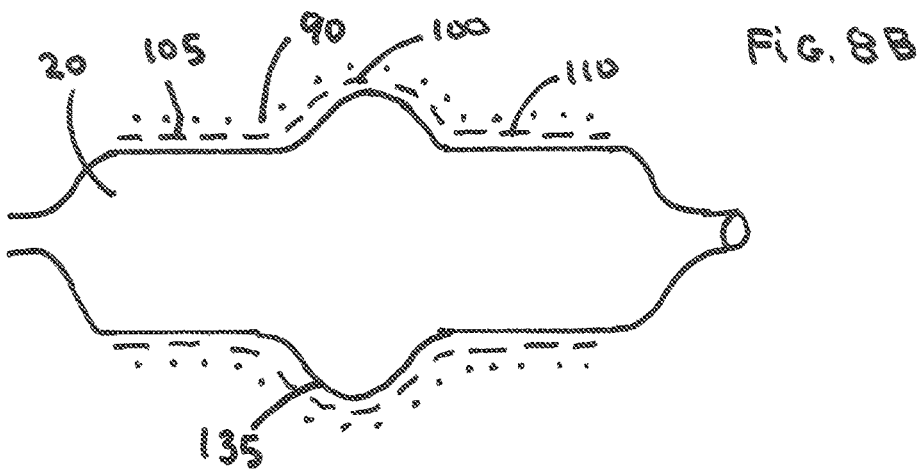
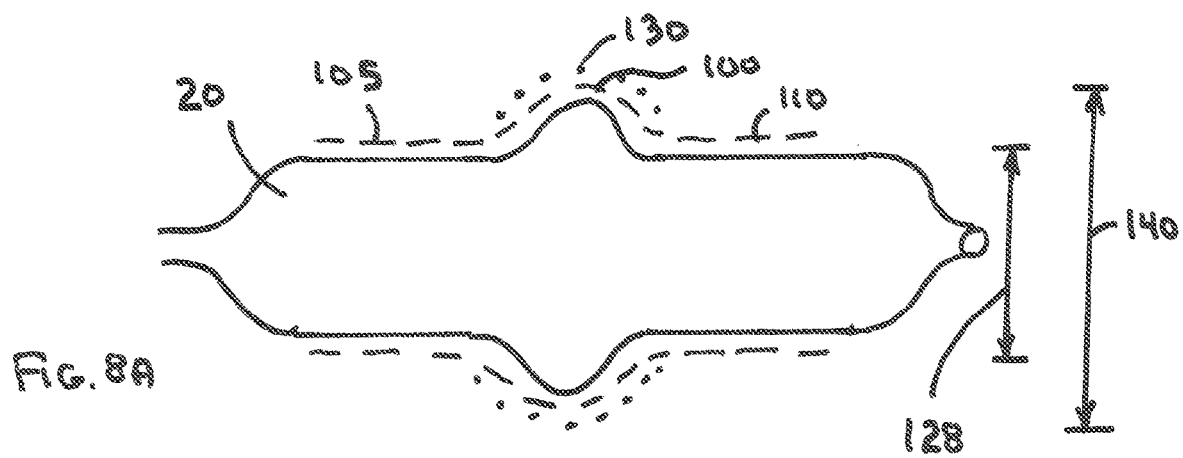
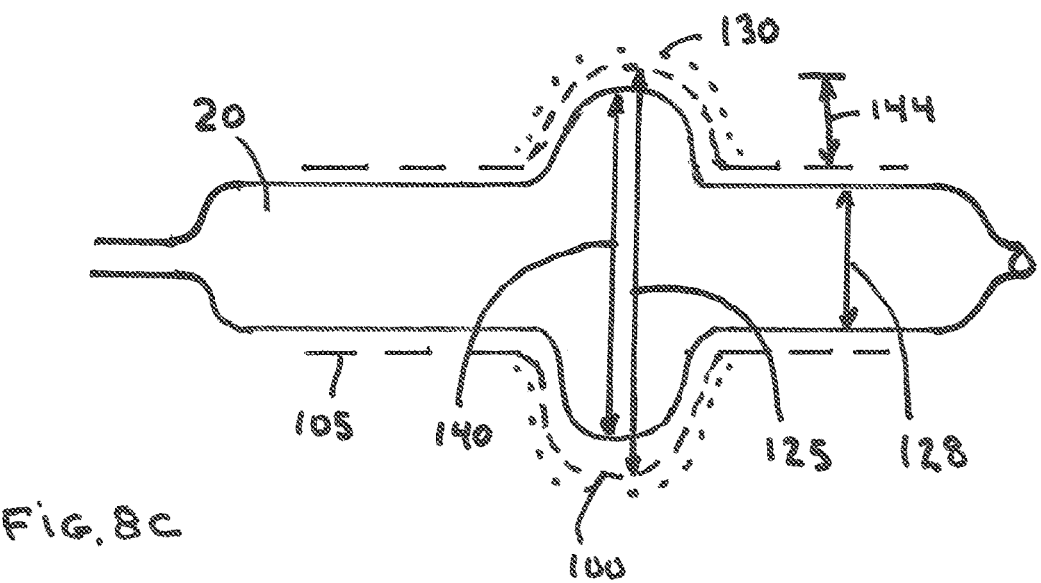

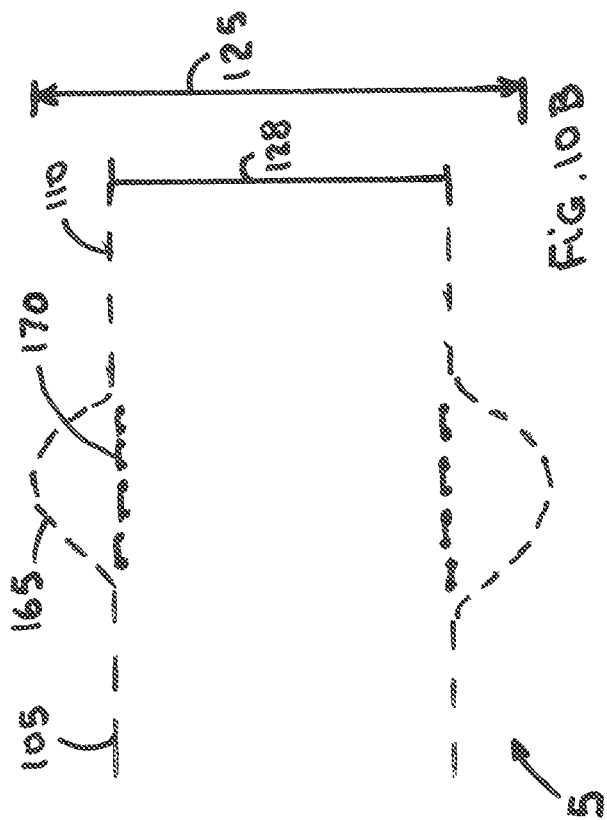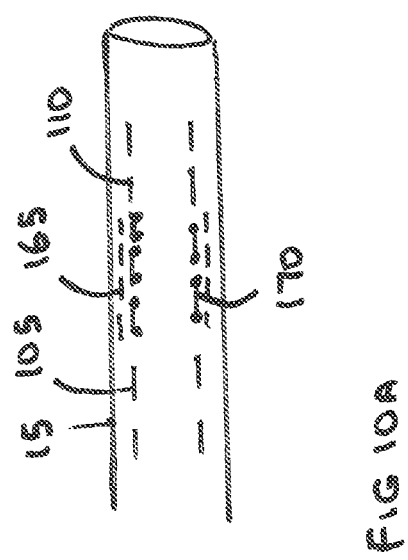

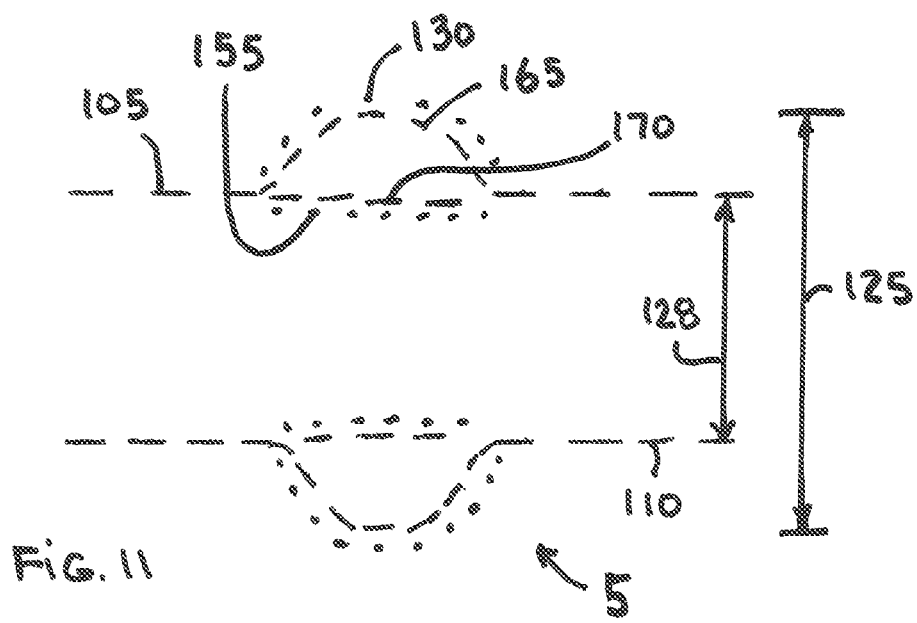

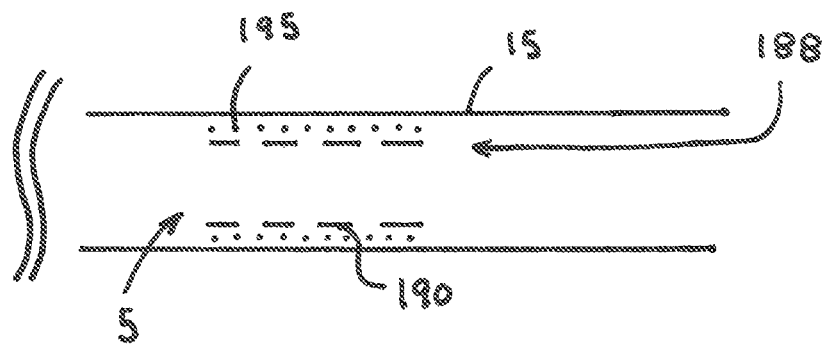
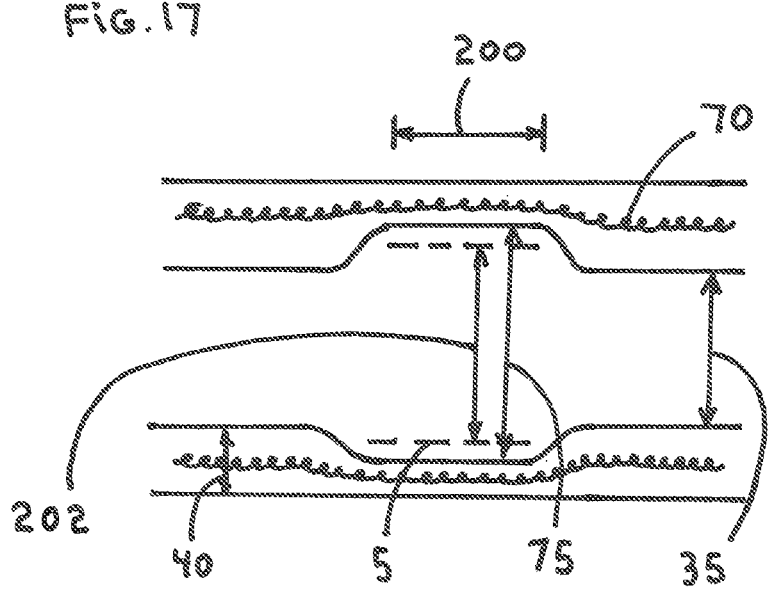

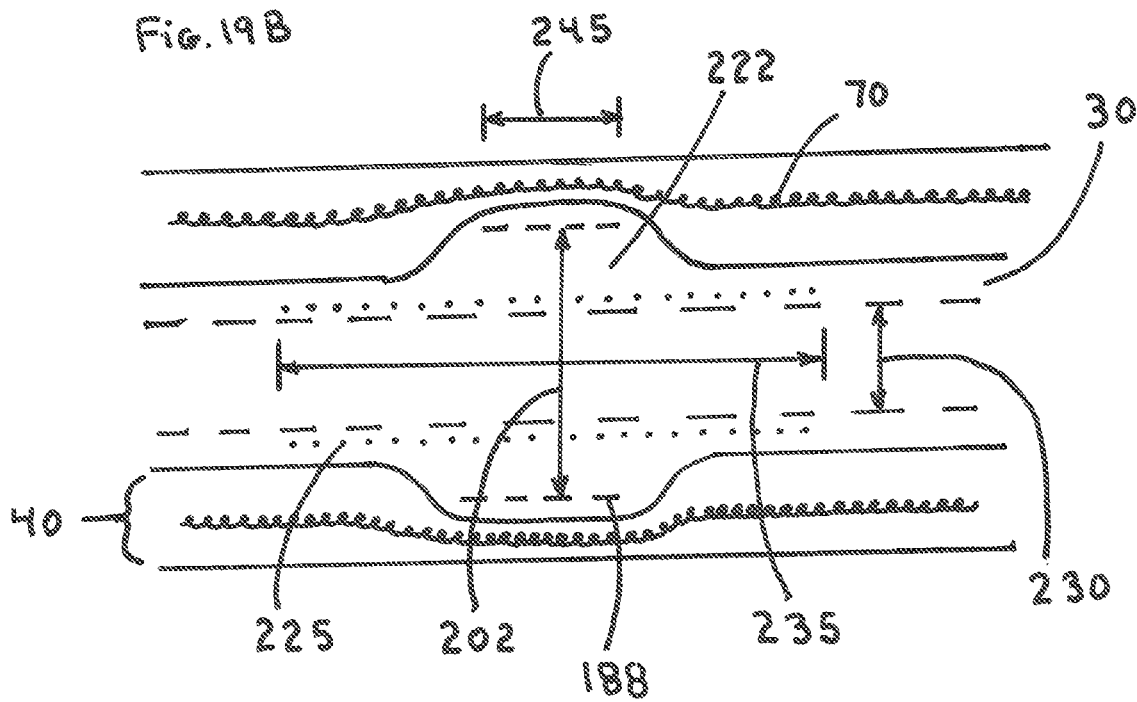
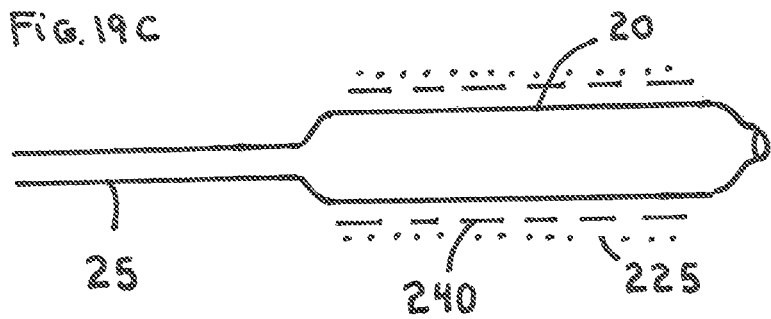

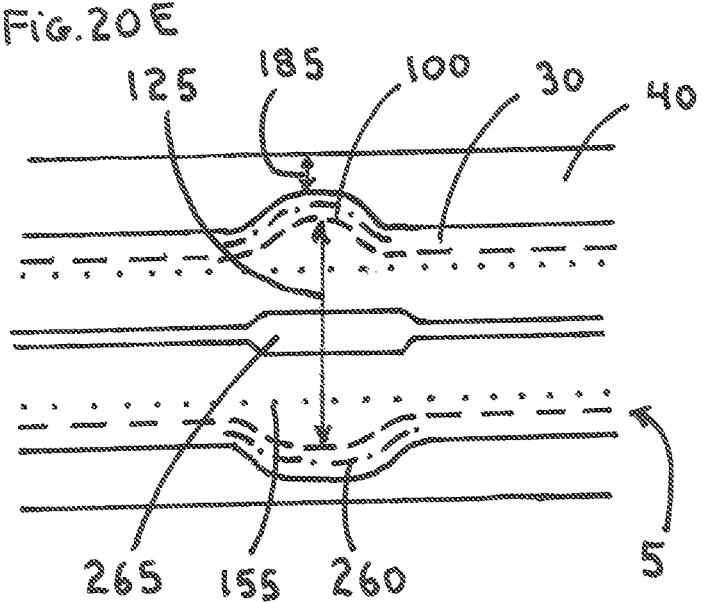

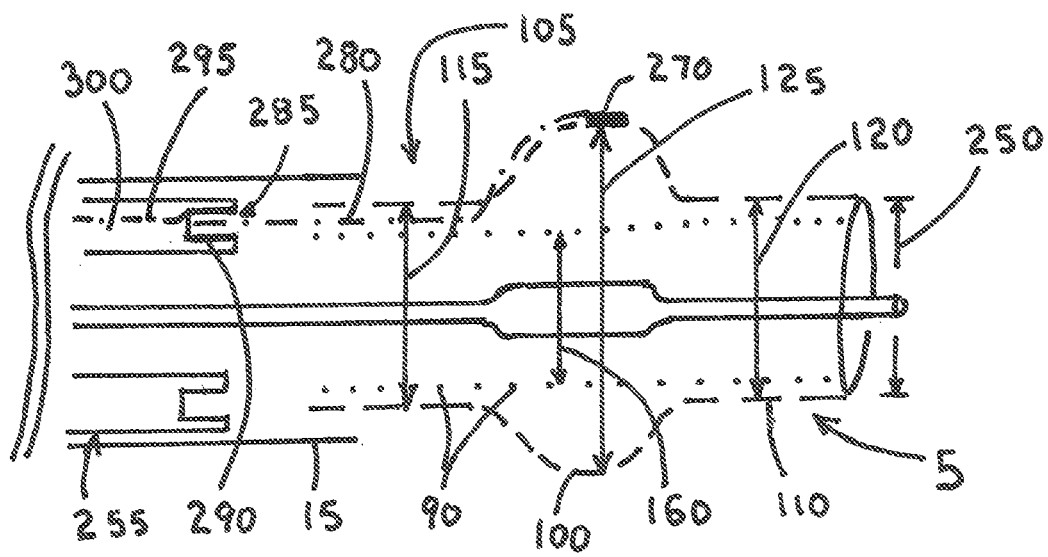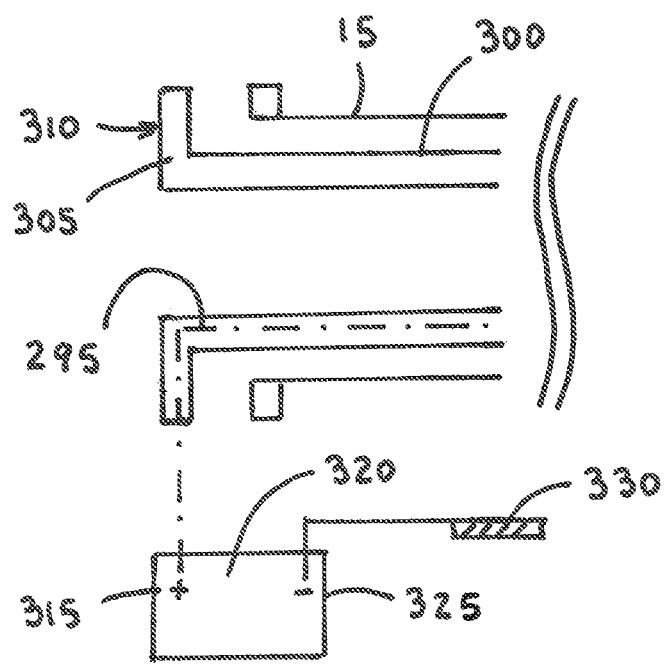
Fig. 21A

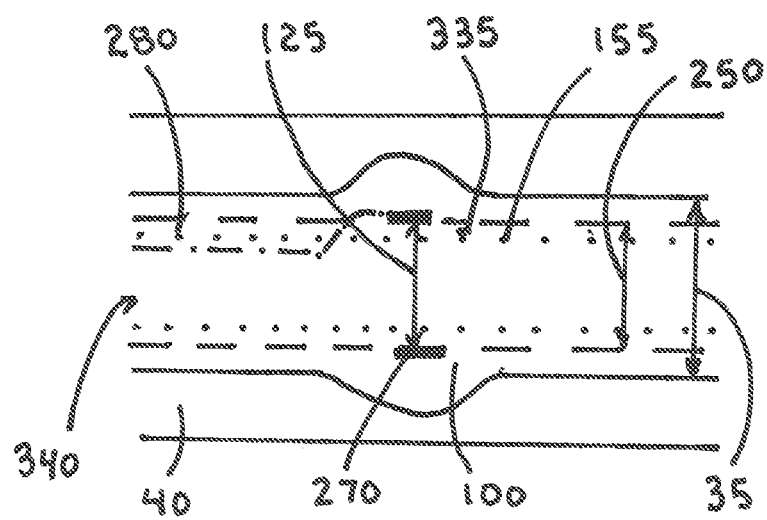
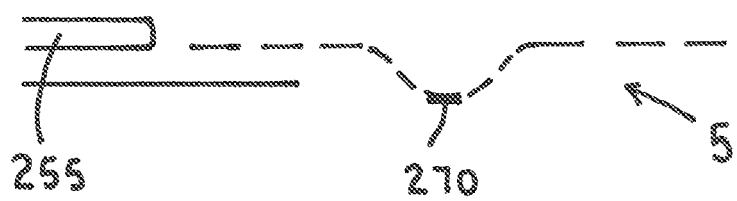

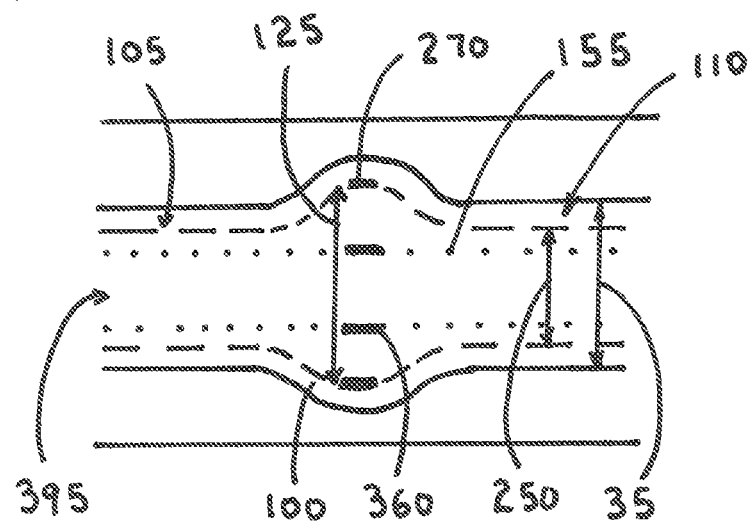
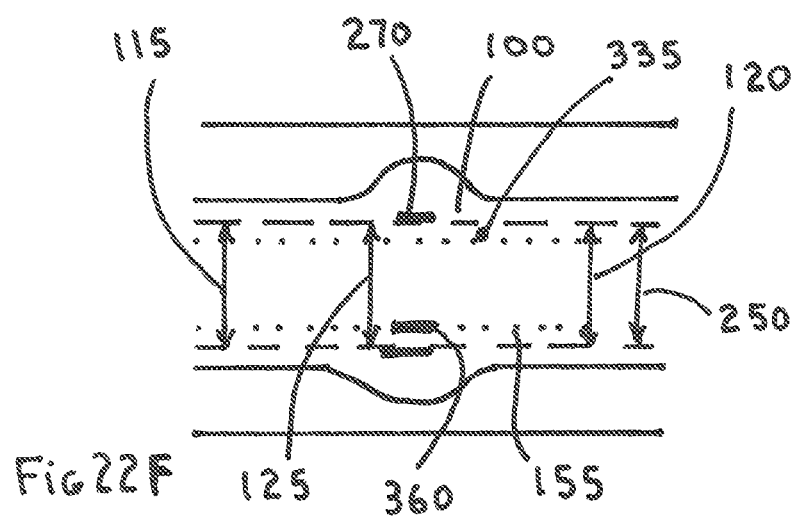

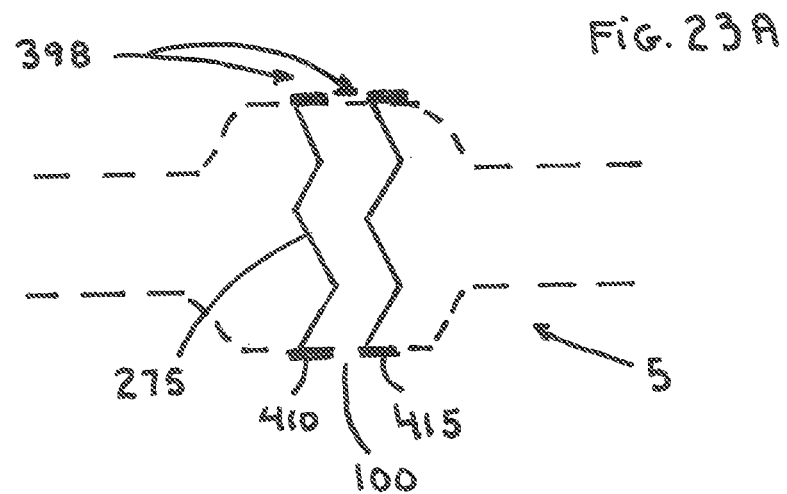
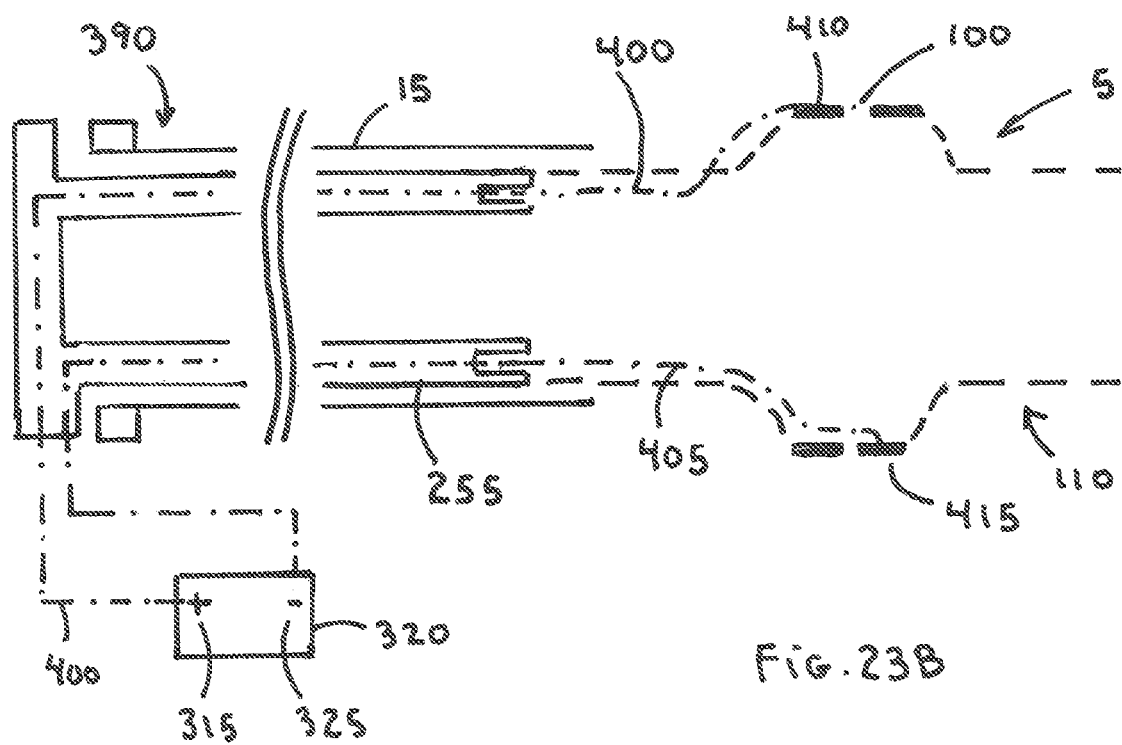

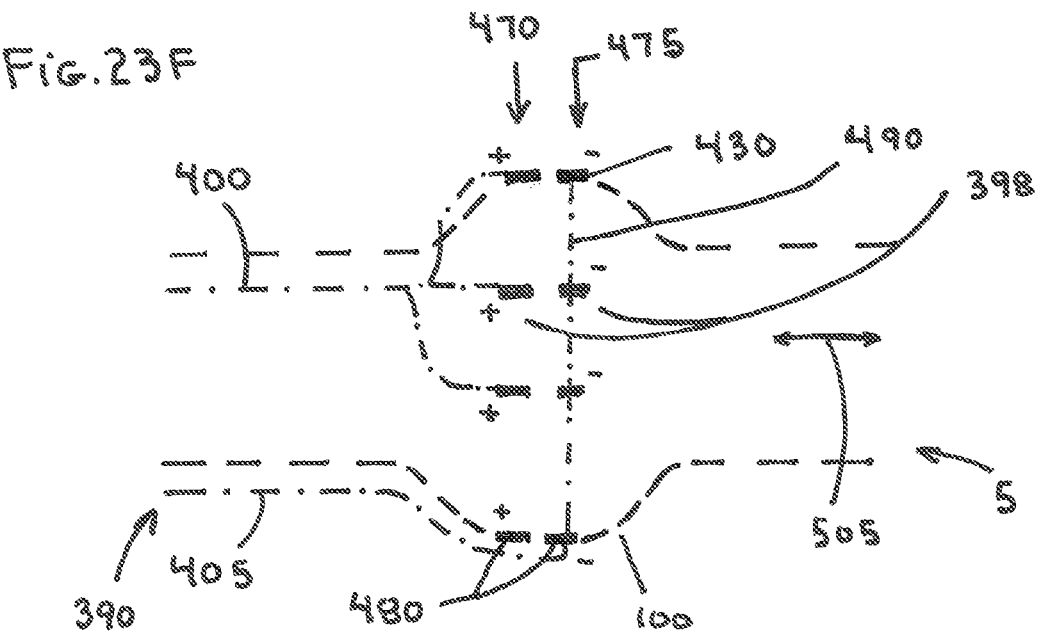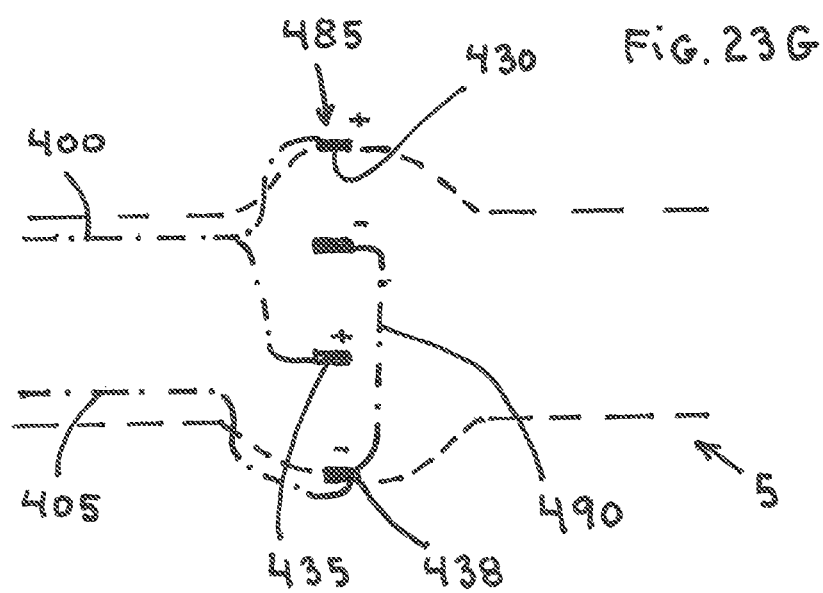

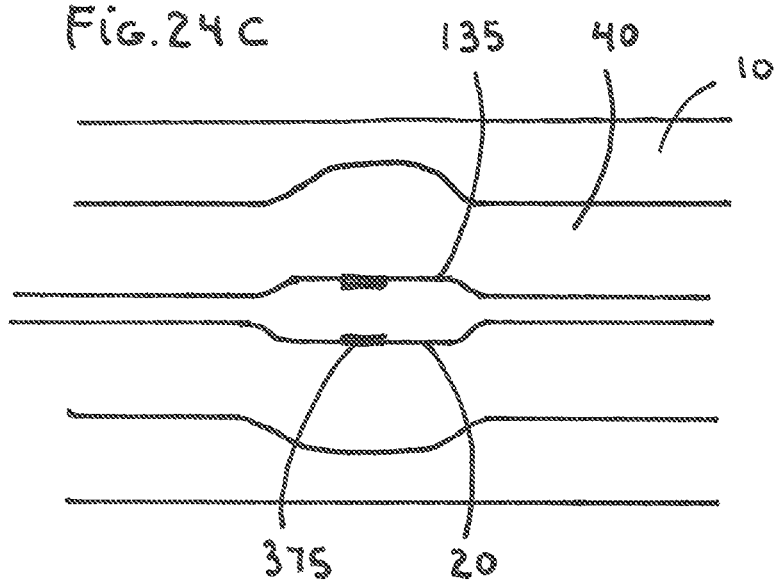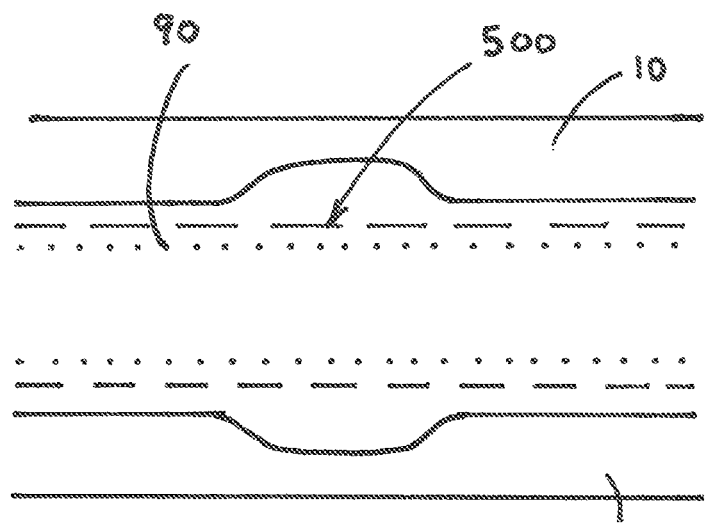

COMPRESSION STENT DEVICE AND METHODS

CROSS REFERENCE TO RELATED APPLICATIONS

This patent application makes reference to and thereby incorporates all information found in the nonprovisional patent application Ser. No. 16/002,144 entitled Compression Stent with Electrodes, filed 7 Jun. 2018 by William J. Drasler, et. al.

BACKGROUND OF THE INVENTION

Renal Nerve Denervation (RDN) has been performed via various techniques in order to block efferent and afferent sympathetic nerve activity between the central nervous system and the kidneys and nerves that are involved with vascular control in order to treat hypertension (HTN). One technique utilizes radiofrequency (RF) energy delivered to the nerves that surround the renal arteries to cause necrosis of the nerves and hence block sympathetic signaling. The RF energy can be delivered at specific sites along a perimeter of the renal artery at a location between the renal artery ostium at the aorta and sites located near or at the junction of the renal artery with the kidneys. Various catheters with RF electrodes located along the outside of a balloon or located otherwise in contact with the arterial wall have been used to effect such RF treatment of the renal artery. Other energy means have also been utilized to affect a blockage of the sympathetic signaling including the use of ultrasound (US) and delivery of neurotoxic chemicals including alcohol directly to the wall or within the wall of the renal artery.

The problem with the current devices is that they do not deliver the energy or chemical in a uniformly distributed manner to all regions of the renal arterial wall. Some sympathetic nerves that are located near a vein or other heat sink can be shielded or otherwise protected from the thermal aspects of RF or US energy that normally would result in nerve necrosis and can therefore allow one or more of the sympathetic nerves to remain viable. Nerves located further from the sites of chemical injection will be less susceptible to necrosis and subsequent sympathetic signal blockage. Excess use of either RF, US energy or use of chemical toxins can cause the renal artery to become damaged and could result in renal artery stenosis or renal artery aneurysm, either of which can be detrimental to the patient.

What is needed is a device and method that applies a uniform pressure or uniform severing to the sympathetic renal nerves along the perimeter of the renal artery wall and throughout its wall thickness such that the sympathetic renal nerves are completely blocked around the entire perimeter and blocked to a distance from the renal artery lumen that includes all of the sympathetic renal artery nerves.

RF Background:

Significant improvement in consistency of energy delivery to the nerves located along the perimeter of the arterial wall and within the adventitial layer could be made if the arterial wall were to be compressed while the ablative energy is being delivered. Such vessel wall compression could initiate trauma and dissections that could lead to intimal hyperplasia and stenosis of the artery, such as renal artery stenosis, for example. the device and method used to provide more consistent ablation to the renal nerves must also obviate the potential for renal artery stenosis.

SUMMARY

The present invention is a compression stent that is intended to block sympathetic nerve signals that traverse through nerve fibers located in the walls of the renal arteries. The sympathetic nerves generally run in the adventitial layer and outer portion of the media of the renal arteries; many are located within approximately 2 mm of the arterial lumen. The compression stent can apply a compression or a pressure that causes the nerves to become compressed and thereby block nerve signal transmission. Alternately, the stent can apply a compression to the vessel wall that causes the stent to migrate through the arterial wall tissue causing the nerve to become severed or nerve signal to become disrupted as the stent frame migrates through the tissue. The compression stent can also be applied to other arteries or tubular members of the body that require a compression of the wall of the tubular member to block nerve signal transmission or for other purposes. Compression of nerves found in arteries of the body via implantation of a compression stent can also be used in the treatment of anxiety, diabetes mellitus, obesity, sleep apnea, and other disorders that have been correlated to increased sympathetic nerve activity.

Embodiments the compression stent include a self-expanding (SE) and a balloon expandable (BE) stent that applies an outward pressure onto the renal artery wall that causes a portion of the renal artery to enlarge in diameter from its initial luminal diameter by a significant amount or significant percentage of approximately 50% (range 30-100%); a 5 mm diameter renal artery, for example, could be enlarged via the compression stent to a diameter of 8 mm or larger; such significant enlargement of the renal artery diameter will cause the renal sympathetic nerves to become blocked via compression or via severance. A balloon expandable (BE) stent of the present invention can apply a compressive force upon the nerve that causes an immediate block in nerve signal transmission. A self-expanding (SE) stent which continues to grow in diameter toward an increasingly larger equilibrium diameter can cause nerve blockage immediately in some instances and over a period of hours or days in other instances.

A covering can be applied or attached to the stent frame structure to prevent the stent struts from migrating into the wall of the artery and migrate through the inner and outer elastic lamina of the artery; the presence of the covering causes the stent to apply an outward pressure to the vessel wall thereby compressing the nerve fiber and blocking the nerve signals in the wall of the renal artery. Alternately, the stent frame can be non-covered such that the enlarged diameter of the stent will cause the stent struts to migrate through the vessel wall tissue, migrate through the inner and/or outer elastic lamina, migrate into or through the nerve fiber, and ultimately cause nerve signal blockage via nerve severing or via electrical nerve signal continuity between the nerve cell interstices and the extracellular space surrounding the nerve. A drug such as Taxol, Sirolimus, or other drug that prevents cellular migration into the vessel lumen can be applied to the surface of the stent or the covering to assist in preventing intimal hyperplasia.

In other embodiments one or more focal regions are located along a SE or BE stent such that a non-focal portion of the stent has a diameter that is similar to the diameter of the native renal artery and the focal stent regions have a diameter that is significantly larger than the luminal diameter of the native renal artery such that sympathetic nerve signals are blocked in the focal regions of the stent. The focal region with a significantly enlarged diameter will cause the arterial wall to become compressed along a circular perimeter such that a sympathetic nerve cannot extend across the focal region without becoming blocked via either compression or via severance of the nerve fibers. The focal region is located between a non-focal proximal region and a non-focal distal region of the stent frame; the non-focal regions each have a diameter that is similar to the diameter of the native artery lumen. In some embodiments for the stent the focal region has a focal region diameter that is at least 30% larger than the non-focal region diameter for either of the non-focal regions, in other embodiments the focal region diameter is at least 50% larger than the diameter of the non-focal regions, and in yet other embodiments, the focal region diameter is at least 100% larger than the diameter of the non-focal regions in an expanded configuration of the stent.

An outer focal covering can be applied to the stent in the region of the focal diameter enlargement to cause the focal region to apply a focal pressure along a perimeter of the arterial wall and block nerve conduction via external compression. The focal covering also prevents migration of cells from the arterial wall into the lumen of the compression stent resulting in stenosis of the artery. The focal covering should be formed from a material that prohibits cells from passing through its wall structure. The focal covering should in some embodiments extend into at least a portion or all of the non-focal regions of the stent to ensure that cellular migration from the artery wall into the stent lumen near the focal region is not allowed to occur. The focal covering can be formed from a thin film (approx. 0.0005 inch-0.002 inch) of porous expanded polytetrafluoroethylene (ePTFE), porous polyurethane, thin fibrous material, tissue-based materials, or other thin films that will prevent migration of the stent struts through the vessel wall as the stent places the vessel wall into a state of compression.

Alternately a focal region without an outer focal covering can apply a pressure along a perimeter that will cause the nerve fiber to become blocked via migration of the stent frame through the vessel wall tissue causing severance of the nerve fibers. The migration of the uncovered stent struts through the wall of the artery over a time period ranging from days to months. Such migration of the stent into the wall of the artery can sever the nerve fiber and disrupt the nerve transmission.

A SE embodiment of the compression stent having one or more focal regions can be formed via thermal processing of an elastomeric metal stent frame, for example, Nitinol (NiTi), such that the focal region has an equilibrium diameter that is significantly larger in diameter than other non-focal regions of the stent that have a diameter that is similar to that of the native arterial lumen diameter. In one embodiment the SE stent having the focal region with a significantly enlarged diameter can contain an inner luminal fabric or covering adjacent the focal region of the stent to form a continuous lumen diameter for the stent that forms a generally cylindrical shape having a diameter that is similar to the diameter of the native vessel lumen. The luminal fabric or covering serves to provide a generally cylindrical tubular shape across the vessel lumen adjacent the focal region of the stent extending from the proximal stent region to the distal stent region. The luminal fabric or covering can prevent thrombosis in the vessel lumen adjacent the focal region of the stent, and can reduce the ability of stenosis of the artery due to smooth muscle cell (SMC) proliferation and migration into the vessel lumen adjacent the focal region of the stent.

A BE embodiment of the compression stent having one or more focal regions can be formed from standard BE materials used for BE coronary and peripheral vascular stenting. A focal region of the stent can be formed such that it is able to expand significantly larger in diameter than a proximal and distal stent region. For example, a larger strut length or a lesser number of struts per stent length or diameter or other altered stent wall structure can be applied to the focal region of the BE stent frame to accomplish a larger attainable diameter for the focal region in comparison to other regions of the stent. To expand the BE compression stent having a focal region of significantly larger diameter will be accomplished using a dilation balloon having a balloon focal region. The balloon focal region has a diameter that is significantly (i.e., 30-100%) larger in diameter than the diameter of other remaining regions of the balloon. The balloon can be formed from standard noncompliant or semi-compliant materials used to expand standard BE stents in coronary and peripheral arterial applications. Such a balloon with a focal region is formed to retain its larger diameter focal region during expansion and deflation of the balloon. The focal region of the stent is positioned adjacent the focal region of the balloon during the delivery of the catheter through the vasculature and during expansion of the compression stent, the delivery catheter is positioned such that the focal regions of the balloon and stent are adjacent the region of the native renal artery that has the sympathetic nerves that are intended to be blocked. Expansion of the balloon will expand the focal region of the stent out into compressive contact with the renal artery causing the wall of the renal artery to compress and causing the renal sympathetic nerves to become blocked. A focal covering can be bonded or attached to the focal region of the BE stent. The focal covering can be formed from a thin film of porous expanded polytetrafluoroethylene (ePTFE), porous polyurethane, thin fibrous material, tissue-based materials, or other thin films that will prevent migration of the stent struts through the vessel wall. Alternately, a focal covering need not be applied to the focal region of the compression stent to allow the stent struts to migrate through the vessel wall tissue and cause severance of the sympathetic nerve fibers. A luminal covering can be attached to the proximal and distal stent regions of the compression stent and located within the lumen of the blood vessel; the luminal covering has a diameter that is similar to the diameter of the proximal and distal regions of the stent. The luminal fabric or covering of this embodiment must be able to expand during expansion of the focal region of the balloon and then rebound back to a diameter that matches the diameter of the native vessel. This luminal covering can be formed from an elastomeric film such as microporous polyurethane (PU) or other elastomeric polymer. The luminal covering can be joined to the proximal and distal stent regions. The luminal covering will prevent thrombosis and reduce the likelihood for SMC proliferation and migration into the vessel lumen adjacent the focal region of the stent.

In yet another embodiment the SE compression stent can be formed such that it has a focal region that makes compressive contact with the wall of the tubular member or vessel of the body and compresses the wall tissue of the vessel and also a luminal stent region that extends in a cylindrical manner with the same diameter as the lumen of the native vessel. The luminal stent can be joined, for example, to SE proximal and distal regions of the stent via various bonding, attaching or welding techniques or can be formed contiguously via 3D machining techniques. The entire stent, including the luminal stent region can be formed from SE materials using thermal processing to form specific focal regions with a larger diameter than a non-focal region diameter. The focal region and/or luminal stent region can have a covering attached to them to provide benefits as described earlier.

In further other embodiments the compression stent can be formed such that the proximal and distal regions are formed from a BE material and the focal region is formed from a SE material. The BE portions of the stent allow the compression stent to be mounted onto a dilation balloon. The dilation balloon can be either cylindrical in shape or it can be a focal balloon with the focal balloon region of significantly larger (i.e., 50% larger, range 30-100%) focal region diameter than the diameter of non-focal regions of the balloon. The focal region of the balloon is positioned adjacent the SE focal region of the compression stent. Upon release of the balloon mounted stent from the sheath, the SE focal region expands outwards. The balloon can then be expanded to dilate the BE non-focal regions of the compression stent. In one embodiment a cylindrical balloon will dilate the BE proximal and distal regions of the compression stent to match the diameter of the native artery while the SE focal region is designed to expand significantly larger than the native artery and expand to its fullest extent over a time period of minutes to days. In another embodiment a balloon with a focal region that is positioned adjacent to the SE focal region of the stent allows the focal region of the stent to expand outwards to the fullest extent of the balloon focal region diameter immediately and affect a blockage of all sympathetic nerves. Even after deflation and removal of the dilation balloon additional expansion of the SE focal region will further cause compression or severance of the sympathetic nerves as it reaches the stent focal region full equilibrium diameter; this phenomenon is observed clinically with the SE TAVR stent valves which often can cause bundle branch block in the heart after implantation of the device. The compression stents of these embodiments can also contain a focal covering and/or a luminal covering. The compression stents of these embodiments also can contain a luminal stent located adjacent the focal stent region and having a diameter that is similar in diameter to the native artery lumen diameter.

Drugs can be used with any of the embodiments of the present invention to enhance their effectiveness; such drugs can be placed onto the focal region of the stent, the proximal or distal regions of the stent, the luminal stent, the focal covering, or the luminal covering, or any covering located on the stent. For example, anti-proliferative drugs such as Taxol or Sirolimus can be used to prevent cellular proliferation and migration into the luminal region that could lead to vessel stenosis. Also, antithrombotic agents can be placed onto the compression stent device to reduce thrombosis in the lumen region of the vessel adjacent the focal region of the stent. Other drugs including alcohol or nerve blocking or necrotic agents such as alcohol can be applied to any portion of the present invention to assist in causing nerve blocking.

The compression stent of the present invention can be formed from a material that allows the stent frame to be heated up via an external application of energy including RF, US, focused US, microwave, other electromagnetic energy form, magnetic coupling, IR light, UV light or other energy forms. For example, if the nerve fibers were not entirely blocked along a perimeter of the renal artery, energy could be delivered to the stent, absorbed by the stent, and cause the stent to increase in temperature resulting in further trauma to the sympathetic nerves of the renal artery, and provide additional therapeutic benefit by further blocking sympathetic nerve transmission. The stent could be designed such that it contains, for example, a coil that interacts with an external magnetic field that allows it to be heated noninvasively via energy coupling to the coil at an energy frequency that is characteristic to the coil energy absorption frequency.

The compression stent of the present invention can be formed with a circuit that is able to detect continuity of electrical conduction through the wall of the renal artery. The circuit can be probed initially during implant of the compression stent to determine if the sympathetic nerve signal has been blocked. If the nerve signal is not blocked, further dilation of the stent can be performed prior to exiting the interventional access site during the interventional procedure. If the stent is probed externally at a later time, it can be determined if the nerve blockage has been durable. If the blockage is not durable, then further dilation of the stent can be accomplished or else a noninvasive thermal heating of the stent via an external energy means can be utilized.

The present invention includes the use of various types of ablative energy being applied to the wall of an artery while the arterial wall is being compressed such that it is thinner in the radial direction. The thinner arterial wall allows the ablative energy or application of chemical ablative agents to be delivered across and through the entire vessel wall and thereby ensure that all nerves within the vessel wall have been ablated. The compression can be performed via a dilation balloon having an inflated diameter ranging from 30% to over 100% of the native arterial diameter. While the balloon is in an inflated configuration, an ablative energy is applied to the vessel wall to cause nerve ablation resulting in loss of nerve signal conduction. Such ablative energy can include radiofrequency (RF) energy, ultrasound energy, thermal heating energy, microwave energy; chemical ablative agents include alcohol and others.

Following the application of an ablative modality to a compressed vessel wall, the vessel may have a tendency to undergo smooth muscle cell (SMC) hyperplasia and could lead to formation of an arterial lumen stenosis. To prevent this, the present device and methods include the placement of a covered stent over the region that has been ablated; the covered stent obviates the SMC hyperplasia and allows the arterial wall to heal without stenosis. To obviate potential difficulty associated with placing a stent across a traumatized blood vessel lesion created by over distension of the blood vessel and compression of the blood vessel wall, the covered stent of embodiments of the present invention is positioned across the site of the treatment site prior to performing the nerve blockage treatment.

The stent frame for the compression stent is anticipated to be formed from a resilient or elastic material such as Nitinol, for example. The compression stent can also be formed from a biodegradable material including variants of polyglycolic acid, polylactic acid, and other biodegradable materials used in the vascular stenting industry.

The electrode configuration found on either the compression stent or the dilation balloon can be unipolar or bipolar and can be comprised of a plurality of electrodes located along the perimeter of the stent focal region or the balloon focal region. when a plurality of electrodes are positioned along the perimeter, each electrode can provide a localized high current density that that results in a more uniform ablation around the perimeter of an arterial wall such as the renal artery. If the spacing between electrodes is too far, then the tissues located adjacent to the spacing may not be properly ablated. The number of individual electrodes positioned along the perimeter of focal region is 8 electrodes (range 3-16). If more than one row of electrode extends around the perimeter of the stent or dilation balloon, then additional electrodes can be positioned on the dilation balloon or the compression stent.

BRIEF DESCRIPTION OF THE DRAWINGS

FIG. 1E is a longitudinal section view of a blood vessel with a compression stent located along the lumen of the blood vessel.

FIG. 1F is a cross-sectional view of a blood vessel with a compression stent located along the lumen of the blood vessel causing the blood vessel wall to become compressed.

FIG. 1G is a cross-sectional view of a blood vessel showing a compression stent that has migrated into the vessel wall and causing trauma to the nerve.

FIG. 2C is a longitudinal view of an inflated compression stent located on an inflated dilation balloon.

FIG. 2D is a cross-sectional view of a blood vessel with a compression stent located on its lumen and causing the blood vessel wall to become compressed and causing trauma to the nerve.

FIG. 3 is a longitudinal sectional view of a compression stent having a covering attached to a surface of the compression stent.

FIG. 4A is a longitudinal view of a compression stent having a self-expanding stent focal region and self-expanding non-focal regions; the compression stent is held in a nonexpanded configuration by an external sheath.

FIG. 4B is a longitudinal view of a compression stent with a self-expanding stent focal region and self-expanding non-focal regions that has been released from an external sheath to its expanded configuration.

FIG. 6A is a longitudinal view of a compression stent in an expanded configuration having a stent focal region and having a covering attached to the stent surface.

FIG. 6B is a longitudinal view of a compression stent in an expanded configuration having a focal region and having a covering that is attached to the surface of the focal region.

FIG. 6C is a longitudinal view of a compression stent in an expanded configuration having a focal region and having a luminal covering that is not attached to the surface of the focal region; the luminal covering does not grow in diameter as the focal region grows in diameter.

FIG. 7A is a longitudinal view of a balloon expandable compression stent having a stent focal region in a nonexpanded configuration mounted onto a dilation balloon having a balloon focal region.

FIG. 7B is a longitudinal view of a balloon expandable compression stent having a stent focal region in an expanded configuration mounted onto a dilation balloon having a balloon focal region; the stent focal region has compressed the wall of a blood vessel.

FIG. 7C is a longitudinal view of a balloon expandable compression stent having a focal region that grows in diameter at a greater rate relative to the non-focal regions.

FIG. 8A is a longitudinal view of a balloon expandable compression stent with a stent focal region in an expanded configuration positioned onto a dilated balloon having a balloon focal region; a covering is attached to the stent focal region.

FIG. 8B is a longitudinal view of a balloon expandable compression stent with a stent focal region in an expanded configuration positioned onto a dilated balloon having a balloon focal region that is inflated to a pressure ranging from 1-3 atm; a covering is attached to the surface of the stent.

FIG. 8C is a longitudinal view of a balloon expandable compression stent with a stent focal region in an expanded configuration positioned onto a dilated balloon having a balloon focal region that is inflated to a pressure ranging from 4-12 atm; a covering is attached to the surface of the focal region.

FIG. 10A is a longitudinal view of a compression stent held in a nonexpanded configuration in an external sheath; the compression stent has an outer stent focal region and an luminal stent.

FIG. 10B is a longitudinal view of a compression stent held in an expanded configuration; the compression stent has an outer stent focal region and an luminal stent.

FIG. 11 is a longitudinal sectional view of a compression stent in an expanded configuration with an outer stent focal region, a luminal stent, a focal covering and a luminal covering.

FIG. 16 is a plan view of a self-expanding compression stent in a nondeployed configuration contained within a delivery sheath.

FIG. 17 is a plan view of a compression stent that has been expanded within a blood vessel causing the vessel wall to become compressed and resulting in blockage of nerve transmission.

FIG. 19B shows a two-component system having a first component compression stent to cause nerve conduction block followed by a covered blocking stent to block tissue ingrowth into the blood vessel.

FIG. 19C shows a balloon expandable blocking stent loaded onto the outside surface of a dilation balloon.

FIG. 20E shows the self-expanding compression stent in an expanded configuration after deflation of the dilation balloon.

FIG. 21A shows a compression stent having one or more electrodes located in the expanded focal region of the stent and a radiofrequency generator able to deliver energy and deliver it to the electrodes via a conduction wire located in the pusher member.

FIG. 21E is a plan view of the compression stent following deflation and removal of the dilation balloon and return of the stent focal region to a diameter that matches the diameter of the native vessel.

FIG. 21F shows a compression stent being released from a delivery sheath and the electrodes located on the stent focal region are in continuity with a conduction wire located in the delivery sheath wall.

FIG. 22E shows the focal region of the compression stent remaining in an expanded configuration causing compression of the native vessel wall.

FIG. 22F shows the focal region of the compression stent along with the covering returning to match the diameter of the native vessel following delivery of radiofrequency energy and removal of the dilation balloon.

FIG. 24C is a plan view of the dilation balloon in a deflated configuration following delivery of radiofrequency energy to the native vessel wall via electrodes located on the balloon focal region surface.

FIG. 24D is a plan view of a covered stent placed in the native vessel at a location where the dilation balloon has been inflated in order to cover the vessel wall trauma and prevent cellular migration into the lumen of the native vessel.

DETAILED DESCRIPTION

Figure 1A:
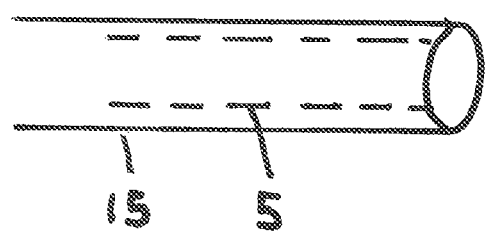
FIG. 1A is a longitudinal section view of an embodiment of a self-expanding compression stent in a nondeployed configuration held by an external sheath.
Figure 1B:
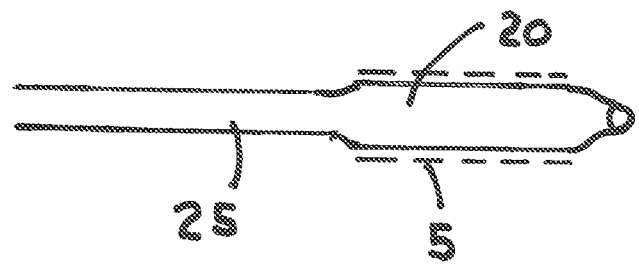
FIG. 1B is a longitudinal section view of an embodiment of a balloon expandable compression stent in a nondeployed configuration mounted on a dilation balloon.

FIGS. 1A-1F show embodiments of a compression stent (5) that is being deployed into a renal artery (10), for example, or other tubular member of the body. The compression stent (5) can be a self-expanding (SE) stent that is held into a small diameter configuration via an external sheath (15) as shown in FIG. 1A. Alternately, the compression stent (5) can be a balloon expandable (BE) stent that is mounted onto the outside of a dilation balloon (20) that is located at the distal end of a balloon dilation catheter (25) as shown in FIG. 1B. As a BE stent, the compression of the nerve and blockage of the nerve signal can be observed very quickly, either immediately or within minutes after implantation of the stent. If the compression stent (5) is formed from with a SE character, the blockage of the nerve signal often will occur within a period of time ranging from minutes to hours to days after implantation of the compression stent. The SE compression stent will continue to grow in diameter after the immediate implantation diameter towards its equilibrium diameter (as found for the SE stent in free space) and thereby result in nerve blockage as observed in the clinic, for example, with SE stented valves that are placed on or near the aortic annulus in TAVR procedures.

Figure 1C:
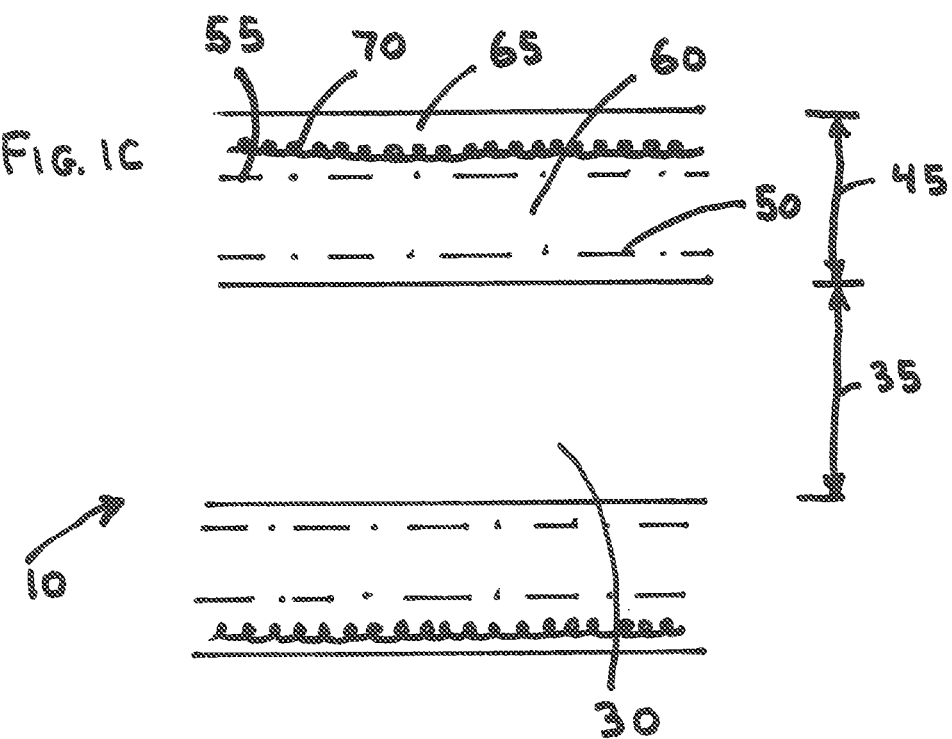
FIG. 1C is a longitudinal section view of an arterial blood vessel.
Figure 1D:
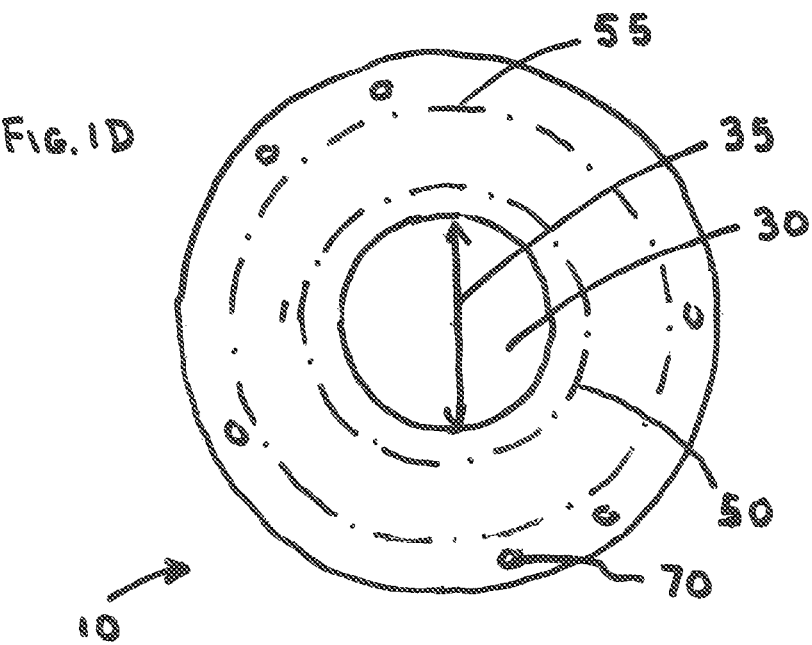
FIG. 1D is a cross-section of an arterial blood vessel.

The artery (10) as shown in FIGS. 1C and 1D has a vessel lumen (30) with a native lumen diameter (35) and a vessel wall (40) with a native wall thickness (45). The vessel wall has an inner elastic lamina, IEL (50) and an external elastic lamina, EEL (55); located between the IEL (50) and EEL (55) is a medial layer (60). Outside of the EEL (55) is the adventitial layer (65) in which most of the sympathetic nerves (70) reside. The nerves (70) extend through the adventitial layer (65) as well as the outer layers of the media extending along in the axial direction of the artery. Upon release of the SE compression stent (5) or BE compression stent (5) into the vessel and into its expanded state, the compression stent (5) causes the vessel to expand in diameter to a significantly larger (i.e., 30-100% larger than its native lumen diameter (35)) expanded lumen diameter (75) and compresses the adventitial layer (65) that contains the sympathetic nerve fibers (70) to a smaller compressed wall thickness (80) as shown in FIGS. 1E and 1F. The compression of the nerve fibers can lead to blockage of nerve signal transmission through the nerve fibers. For a stent that is not provided with a covering material as seen in FIG. 1G, the stent struts can migrate through the vessel wall and sever the nerve fibers causing a loss of sympathetic nerve signaling.

Figure 2B:
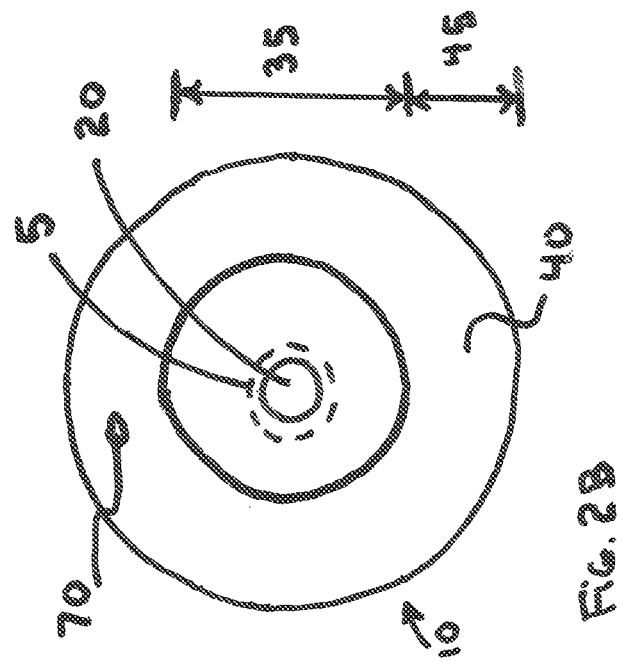
FIG. 2B is a cross-sectional view of blood vessel with a compression stent located on a noninflated dilation balloon that is in the vessel lumen.
Figure 2A:
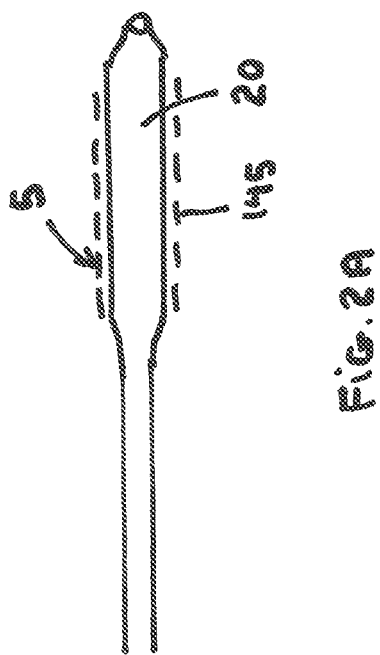
FIG. 2A is a plan view of a dilation balloon in a noninflated configuration with a compression stent located on the balloon.

FIGS. 2A-2B show a BE compression stent (5) being inserted in its nondeployed or nonexpanded configuration into a native arterial vessel or tubular member of the body. The vessel has a native lumen diameter (35) and a native wall thickness. Upon expansion of the dilation balloon (20) (FIGS. 2C and 2D) to a significantly larger (i.e., the balloon is 50% larger, range 30-100% larger than the native lumen diameter) inflated balloon diameter (85), the compression stent (5) causes the blood vessel or artery (10) to enlarge in diameter to a significantly greater expanded lumen diameter (75) and the native wall thickness thins down to a smaller thickness. Nerves (70) that are found in the vessel wall will become compressed and are exposed to severance via the stent struts of the compression stent (5). The severance of such nerves (70) can provide a therapeutic benefit in the treatment of hypertension (HTN).

FIG. 3 shows either a BE or SE compression stent (5) having a stent covering (90) that is attached or bonded to the stent frame structure (95), the stent frame structure being defined by its geometric design and stent pattern that forms the compression stent. A separate name and reference numeral will be presented for the stent covering (90) that is located in various regions of the compression stent (5). The stent frame being comprised of hinges (or bent regions), struts (or straight regions that join bent regions), connectors (that connect rings of stent frame members together), and other structures that form the stent frame. The covering (90) can be thin film of ePTFE, microporous PU, microporous polyethylene terephthalate (PET), nylon, or other microporous polymeric material, or tissue material that will prevent the stent frame structure (95) from migrating through the vessel wall tissue, but will allow for tissue ingrowth for healing of the compression stent (5) and covering (90) to occur. The material can be noncompliant or can be semi-compliant material. The covering (90) can be attached to the stent frame via sutures, adhesives, thermal bonding, and encasement of the stent within two layers of covering (90) or via other attachment means.

One embodiment of the present compression stent (5) invention as shown in FIGS. 4A and 4B is a SE stent that contains a stent focal region (100) positioned between a stent proximal region (105) and a stent distal region (110); the stent proximal region (105) and stent distal region (110) can collectively be referred to as the stent non-focal regions (152). FIG. 4A shows the stent in a nonexpanded configuration contained within an external sheath; FIG. 4B shows the stent in an expanded state. The proximal region diameter (115) and distal region diameter (120) are approximately equal to the native lumen diameter (35) of the native artery (10), although a small oversizing of the stent from zero to 15% for the non-focal regions can be made relative to the native lumen diameter. The stent focal region (100) has a stent focal region diameter (125) that is approximately 50% larger (range 30-100% larger) than the native lumen diameter (35) and approximately 50% larger (range 30-100%) than the stent non-focal region diameter (128), the stent non-focal region diameter being an average of the stent proximal region diameter (115) and the stent distal region diameter (120). The stent proximal region (105) and stent distal region (110) can be attached to the stent focal region (100) via bonding, welding, soldering or other process methods; alternately the stent regions can be formed contiguously with each other via standard mechanical, laser machining methods, thermal processing methods, or other processing methods including machining all regions of the stent frame from a single metal tube, for example. The outward pressure provided by the stent focal region (100) against the vessel wall is approximately equivalent to a dilation balloon (20) placed inside the lumen of the artery (10) and inflated to 6 atm (range 5-10 atm). More than one stent focal region (100) can be contained in the compression stent; one or more non-focal regions (for example, the proximal and distal regions) can be located anywhere adjacent axially to the one or more stent focal regions. The presence of the focal region allows a greater applied pressure (force/area) to be applied to the vessel wall owing to a smaller area of applied force located in the focal region alone. This greater applied pressure allows the vessel wall to undergo a greater compression pressure along a perimeter of the vessel wall resulting in either a severance of the nerve fibers via the stent frame or via compression of the nerve fiber and loss of signal transmission through the nerve fiber.

Figure 5B:
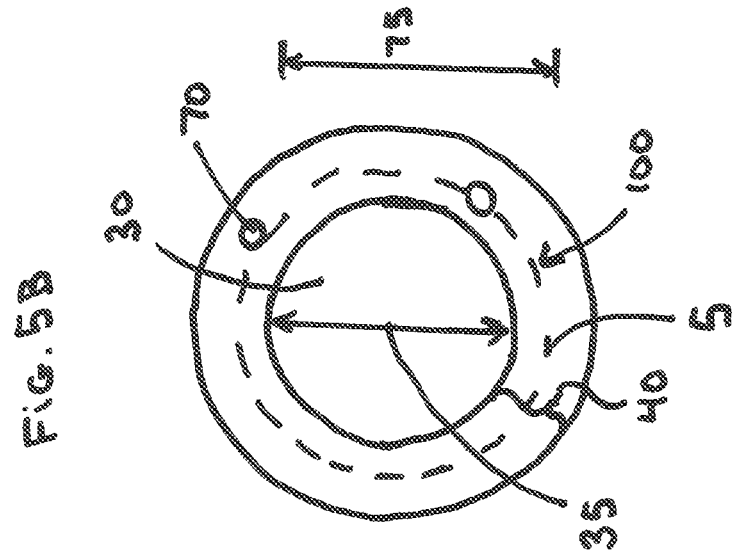
FIG. 5B is a cross-sectional view of a blood vessel having a compression stent located in the vessel lumen and causing the vessel wall to become compressed further causing trauma to the nerves.
Figure 5A:
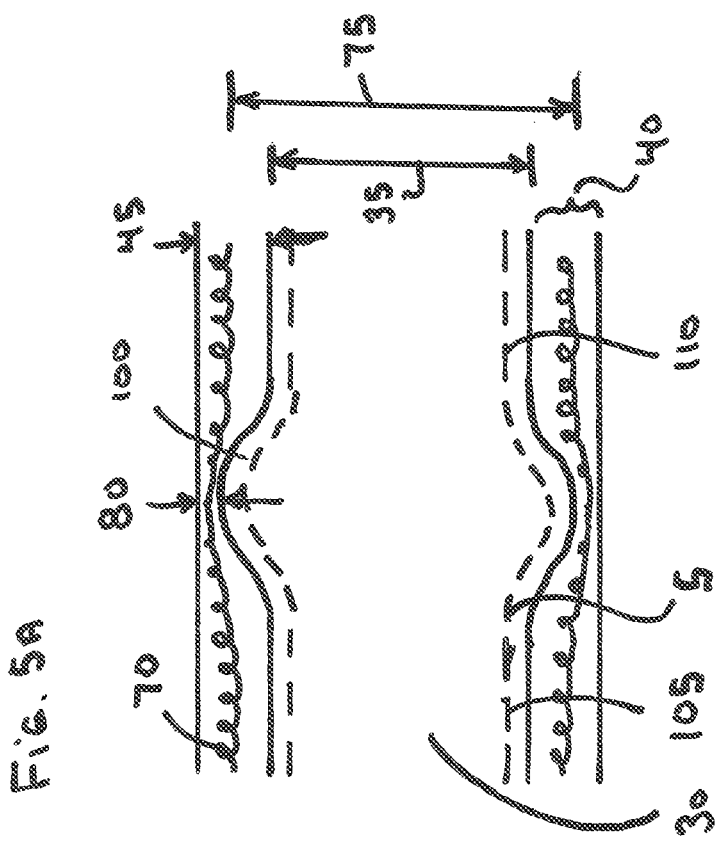
FIG. 5A is a longitudinal sectional view of a blood vessel having a compression stent located in the vessel lumen and causing the vessel wall to become compressed further causing trauma to a nerve.

As shown in FIGS. 5A and 5B the SE compression stent (5) of this embodiment is formed with the stent proximal region (105), stent distal region (110), and stent focal region (100) constructed from an elastic metal such as Nitinol, Elgiloy, for example. The compression stent (5) has a stent focal region (100) that is applying a large pressure onto the nerve fiber; the vessel or artery (10) has enlarged in its expanded lumen diameter (75) adjacent to the stent focal region (100) from its native lumen diameter (35) to a significantly larger expanded lumen diameter (75), and the vessel native wall thickness has thinned down to a compressed wall thickness. The nerve fiber has been severed by a strut of the stent frame and caused the nerve fiber to lose sympathetic transmission; another nerve fiber has been compressed and has lost its ability for sympathetic nerve transmission.

A covering (90) can be applied via attachment, suturing, adhesive bonding, encapsulation, or other methods to the compression stent (5) over its entire surface as shown in FIG. 6A in an expanded state or only in the focal region of the stent forming a focal region covering (130) as shown in FIG. 6B. The presence of a covering (90) that is attached to the wall of the compression stent will allow the compression stent (5) to compress the vessel wall tissue without migration of the stent frame or stent struts (145) through the tissue. The covering can be a porous material such as found in a vascular graft to allow cellular tissues to penetrate the covering and provide a healing capability to the tissues that reside on the luminal side of the covering. The pressure applied to the nerve fiber via the focal region of the stent will cause the nerve fiber to compress in its cross section and will cease to transmit sympathetic signals. Alternately, the covering can reside on the inner surface of the stent as shown in FIG. 6C and can remain unattached to the stent wall in the stent focal region. As the stent focal region grows outwards to a significantly larger diameter than the native lumen diameter, the covering located in the stent focal region can become a luminal fabric or covering and can remain in a cylindrical shape that is equal to the stent non-focal region diameter to function as a cellular infiltration resistance; the luminal covering will help to reduce thrombosis due to blood stagnation in the region of the blood vessel lumen that has been expanded in diameter and the luminal covering will help to reduce hyperplastic cellular growth and infiltration into the lumen of the blood vessel between the non-focal regions. The luminal covering or stent focal covering can extend a small distance axially of a few millimeters into the non-focal regions to prevent cellular infiltration.

A BE compression stent (5) can be formed such that the stent proximal region, stent distal region, and stent focal region (100) are all formed from balloon expandable materials such as stainless steel, titanium, and other materials used to form vascular stents. The compression stent (5) can be delivered to the renal artery (10) via a dilation balloon (20) that has a balloon focal region (135) as shown in FIGS. 7A and 7B. The stent focal region (100) is mounted onto the dilation balloon (20) adjacent the balloon focal region. The balloon focal region (135) is formed into the balloon during the balloon blowing process and focal shape of the balloon is retained during balloon inflation. The balloon can be formed from materials including PET, Nylon, Pebax, and other noncompliant and semicompliant materials used in therapeutic balloons for angioplasty. Upon dilation of the balloon, the balloon focal region (135) dilates the stent focal region (100) to a stent focal region diameter (125) that is significantly (i.e., 50% larger, range 30-100% larger) larger than the vessel native lumen diameter (35) and significantly larger than the balloon non-focal regions (150) and significantly larger than the stent non-focal region diameter (128) putting the stent into an expanded state. The vessel wall thickness adjacent the stent focal region (100) has been thinned down to a compressed wall thickness (80) that is smaller than the vessel native wall thickness and causes the nerve fiber to be compressed. The stent struts (145) can migrate through the nerve fiber causing the nerve to sever and lose its transmission capability. The balloon non-focal regions (150) are located adjacent to the stent non-focal regions (152); the balloon non-focal regions (150) extend the stent non-focal regions (152) to a stent non-focal region diameter (128) that is approximately the same as the native lumen diameter (35) with minimal oversizing of the stent non-focal regions (152) by zero to 15% larger than the native lumen diameter.

As shown in FIG. 7C, the balloon non-focal region (150) can be formed with a balloon material that is more noncompliant than the balloon focal region (135) or the balloon non-focal regions are formed using an outer wrap of small diameter multifilament polyethylene terephthalate fibers, for example, such that the non-focal regions (150) are not able to expand in diameter as much as the balloon focal region (135) as the inflation balloon (20) inflation pressure is increased. Increasing the balloon inflation pressure will allow the balloon focal region (135) and the stent focal region (100) to grow in diameter under increasing inflation balloon (20) inflation pressure until a blockage in nerve signal is observed without negatively dilating or imposing trauma onto the native artery on either side of the stent focal region (100). The balloon focal diameter (140) for this embodiment grows at a greater rate than the balloon non-focal diameter (142) such that the relative stent focal to non-focal radius (144) increases with increased inflation pressure in the dilation balloon (20).

The stent covering (90) can be attached along the entire stent structure as shown in FIG. 8A as the balloon is inflated. A stent focal region covering (130) can be attached or bonded onto the compression stent (5) to prevent migration of the stent focal region (100) through the vessel wall as the inflation balloon is inflated to a pressure ranging from 1-3 atm and the focal region reaches a diameter ranging from 30-100% greater than the native lumen diameter as shown in FIG. 8B with the stent in an expanded state. The focal dilation balloon can be further inflated to a larger pressure ranging from 3-12 atm to cause the focal region of the balloon and the focal region of the stent to grow further in diameter of up to 200% of the native lumen diameter. As shown in FIG. 8C, the balloon focal region diameter (140) can be increased at higher balloon inflation pressures to cause the stent focal region diameter (125) to increase a greater diametric amount relative to the stent non-focal diameter (128) thereby generating a greater relative stent focal to non-focal radius (144). To provide for relative growth of the balloon focal region the focal dilation balloon can be formed with a balloon focal region that is either a compliant material such as polyurethane or a semicompliant material Nylon or Pebax. The non-focal regions can be supported with an external layer of noncompliant polymeric material such as polyethylene terephthalate, a braid, or other supported structure to prevent the non-focal regions of the balloon from undergoing diametric growth at the higher pressures as described. The focal dilation balloon can then be inflated to increasing pressures until notation is made by the operator that the nerve conduction signals have been blocked via vessel wall compression or via nerve severance from the compression stent.

Figure 8D:
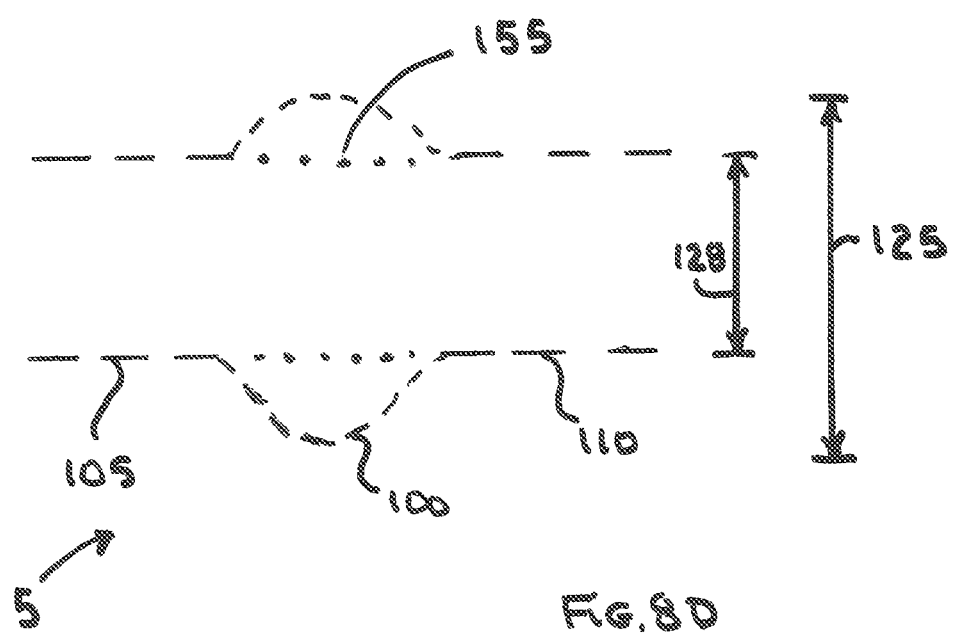
FIG. 8D is a longitudinal view of an expanded compression stent having a focal stent region and having a luminal covering located between the non-focal regions and having the same diameter as the non-focal regions.

A luminal fabric or luminal covering (155) can also extend from the stent proximal region (105) to the stent distal region (110) across the stent focal region (100) to form a cylindrical luminal fabric or luminal covering (155) adjacent to the stent focal region (100) as shown in FIG. 8D and can extend into the non-focal regions. This luminal covering (155) can prevent thrombosis form occurring in the vessel lumen (30) due to the greater luminal diameter provided by the stent focal region. The luminal fabric or luminal covering (155) also assists in blocking smooth muscle cell migration or cellular hyperplasia into the vessel lumen (30) adjacent the stent focal region. The luminal fabric or luminal covering (155) for the BE compression stent (5) having a stent focal region (100) that is expanded outwards via the balloon focal region (135) requires a luminal covering (155) that is elastic in character such that it can expand during inflation of the balloon focal region (135) and can rebound back to a native lumen diameter (35) after the dilation balloon (20) has been deflated. The luminal fabric or luminal covering (155) can be formed from a microporous PU, fibrous PU, silicone, or other microporous elastomeric polymeric material.

Figure 9B:
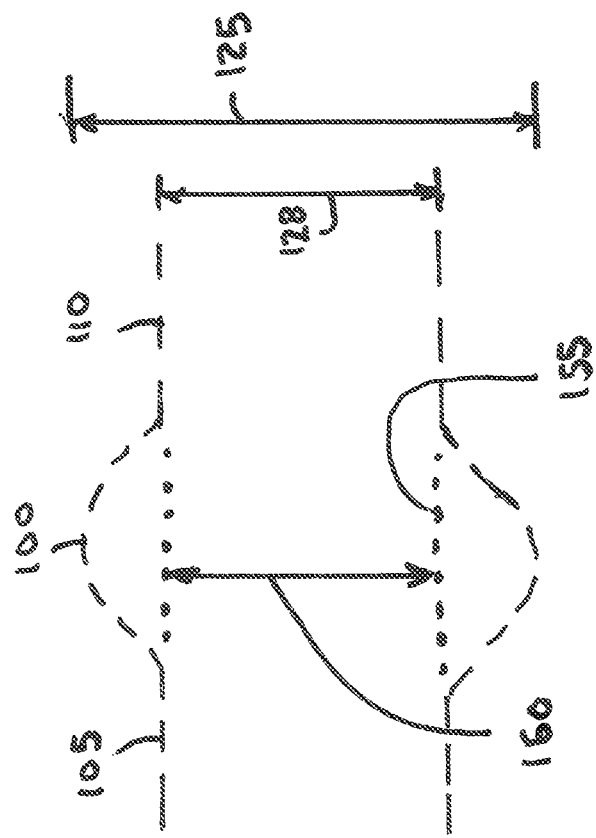
FIG. 9B is a longitudinal view of a self-expanding compression stent held in an expanded configuration; the compression stent has a luminal covering extending between the stent non-focal regions.
Figure 9A:
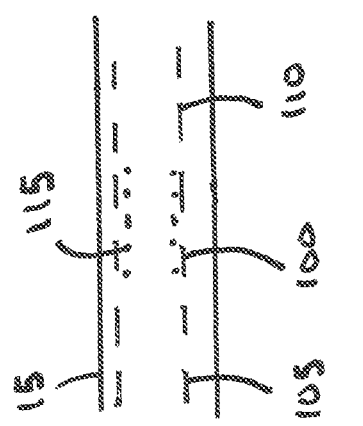
FIG. 9A is a longitudinal view of a self-expanding compression stent held in a nonexpanded configuration within an external sheath; the compression stent has a luminal covering near the focal stent region.

In one embodiment a SE compression stent (5) having a stent focal region (100) can also contain a luminal covering (155) as shown in FIGS. 9A and 9B. The luminal covering (155) is attached or bonded to the stent proximal region (105) and to the stent distal region (110) and forms a cylindrical tube across the stent focal region (100) having a luminal fabric diameter (160) or luminal covering diameter (160) that is the same as the stent non-focal region diameter (128); the luminal fabric or luminal covering (155) can extend into the proximal non-focal region (105) and distal non-focal region (110). This embodiment is released from an external sheath and expands outwards to an expanded state such that the stent non-focal region reaches a stent non-focal region diameter (128) that is similar to the native lumen diameter (35) with a small oversizing of the stent non-focal regions (152) such that they are zero to 15% larger than the native lumen diameter. The focal stent region expands outwards to a significantly larger diameter (125) that is 50% larger than the native artery diameter and 50% larger than the non-focal region diameter (128) to generate a compressive force onto the sympathetic nerves (70) within the vessel wall. The nerve fibers are blocked by either severance of the nerve fibers or via compression of the nerve fibers. The luminal fabric or luminal covering (155) can be formed from materials such as ePTFE, microporous PU (5-30 micron pore sizes), or other thin microporous materials used in vascular grafts or other implanted medical devices.

Another embodiment for a SE compression stent (5) is shown in FIGS. 10A and 10B. The proximal region and distal region of the stent are formed from SE material such as NiTi. The compression stent (5) has an outer stent focal region (165) and a luminal stent region (170); both are formed from SE materials in this embodiment. The outer stent focal region (165) is sized to be significantly larger (50% larger, range 30-100% larger) than the native lumen diameter; the luminal stent is sized such that it retains the diameter of the stent non-focal regions (152). The SE stent structure can be formed from Nitinol or other elastomeric metal, for example. Upon release of the SE compression stent (5) from the outer or external sheath (15), the compression stent (5) expands outwards such that the proximal and distal stent regions are approximately equal to the native lumen diameter. The outer focal stent expands outwards to a significantly (i.e., 50% larger, range 30-100%) larger stent focal region (100) diameter than the stent non-focal region diameter (128). The luminal stent region (170) has a luminal stent diameter (175) that is approximately equal to the native lumen diameter (35) and is equal to the stent non-focal region diameter (128). The luminal stent region (170) is attached to the proximal region and distal region of the stent and forms a cylindrical tubular stent for blood flow to pass through the lumen. The luminal region and focal region of the stent can be formed via 3D deposition methods of metal, polymer, or composite materials. Alternately, the luminal stent or focal stent can be attached to the proximal region and distal region via metal brazing, welding, or via machining methods commonly used in the formation of stent frame structures. Further alternately, the outer focal stent region can be formed separately and attached to a cylindrical stent that forms the stent proximal region (105), luminal stent region (170), and stent distal region (110); the attachment can occur via brazing, welding, suturing, use of adhesives, or other metal forming process. The proximal and distal stent regions can be formed such that they are contiguous with the focal stent region; the luminal stent region (170) can also be formed contiguously with the other stent portions.

A focal region covering (130) (see FIG. 11) can be bonded or attached to the outer focal stent region or a luminal covering (155) can be attached to the luminal stent region (170) of the compression stent (5) of FIGS. 10A and 10B. The outer focal stent covering (130) will ensure that the focal stent frame does not migrate through the vessel wall but instead applies a pressure to the sympathetic nerve fiber to cause a block in nerve conduction. The luminal stent covering (155) will provide both a cylindrical lumen for blood flow through the renal artery (10) without thrombosis at the site of the enlarged native vessel lumen (30) at the outer stent focal region (165). Also, the luminal covering (155) will prevent migration of SMC into the vessel lumen (30) resulting in stenosis of the artery (10) at the site of the focal region.

The compression stent (5) of the present invention can be formed such that the proximal region and distal region are formed from a BE material and the focal stent region is formed from a SE material as shown in FIG. 12. The BE material is a plastically deformable material such as stainless steel, polymeric materials, biodegradable materials, and other materials commonly used in BE stents including normally elastic metals such as Nitinol or other elastomeric metal which can be machined with hinge geometry that allows the stent non-focal regions (152) of the stent structure to be balloon expandable and undergo plastic deformation during expansion deformation while the stent focal regions can retain the normal elastomeric character of a standard Nitinol stent structure. The BE material can also be formed from a normally elastic material (such as Nitinol, for example) that is thermally treated such that it behaves in a plastically deformable manners. Also, the BE material can be a normally elastic material that is formed into a shape that causes its deformation to occur plastically by exceeding the elastic limit for deformation during its expansion deformation. The BE proximal stent region and BE distal stent region can be formed to be contiguous with the SE stent focal region. With thermal treatment or geometric dimensioning of the stent wall structure the compression stent (5) can obtain balloon expandable character in the stent non-focal regions (152) and self-expanding character in the stent focal regions from a single contiguous metal tube. Alternately, the proximal and distal stent regions can be welded or otherwise attached to the focal stent region. The SE material can be formed from elastically deformable materials such as Nitinol, elgiloy, and other materials commonly used in SE stents.

Figure 12C:
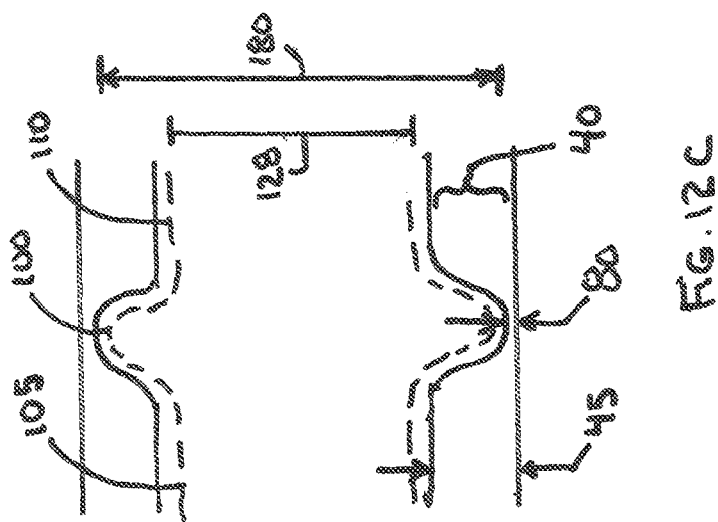
FIG. 12C is a longitudinal view of a compression stent having a self-expanding focal region and balloon expandable non-focal regions; the compression stent has been released from an external sheath and a dilation balloon has expanded the balloon-expandable regions; the stent focal region has expanded further over time.
Figure 12B:
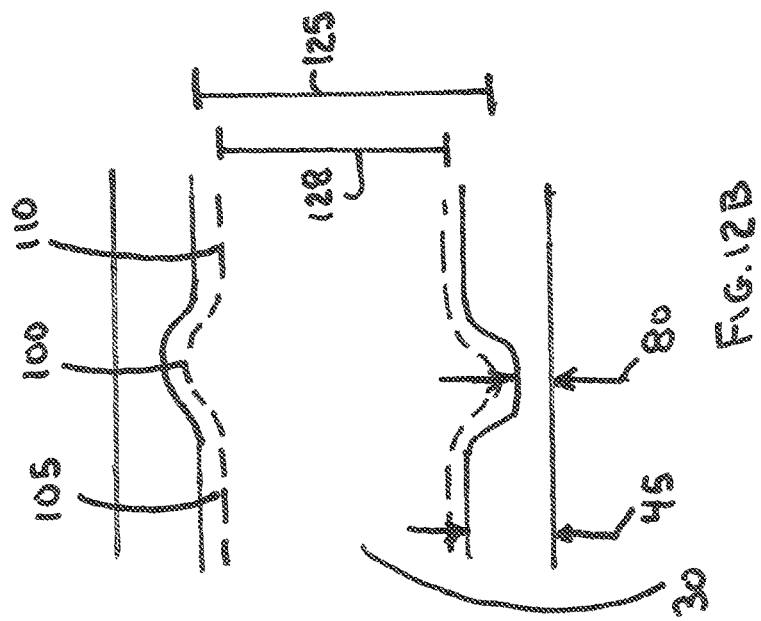
FIG. 12B is a longitudinal view of a compression stent having a self-expanding focal region and balloon expandable non-focal regions; the compression stent has been released from an external sheath and a dilation balloon has expanded the balloon-expandable regions.
Figure 12A:
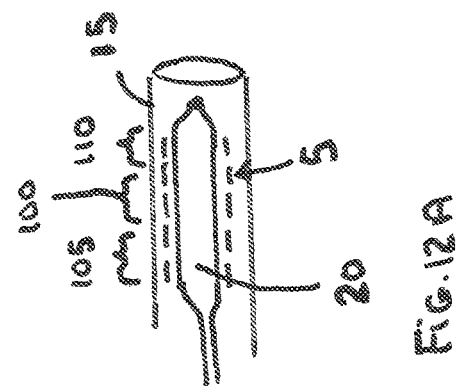
FIG. 12A is a longitudinal view of a compression stent having a self-expanding focal region and balloon expandable non-focal regions; the compression stent is mounted onto a dilation balloon and is held in an nonexpanded configuration by an external sheath.

In its non-expanded configuration as shown in FIG. 12A the compression stent (5) is mounted onto a balloon such as a cylindrical balloon or a dilation balloon (20) with a balloon focal region (135) located at the distal end of a balloon dilation catheter. An external sheath (15) holds the SE focal stent region into a small diameter configuration. Upon release from the external sheath (15) the SE stent focal region (100) can expand out from a smaller nonexpanded diameter to a larger expanded diameter while the BE stent proximal region (105) and stent distal region (110) are crimped tightly to the outside of the dilation balloon. Following expansion of the dilation balloon (20) as shown in FIG. 12B, the SE stent focal region (100) expands outward to its expanded state achieving a stent focal region diameter (125) and causing the vessel wall to compress from larger native wall thickness to a compressed wall thickness; the stent proximal region (105) and stent distal region (110) expand outwards to an expanded state with a larger stent non-focal region diameter (128). Over a time period ranging from minutes to days the stent focal region (100) can expand further to a fully expanded focal region diameter (180) representative of its equilibrium diameter as shown in FIG. 12C. The nerves (70) located within the vessel wall adjacent the focal region are compressed to cause a block in their conduction. The block is due to either a severance of the nerve fiber by the stent frame in the focal region or a compression of the nerve fiber caused by compressive pressure imposed by the focal region. The dilation balloon (20) serves to hold the compression stent (5) in its proper location within the blood vessel while the stent focal region (100) has expanded outwards. The dilation balloon (20) further can serve to provide a post dilation of the stent focal region (100) to effect a more immediate nerve blockage within minutes after implantation. The BE stent proximal region (105) and BE stent distal region (110) are not dilating the native blood vessel significantly (i.e., zero to 15% stent non-focal region diameter (128) oversizing) and hence are nonthrombogenic and are not significantly affecting the vessel native wall thickness.

Figure 13C:
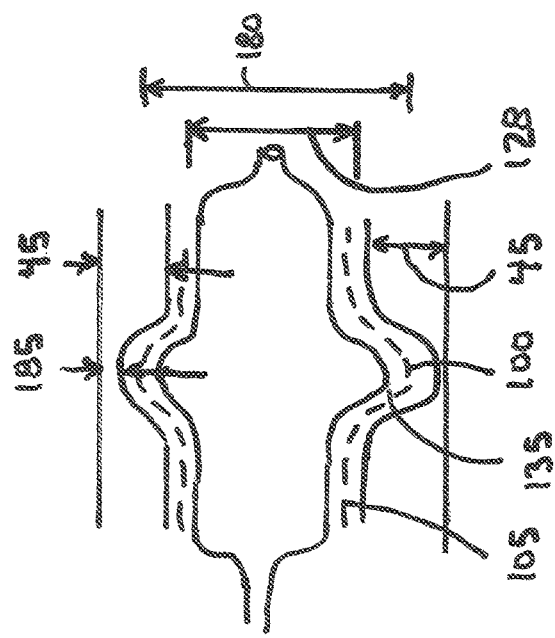
FIG. 13C is a longitudinal view of a compression stent having a self-expanding focal region and balloon expandable non-focal regions; the compression stent has been released from an external sheath and a dilation balloon having a balloon focal region has expanded the balloon-expandable regions and further expanded the self-expanding region causing compression of the blood vessel wall.
Figure 13B:
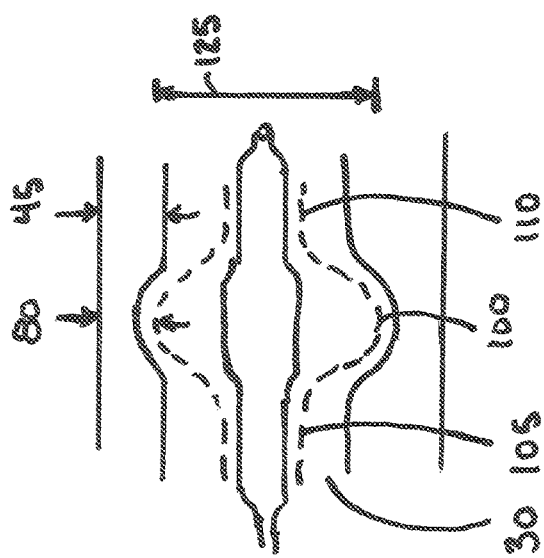
FIG. 13B is a longitudinal view of a compression stent having a self-expanding focal region and balloon expandable non-focal regions; the compression stent has been released from an external sheath but still has the balloon expandable regions mounted onto a dilation balloon; the stent focal region has expanded outwards.
Figure 13A:
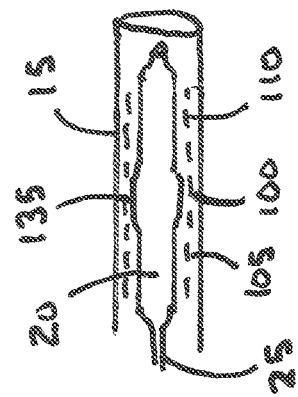
FIG. 13A is a longitudinal view of a compression stent having a self-expanding focal region and balloon expandable non-focal regions; the compression stent is mounted onto a dilation balloon having a balloon focal region and the compression stent is held in an nonexpanded configuration by an external sheath.
Figure 13D:
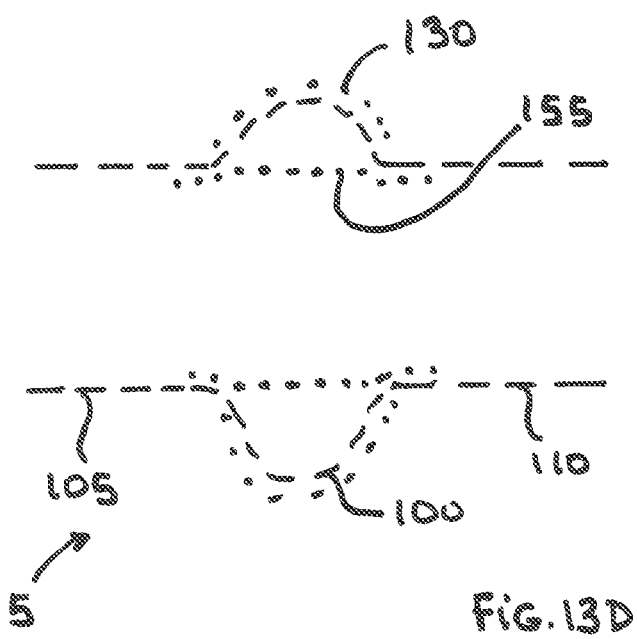
FIG. 13D is a longitudinal view of a compression stent having a self-expanding focal region and balloon expandable non-focal regions; the compression stent has been released from an external sheath and a dilation balloon having a balloon focal region has expanded the balloon-expandable regions and further expanded the self-expanding region; a luminal covering prevents cellular hyperplasia into the lumen.

The compression stent (5) described in the previous embodiment of FIGS. 12A-12C can be mounted onto a dilation balloon (20) that has a balloon focal region (135) as shown in FIGS. 13A-13C. Following release from the external sheath (15) the SE stent focal region (100) will expand outwards to a stent focal region diameter (125) that is significantly larger than the native lumen diameter (35) and the compression stent (5) is held onto the balloon of the balloon dilation catheter (25) via the BE stent proximal region (105) and BE stent distal region (110) of the compression stent (5) as shown in FIG. 13B. Upon expansion of the dilation balloon (20) as shown in FIG. 13C, the focal stent region is pushed outwards into the vessel wall to an even larger fully expanded stent focal region diameter (180) causing even greater compression of the sympathetic nerves (70) found in the vessel wall. The operator is able to identify immediately that the nerve conduction has been blocked. Further expansion of the focal stent region over time may also occur due to remaining expansion forces found in the SE focal region of the stent thereby cause even greater blockage of nerve conduction due to a fully compressed wall thickness (185). The BE stent proximal region (105) and stent distal region (110) are expanded into contact with the vessel wall and have a stent non-focal region diameter (128)

that is approximately equal to the native lumen diameter (35) and is significantly smaller than the stent focal region diameter. The compression stent (5) of this embodiment can also contain a focal covering and/or a luminal covering (155) as shown in FIG. 13D. The focal covering can be a thin microporous polymeric material that is attached to the focal region of the stent. The luminal covering (155) can be a thin microporous elastomeric material such as a electrostatically spun PU, a microporous silicone, a composite material or other microporous material that can stretch due to the enlargement of the focal region of the balloon and rebound back to match the native lumen diameter (35) and the stent non-focal region diameter (128). The luminal fabric or luminal covering (155) is attached to both the stent proximal region (105) and stent distal region (110) via adhesive bonding, or cohesive bonds between the polymeric material of the covering (90) and the stent frame material. The luminal fabric or covering can extend into the stent proximal region and into the stent distal region by 3 mm (range 1-10 mm) to ensure that cellular hyperplasic does not result in stenosis of the arterial lumen. The luminal covering can alternately extend throughout the entire non-focal stent regions.

Figure 14C:
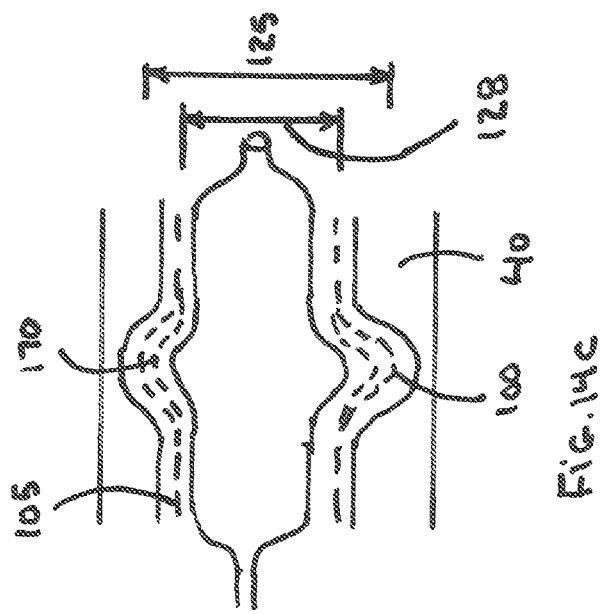
FIG. 14C is a longitudinal view of a compression stent having a self-expanding focal region and balloon expandable non-focal regions; the focal region has a stent focal region and a luminal stent; the compression stent has been released from an external sheath and a dilation balloon having a balloon focal region has expanded the balloon-expandable regions and further expanded the self-expanding region causing compression of the blood vessel wall.
Figure 14B:
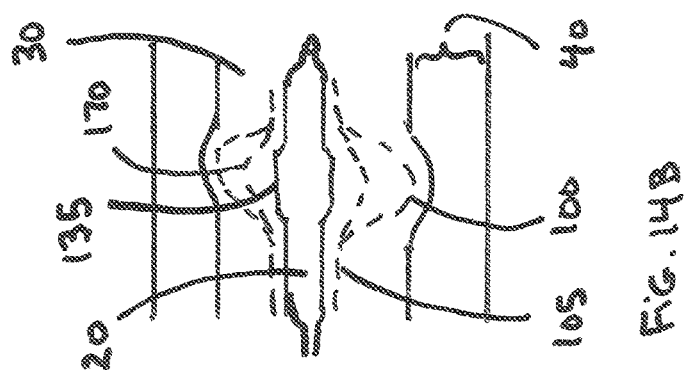
FIG. 14B is a longitudinal view of a compression stent having a self-expanding focal region and balloon expandable non-focal regions; the focal region has a stent focal region and a luminal stent; the compression stent has been released from an external sheath but still has the balloon expandable regions mounted onto a dilation balloon; the stent focal region has expanded outwards.
Figure 14A:
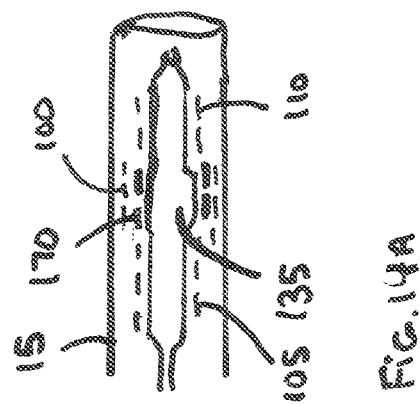
FIG. 14A is a longitudinal view of a compression stent having a self-expanding focal region and balloon expandable non-focal regions; the focal region has a stent focal region and a luminal stent; the compression stent is mounted onto a dilation balloon having a balloon focal region and the compression stent is held in an nonexpanded configuration by an external sheath.
Figure 14D:
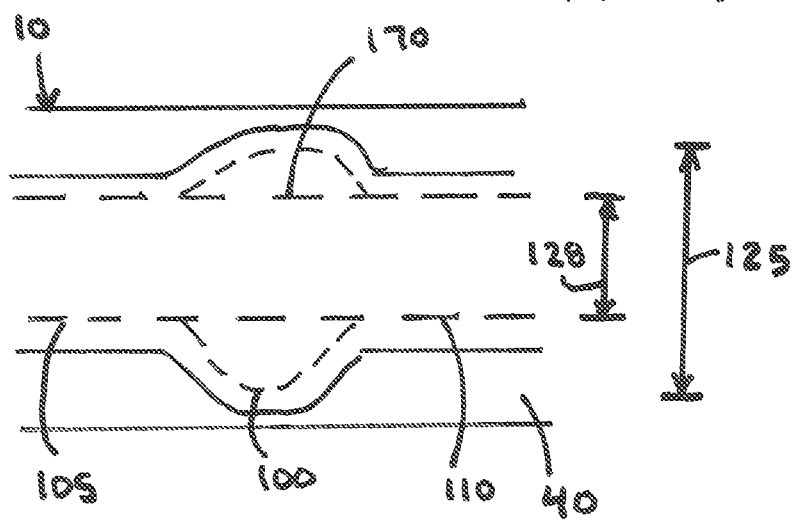
FIG. 14D is a longitudinal view of a compression stent in an expanded configuration; the focal stent region has a focal covering, the luminal stent has a luminal covering.
Figure 14E:
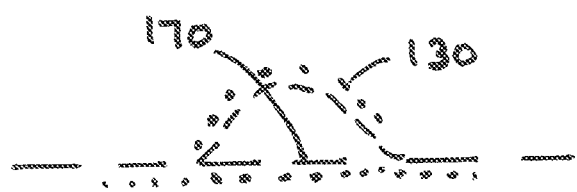
FIG. 14E is a longitudinal view of a compression stent having a luminal stent with a luminal covering and a stent focal region with a focal covering.

Another embodiment for the compression stent (5) has a BE proximal stent region and BE distal stent region and has a SE focal stent region; a SE luminal stent region (170) is also located adjacent to the focal stent region. The luminal stent can be either welded or bonded to the other regions of the compression stent, or alternately, the luminal stent can be formed contiguously with the other stent regions via 3D machining methods or other machining methods. The compression stent (5) of this embodiment is shown in FIGS. 14A-14C. In FIG. 14A the compression stent (5) is shown loaded onto a balloon having a balloon focal region (135) that is located adjacent the luminal stent region (170). An external sheath (15) holds the SE stent focal region (100) and SE luminal stent region (170) into its smaller diameter configuration. Upon release from the balloon, as shown in FIG. 14B, the SE stent focal region (100) and SE luminal stent region (170) expand outwards to a larger diameter than its smaller delivery configuration diameter. Expansion of the dilation balloon (20), as shown in FIG. 14C causes the BE proximal and BE distal stent regions to expand to a stent non-focal region diameter (128) that is approximately equal (i.e., the non-focal stent region can be zero to 15% larger than the native lumen diameter) to that of the native lumen diameter. The stent focal region (100) and luminal stent region (170) extend outwards to a significantly (i.e., 50% larger, range 30-100% larger) larger stent focal region diameter. Upon deflation and withdrawal of the dilation balloon (20) as shown in FIG. 14D the luminal stent region (170) returns to its luminal stent diameter (175) that is equal to the stent non-focal region diameter (128). The focal stent region will compress the sympathetic nerve fibers and result in nerve block. A focal region covering (130) can be located on the focal stent region and/or a luminal covering (155) can be attached to the luminal stent region (170) as shown in FIG. 14E. The focal covering will cause the focal stent region to apply a pressure to the sympathetic nerve that results in conduction block.

Figure 15C:
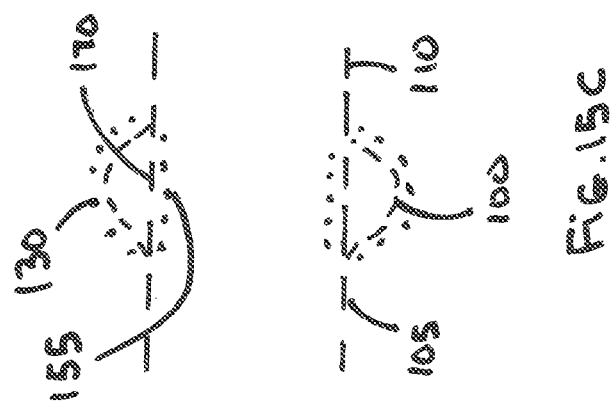
FIG. 15C is a compression stent having a balloon expandable focal region and non-focal regions; the compression stent has a self-expanding luminal stent; the compression stent is in an expanded configuration; a covering is located on the stent focal region and the luminal stent.
Figure 15B:
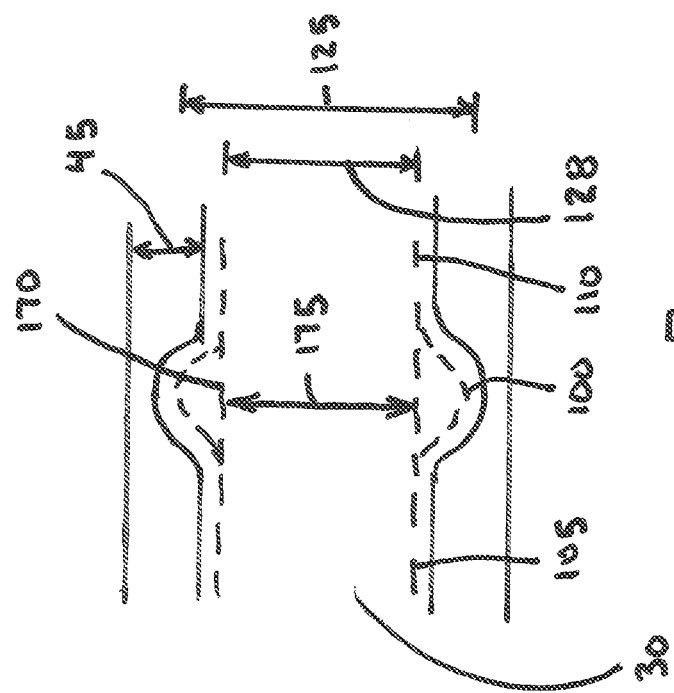
FIG. 15B is a compression stent having a balloon expandable focal region and non-focal regions; the compression stent has a self-expanding luminal stent; the compression stent is in an expanded configuration.
Figure 15A:
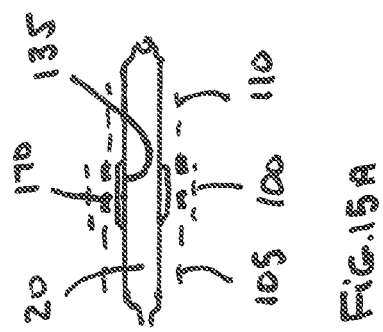
FIG. 15A is a compression stent having a balloon expandable focal region and non-focal regions; the compression stent is mounted onto a dilation balloon having a balloon focal region.

Yet another embodiment for the compression stent (5) has a BE proximal stent region and distal stent region. This embodiment has a BE focal stent region; a SE luminal stent region (170) is located adjacent to the BE focal stent region (100); the stent regions can be formed contiguously or can be joined via various metal joining process methods. The compression stent (5) of this embodiment is shown in FIGS. 15A-15C. In FIG. 15A the compression stent (5) is shown loaded onto a dilation balloon (20) having a balloon focal region (135) that is located adjacent the luminal stent (170). An external sheath (15) may be utilized if necessary to hold the BE focal stent and underlying SE luminal stent region (170) into its smaller diameter configuration. Upon release from the sheath (15), expansion from the balloon, and deflation and removal of the balloon, as shown in FIG. 15B, the BE stent focal region (100) is retained outwards at a larger stent focal region diameter (125) while the SE luminal stent region (170) is returned to its equilibrium luminal stent diameter (175) that is approximately equal to the native vessel diameter and equal to the stent non-focal region diameter (128). The BE proximal and BE distal stent regions have also expanded to the stent non-focal region diameter (128) that is equal to that of the native vessel. The BE focal stent region will compress the sympathetic nerve fibers and result in nerve block via either severance of the nerve fiber or via compression of the nerve fiber. A focal region covering (130) can be located on the stent focal region (100) and/or a luminal fabric or luminal covering (155) can be located on the luminal stent region (170) as shown in FIG. 15C. The focal region covering (130) will cause the focal stent region to apply a pressure to the sympathetic nerve that results in conduction block rather than severing the nerve fiber. The luminal fabric or luminal covering (155) will assist in reducing thrombosis of the native vessel and will prevent migration of SMC into the vessel lumen (30) resulting in vessel stenosis. Alternate embodiments for the compressive stent are contemplated. For example, the luminal stent region (170) of this embodiment can be omitted; alternately the proximal stent region and distal stent region can be formed from a SE material and the focal stent region can be formed from a BE material; such embodiments are anticipated and are included in the present invention.

One or more drugs can be used with any of the embodiments of the present invention to improve their function including reducing thrombosis of the native vessel, reducing restenosis of the native vessel, or improving the ability of the compression device of the present invention to block sympathetic nerve conduction. Drugs can be placed onto the focal region of the stent, the proximal or distal regions of the stent, the luminal stent, the focal covering, or the luminal fabric or luminal covering (155), or any covering (90) located on the stent. Drugs such as Taxol or Sirolimus can be used to reduce cellular SMC proliferation that can lead to vessel stenosis. Anti-thrombotic drugs located on the present invention can reduce thrombosis and enhance patency of the native renal artery (10). Other drugs including such as nerve blocking agents can be applied to any portion of the present invention to assist in causing sympathetic nerve necrosis and reduction of nerve conduction.

The compression stent (5) of the present invention can be formed from a material that allows the stent frame to increase in temperature noninvasively by application of an external energy source including RF, US, focused US, microwave, other electromagnetic energy form, magnetic coupling, IR light, UV light or other energy forms. Energy can be delivered to the compression stent (5) of the present invention via noninvasive coupling and result in sympathetic nerve fiber blockage. The present compression stent (5) is understood to include such designs that contain coils or other coupling means that couple with an external energy sources that are applied noninvasively.

Figure 23C:
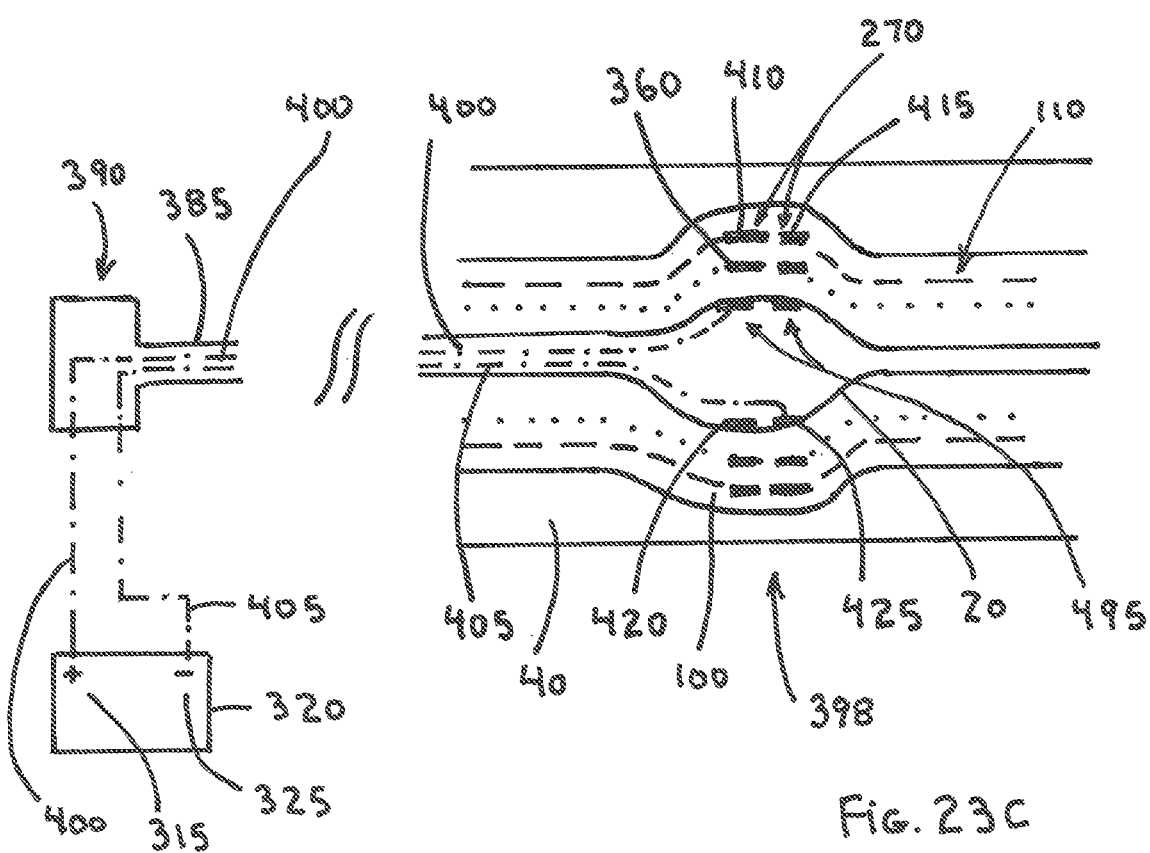
FIG. 23C is a plan view of compression stent having bipolar electrodes and having a conduction wire that delivers radiofrequency energy from the radiofrequency generator through the delivery catheter shaft to the dilation balloon for transmission to the electrodes located on the compression stent focal region.
Figure 23D:
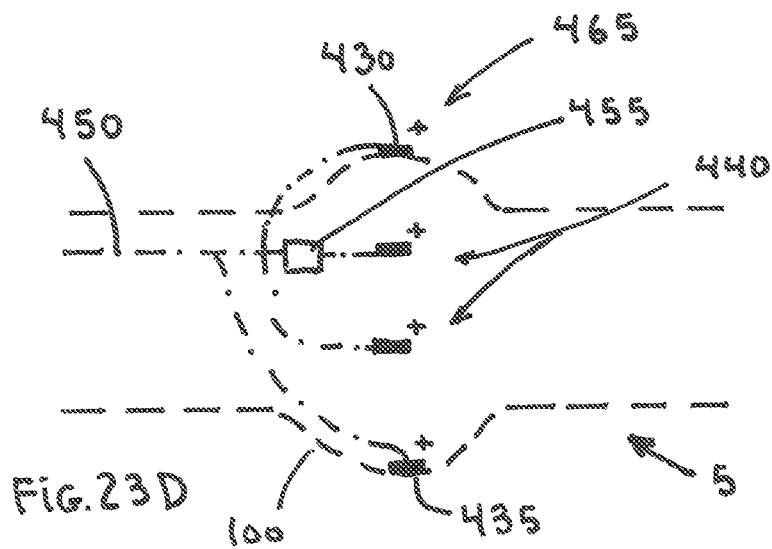
FIG. 23D shows a configuration of individual unipolar electrodes located along a perimeter of the focal region of the compression stent and a digital control for power to the electrodes located on or near the compression stent.

A miniaturized circuit such as the micro circuit (455) shown in FIG. 23D, for example, can be located within the stent frame structure (95) of the compression stent (5) that is able to determine if a sympathetic nerve signal is being transmitted across the focal region of the stent or across two focal regions of the compression stent, for example. The miniaturized circuit is initially used during implant of the compression stent (5) to determine if the sympathetic nerve signal is being transmitted across the focal region. If the nerve signal is blocked, then the operator knows that the procedure is completed. If conduction across one or more focal regions of the stent is found then further adjustment of the stent can be performed in the interventional suite. The stent can be examined non-invasively after a period of time to correlate the clinical results with the procedural result. Further dilation of the compression stent (5) can be performed using noninvasive energy coupling to the stent.

In an alternate embodiment a compression stent assembly (186) (see FIGS. 16-19C, for example) can be formed from two separate stented members that are placed subsequently into the artery to cause blockage of the nerve signal. The first stented component (188) can be a self-expanding (SE) compression stent component (190) without a compression covering (195) or a SE compression stent with a compression covering (195) as shown in FIG. 16. The compression covering (195) is of a similar material to that previously described for a covering (90) and serves as a barrier for cellular penetration through the wall structure of the stent to reduce or prevent the stent from migrating through the vessel wall (40) and thereby allowing the stent to compress the vessel wall (40) and nerve (70); the compression covering (195) can be formed from a thin film of ePTFE, polyurethane, or other polymer, for example. The SE compression stent component (190) can be held within an external sheath (15) as shown in FIG. 16 during delivery of the stented member through the vasculature to a site within the renal artery, for example. Upon release of the SE compression stent component (190) from the external sheath (15), the SE compression stent component (190) expands outwards to a first stent component diameter (202) that is 50% larger (i.e., reaches a stent equilibrium diameter that ranges from 30-100% larger) than the unexpanded artery native luminal diameter (35) (or the stent end region diameter) to compress the vessel wall (40) and nerve (70) and causing blockage of nerve signal transmission as shown in FIG. 17. It is noted that the collagen fibers located in the adventitial layer (65) will become fully aligned with the circumferential direction when the vessel has been expanded to an expanded lumen diameter (75) that is 80% larger than the normal native arterial diameter (i.e., the native vessel undergoes an expansion ratio of 1.8 times the initial vessel luminal diameter. The SE compression stent component (190) can be any SE stent design with closed or open cell stent pattern that is similar to current vascular stent designs used for vascular stenting. The SE compression stent length (200) can be approximately equal to the unexpanded luminal diameter of the native artery into which it is being delivered (range 20% to 200% of the unexpanded native vessel luminal diameter). A SE compression stent length (200) that is less than 20% of the native vessel diameter may have a tendency to generate misalignment of the stent central axis with the native vessel central axis. A SE compression stent length (200) greater than 200% of the native vessel diameter causes a greater risk for native vessel trauma and resultant intimal hyperplasia and thrombosis. The SE compression stent component (190) can be post dilated with a dilation balloon (20) to provide acute expansion of the SE compression stent and acute blockage of the nerve signal transmission. Further growth in stent diameter can occur over minutes, hours, and days to a stent equilibrium diameter to further ensure that nerve blockage is maintained and further generated.

Figure 18:
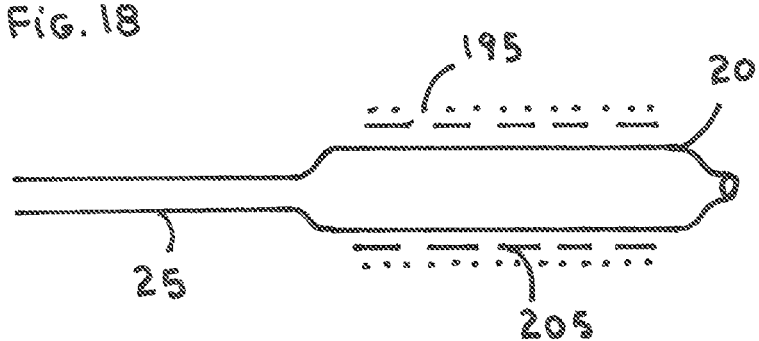
FIG. 18 is a plan view of a balloon expandable compression stent that is positioned onto the outside surface of a dilation balloon.

The first stent component (188) of a compression stent assembly (186) (see FIG. 19B, for example) can alternately be a BE compression stent component (205) without a compression covering (195), or a BE compression stent component (205) with a compression covering (195) as shown in FIG. 18. The BE compression stent component (205) is mounted onto the dilation balloon (20) of a dilation balloon catheter (25) for delivery to the site of artery that is intended for blockage of the nerve signal. Upon dilation of the BE compression stent component (205), the vessel wall (40) is compressed as shown in FIG. 17, causing blockage of nerve signal transmission in a manner similar to the signal blockage caused by a SE compression stent component (190). The first stent component (188) can reach a first stent component diameter (202) that is 50% larger (range 30-100% larger) than the native lumen diameter (35).

Figure 19A:
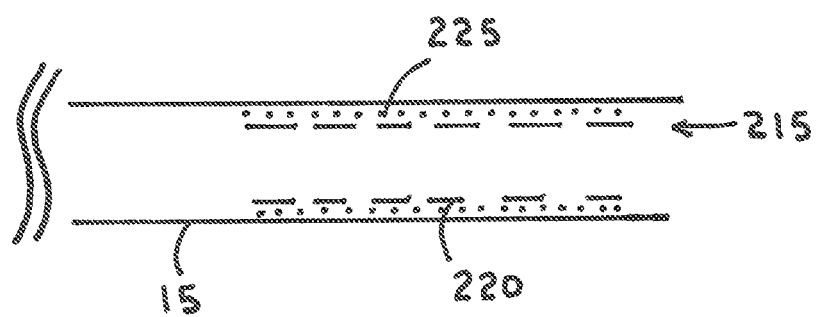
FIG. 19A is a plan view of a blocking stent with a covering that can be used as a second component to block the hyperplastic ingrow of cells into the lumen of a blood vessel.

The second stent component (210) (see FIG. 19A) of the compression stent assembly (186) is a blocking stent (215). The blocking stent (215) can be a SE blocking stent (220) as shown in FIG. 19A; the SE blocking stent (220) is contained within an external sheath (15) during its delivery through the vasculature to a location that extends within the first component lumen (222) of first stent component (188) that has already been delivered to the native vessel; the SE blocking stent (220) extends for a distance of a few millimeters (i.e., range 3-10 mm) beyond each end of the first stent component (188) as shown in FIG. 19B. The blocking stent (215) has a blocking covering (225) along its length that serves to form a uniform constant diameter that is equal to the unexpanded native lumen diameter (35) of the native artery. The blocking covering (225) prevents thrombosis from occurring due to the enlarged diameter formed by the first stent component (188). The blocking covering (225) also prevents cellular migration such as smooth muscle cell proliferation and migration into the vessel lumen (30). The blocking stent (215) has a blocking stent diameter (230) that is equal to the unexpanded native lumen diameter (35) and has a blocking stent length (235) that is 6 mm longer than the first stent component length (245) (range 4-20 mm longer than the first stent component length (245) extending at least 3 mm beyond each end of the first stent component (188). The blocking stent (215) along with the blocking covering (225) ensures that intimal hyperplasia cannot extend into the lumen of the blocking stent (215); intimal hyperplasia can provide resistance to blood flow in the native artery. The blocking covering (225) is formed from a polymeric film such as ePTFE, polyurethane, or other polymeric material as described earlier for the covering (90).

The blocking stent (215) can alternately be a BE blocking stent (240) as shown in FIG. 19C; the BE blocking stent (240) is crimped onto the outside of a dilation balloon (20) of a dilation catheter (25) for delivery through the vasculature to a site within the first stent component lumen (222). The BE blocking stent (240) has a blocking stent length (235) that is a few millimeters longer than the first stent component length (245) (range 4-20 mm longer than the first component length (245)), and has a diameter that is similar to the unexpanded native vessel luminal diameter. The BE blocking stent (240) has a blocking covering (225) attached throughout its length or a portion of its length and extending for 3 mm both proximal and distal to the first stent component (188) to serve to prevent thrombosis and intimal hyperplasia within the lumen of the blocking stent (215) similar to that described for the SE blocking stent (220).

The blocking stent length (235) can be 15 mm in axial length (range 10 mm-25 mm) since it is present to block intimal hyperplasia caused by the expansion of the first stent component and is not intended to provide vessel stenting as performed for normal angioplasty in a diseased artery; the short length will allow healing via a pannus ingrowth from each end of the blocking stent to form an endothelial layer throughout the blocking stent that will ensure patency of the covered stent. Similarly for all of the embodiments of the compression stent presented in this specification, the axial length from the proximal end to the distal end of the compression stent is also 15 mm (range 10-25 mm), with a preferred length of 15-20 mm. The axial length of the compression stent includes the additive sum of lengths for the non-focal regions and the focal region. A pannus ingrow from each end of the compression stent of approximately 10 mm will cause the compression stent of the present invention to become endothelialized throughout its length.

Figure 20A:
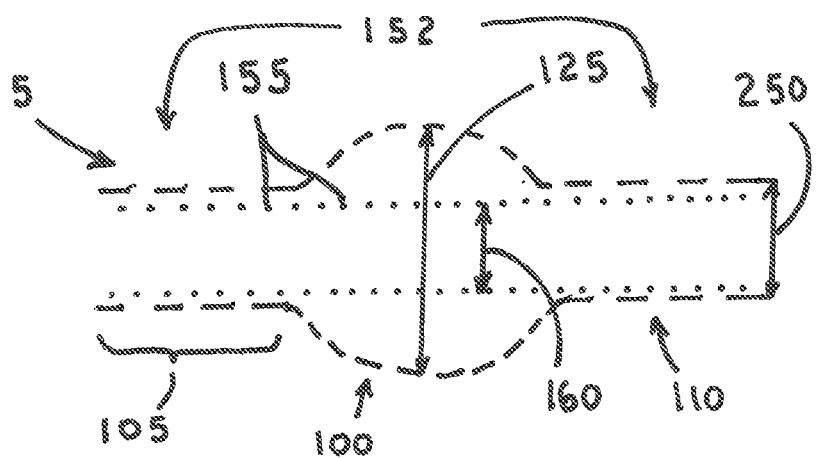
FIG. 20A shows a self-expanding compression stent in its equilibrium expanded configuration.

One embodiment of the compression stent (5) of the present invention is shown in FIGS. 20A-20E. In FIG. 20A the compression stent (5) is shown in a freely expanded configuration unconstrained in free space. The stent distal region (110) and stent proximal region (105) have a stent equilibrium end diameter (250) in an unconstrained configuration that is moderately larger by 15% (range 0-25% larger) than the native vessel lumen diameter (35) but does not apply enough outward force (345) to enlarge the native artery more than approximately 15% from the native vessel lumen diameter (35). The stent focal region (100), located between the stent proximal region (105) and stent distal region (110) (i.e., together referred to as the stent end regions (152) or stent non-focal region diameter (152) since they are of approximately the same diameter) has an stent focal region diameter (125) or stent focal region equilibrium diameter (125) in free space that is 50% larger (range 30-100% larger) than the diameter of the stent end region diameter (250) and the native vessel lumen diameter (35). Attached to the compression stent (5) along the stent proximal region (105) and stent distal region (110) is a luminal covering (155); the luminal covering (155) extends contiguously from at least a portion of the stent proximal region (105), across the stent focal region (100), and across at least a portion of the stent distal region (110). The luminal covering (155) is not attached to the stent frame (i.e., the metallic or polymeric stent structure of the compression stent (5) in the stent focal region (100); the luminal covering (155) in the focal region has a luminal covering equilibrium diameter (160) in an unconstrained configuration that is approximately equal to the native lumen diameter (35). The stent frame is formed from a resilient material used in the construction of vascular stents; such materials include Nitinol and other elastic metals, biodegradable materials such as various chemical forms of polyglycolic acid, polylactic acid and other biodegradable materials, and other materials used in the construction of vascular stents. The luminal covering (155) can be formed from an elastic material such as a porous polyurethane, porous silicone, or other porous resilient material. The luminal covering (155) can be formed via electrostatic spinning, salt leaching process, a chemical extraction process, or other process that leaves the luminal covering (155) with a pore structure that can heal over time in a manner similar to typical vascular graft materials. The luminal covering (155) is formed such that it can stretch out to a large diameter of at least twice the diameter of the native artery and return to a smaller luminal covering equilibrium diameter (160) that is equal to the luminal diameter of the native artery or equal to the stent end region diameter (250).

Figure 20B:
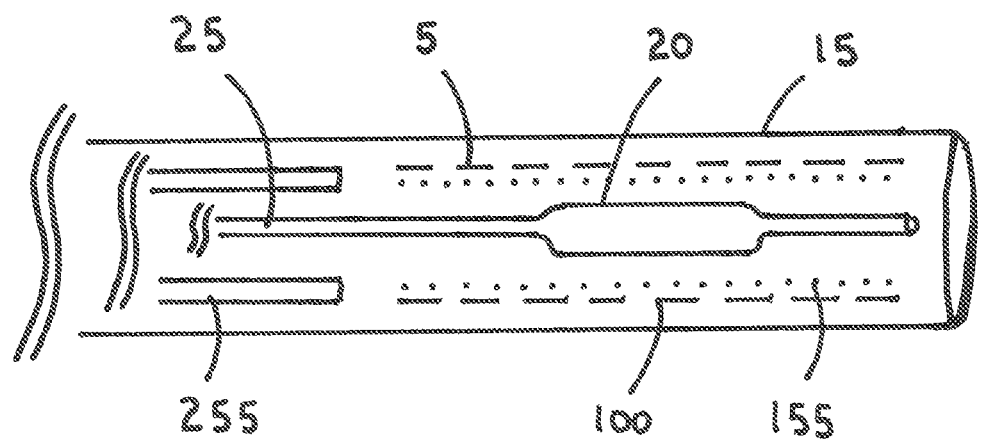
FIG. 20B shows a self-expanding compression stent loaded with its focal region adjacent to a dilation balloon and contained within a delivery sheath for delivery to the blood vessel.

The compression stent (5) is formed from a SE material that is held by an external sheath (15) as shown in FIG. 20B for delivery to the anticipated site for arterial wall compression and ablation of the renal nerves (70), for example, located in the vessel wall (40) of the renal artery, for example. The compression stent (5) is mounted onto a dilation balloon (20) such that the compression stent focal region (100) is adjacent to and located to the outside in a radial direction from the dilation balloon (20). A pusher member (255) is used to ensure that the compression stent (5) is positioned onto or radially adjacent to the dilation balloon (20) during delivery and to assist with expelling the compression stent (5) from the external sheath (15) at the site of the arterial wall compression. The pusher member (255) moves relative to the external sheath (15) and is in contact with the compression stent (5) to hold the compression stent (5) in position while the external sheath (15) is removed by retraction in a proximal direction to expel the compression stent (5) from the external sheath (15) at the site for arterial wall nerve (70) ablation.

Figure 20C:
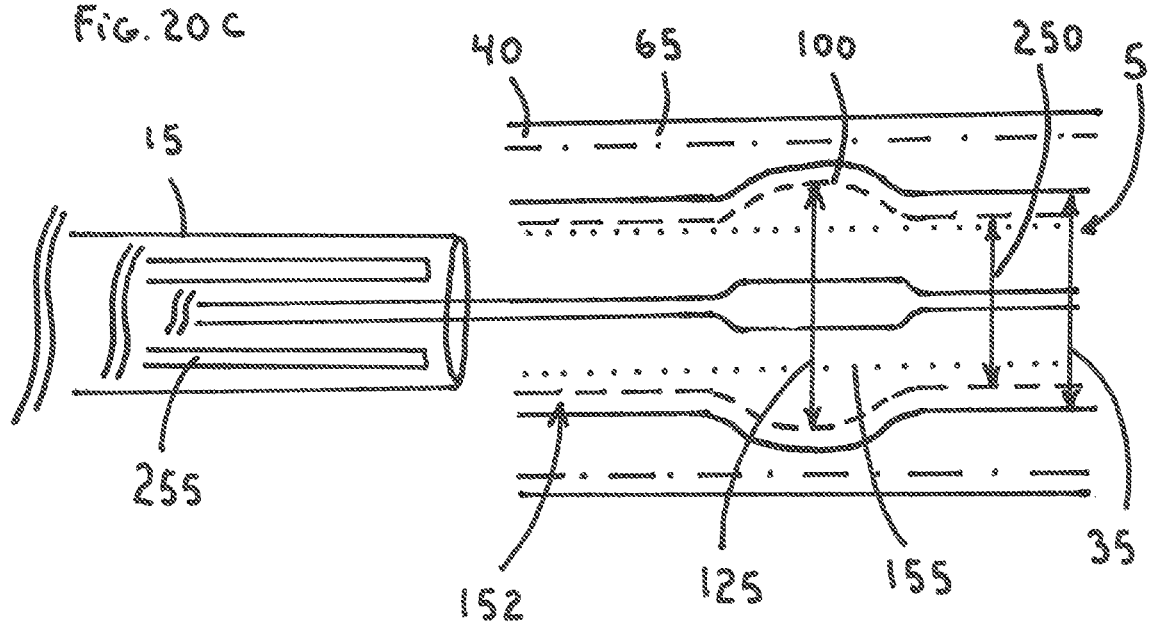
FIG. 20C shows the release of the self-expanding compression stent from the delivery sheath prior to inflation of the dilation balloon.
Figure 20D:
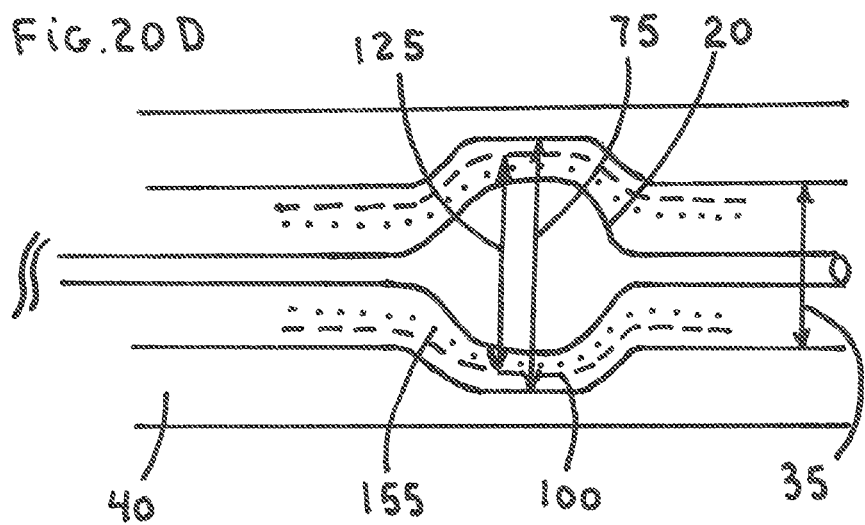
FIG. 20D shows the self-expanding compression stent being expanded outwards further against the vessel wall via inflation of a dilation balloon.

As shown in FIG. 20C the external sheath (15) has been withdrawn while retaining the position of the pusher member (255) and the dilation balloon (20); the compression stent (5) has expanded outwards to contact (or slightly expand) the native vessel wall (40) in the stent proximal region (105) and stent distal region (110); the stent focal region (100) of the compression stent (5) has expanded the native artery to a stent focal region diameter (125) by 50% (range from 30-100%) diametric enlargement greater than the native vessel lumen diameter (35). Upon inflation of the dilation balloon (20) to a diameter of 30-100% enlargement greater than the native vessel luminal diameter as shown in FIG. 20D, the stent focal region (100) is ensured an enlargement to a stent focal region diameter (125) of 50% (range 30% to over 100% diametric enlargement). The adventitial layer (65) of the vessel wall (40) contains collagen fibers that become aligned and will allow very little further enlargement of the arterial diameter beyond 80% enlargement (i.e., an expansion diameter ratio of 1.8 expansion ratio equals: stent focal region diameter (125)/stent end region diameter (250)). Thus an enlargement of the stent focal region (100) by a factor of 1.8 (i.e., 80% enlargement) to a stent focal region diameter (125) by 180% (range: factor of 1.5 to over 2.0) will ensure that the renal nerves (70) located within the arterial wall will become compressed and will no longer continue to transmit nerve signals. Inflation of the dilation balloon (20) to an expansion ratio of 1.8 (expansion ratio equals: expanded vessel lumen diameter (75)/normal unexpanded native vessel lumen diameter (35)) will ensure that an acute compression of the nerve (70) is obtained such that the operator can identify an acute blockage of the nerve signal. Since the stent focal region (100) is formed from a SE material (such as Nitinol, for example), the focal region can continue to grow after deflation of the dilation balloon (20) by an additional 10-20% over time to reach the stent focal region equilibrium diameter (from 50% to over 100% larger than the native vessel lumen diameter (35) and the stent end region diameter (250)) to ensure that the nerve signal does not reestablish conduction.

As shown in FIG. 20E, the deflated dilation balloon (265) is located adjacent to the stent focal region (100) which may recoil acutely a small amount (10-20%) due to the overdistention of the arterial diameter; over time, however, the stent focal region (100) can grow from a stent focal region diameter (125) to its stent focal region equilibrium diameter and result in further enlargement of the arterial lumen and compression of the compressed vessel wall (40) to a fully compressed wall thickness (185); the stent focal region (100) can also migrate through the tissues of the arterial wall potentially severing the renal nerves (70) and blocking nerve signal conduction. Migration of the stent focal region (100) though the arterial wall can be prevented by placing a stent focal covering (260) over the outside of the stent focal region (100) as described earlier in other embodiments; in the case where a stent focal covering (260) is located on the stent focal region (100) (with the covering (90) attached to and following the shape of the enlarged stent focal region (100)) the arterial wall compression is responsible for contributing to the nerve block for signal transmission through the renal nerves (70) rather than severing the nerves (70). It is further noted that the compression stent (5) can be formed from a BE stent proximal region (105) and a BE stent distal region (110) (rather than SE regions) as described in earlier embodiments. The compression stent (5) of the present invention can also be formed from a biodegradable material such as various forms of polylactic acid, polyglycolic acid, for example, and other biodegradable materials used to form vascular stents.

Embodiments of the compression stent (5) can contain unipolar or bipolar radiofrequency (RF) electrodes located on the device. Once the renal artery vessel wall (40), for example, has been compressed, RF energy can be applied to the vessel wall (40) to ablate afferent and efferent nerves (70) that traverse through the arterial vessel wall (40). Even though the discussion found in the present specification is directed towards the use of RF electrodes and application of RF energy, it is understood that the electrodes could be microwave electrodes and the energy could be microwave energy, the electrodes could be ultrasound transducers and the energy could be ultrasound energy. Also, the application of ablative agents injected into the vessel wall (40) can be performed prior to, during, or after the vessel wall (40) has been compressed to provide an enhanced distribution of ablative chemicals (such as alcohol, for example) to the nerves (70) located within the arterial vessel wall (40). The present invention of compressing the vessel wall (40) can also be combined with application of resistive heating or other heating elements that will function better if the arterial wall thickness (45) has been reduced by application of compression during the heating or ablative treatment. The compression of the vessel wall (40) will also serve to reduce areas of thermal sinking such as those created by veins and arterioles located within the vessel wall (40) and veins located near the renal artery.

Figure 21B:
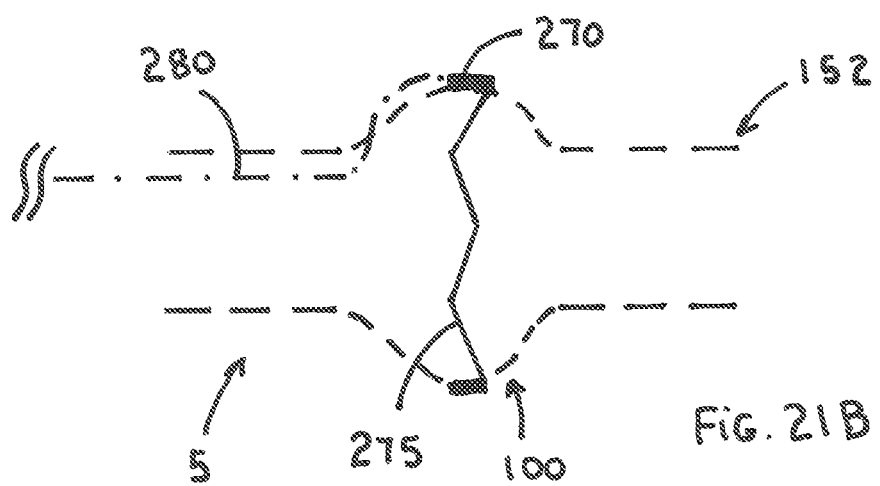
FIG. 21B shows an expandable electrode located on the surface of the stent focal region.

FIGS. 21A-21D shown an embodiment of a compression stent (5) that is used in combination with RF energy, for example, to enhance the consistent ablation of nerves (70) located in the arterial vessel wall (40). The compression stent (5) is formed from a SE material and has a stent focal region (100) that has a 30-100% larger stent focal region diameter (125) or stent focal region equilibrium diameter (125) than a stent proximal region diameter (115) or a stent distal region diameter (herein also referred to as the stent end region (152) since both stent end regions (152) are of approximately the same diameter as the stent proximal region (105) and the stent distal region (110)) as described earlier in the embodiment of FIGS. 20A-20D. Located in stent focal region (100) is a stent electrode (270). The stent electrode (270) can be formed as a zig-zag stent element (275) as shown in FIG. 21B. The stent electrode (270) is attached to a stent conduction wire (280) that extends with electrical insulation surrounding it to a conduction wire interface (285) which makes electrical connection between a conduction wire interface (285) with a pusher interface (290) as shown in FIG. 21A. Having a single unipolar zig-zag electrode can result in localized vessel ablation along a perimeter of the blood vessel due to the RF (or other forms of energy) energy that can lead to vessel stenosis found in standard prior art devices. However, the presence of the compression stent (5) with a covering (90) attached of the present invention will serve to prevent vessel narrowing and will prevent migration of smooth muscle cells (SMC) into the lumen of the native vessel.

A pusher conduction wire (295) extends from the pusher interface (290) along the pusher member shaft (300) to a pusher manifold (305) located at the pusher proximal end (310); the pusher conduction wire (295) makes electrical contact with a first pole (315) of an RF generator (320) that generates an RF signal that is transmitted to the stent electrode (270) located around the perimeter of the stent focal region (100). The opposing pole (325) or second pole (325) of the RF generator (320) is attached to an opposing electrode (330) (of opposite polarity) that is located with electrical contact with the skin of patient that is to be treated; the location can be on the patient's back, his groin, or other convenient location for locating the opposing electrode for completing the circuit path for current flow from the stent electrode (270) which is in contact with the arterial vessel wall (40) to the opposing electrode. The pusher interface (290) with the conduction wire interface (285) can be slidingly separated and the pusher removed or separated from the compression stent (5) after delivery of RF energy to the vessel wall (40).

Figure 21C:
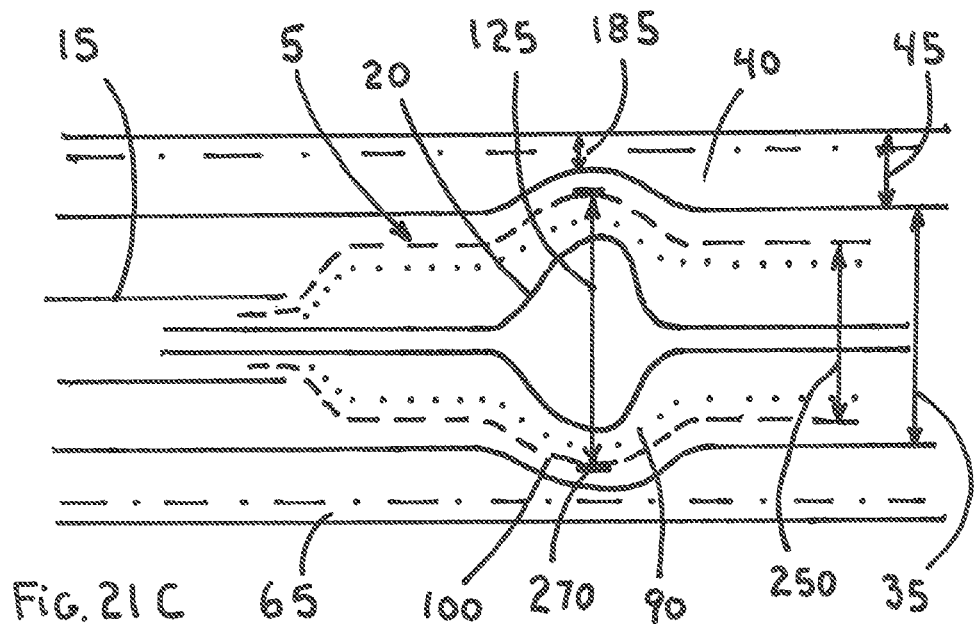
FIG. 21C shows the focal region of a self-expanding compression stent being expanded outwards via a dilation balloon prior to activation of the electrodes on the stent focal region surface.

As shown in FIG. 21C the dilation balloon (20) is inflated to enlarge the stent focal region (100) to a stent focal region diameter (125) that is at least 30% larger than the native vessel diameter (range 30-100% larger) and 30-100% larger than the stent end region diameter (250). Enlargement of the stent focal region (100) to a stent focal region diameter (125) of 80% larger than the native arterial diameter (i.e., an expansion ratio of 1.8, which is equal to stent focal region diameter (125)/normal vessel luminal diameter) will ensure that collagen fibers located in the adventitial layer (65) are aligned and will not stretch further; thus an enlargement of at least 50% (range 50%-100%) will result in compression of the nerve (70) fibers located in the arterial wall and result in nerve block. With the dilation balloon (20) inflated and the arterial wall compressed to a compressed wall thickness (185), application of RF energy is then applied to the arterial wall thereby consistently ablating the nerves (70). The dilation balloon (20) is protected from possible damage from the RF energy (or other forms of energy) due to the presence of the covering (90) that is located between the dilation balloon (20) and the RF electrodes. Consistency of ablation is obtained due to the thinner compressed wall thickness (185) in comparison to a native vessel wall thickness (45); the thinner compressed vessel wall thickness will provide for removal of any blood located in the vasa vasorum or blood pools or blood thermal sinks located in the vessel wall (40), and will reduce the distance for electrical and thermal conduction and transmission of the RF energy (or other forms of energy) through the vessel wall (40).

Figure 21D:
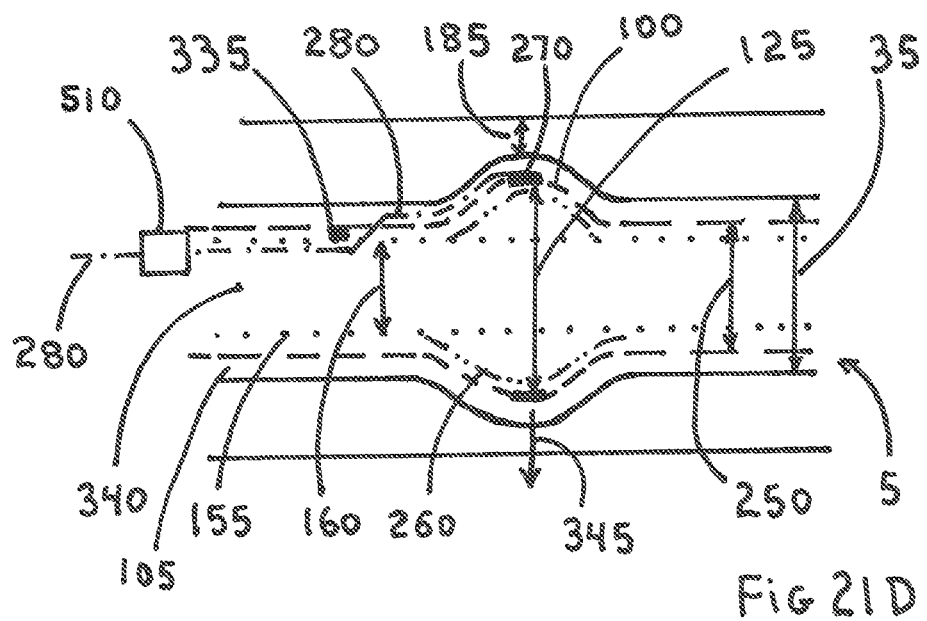
FIG. 21D is a plan view of a compression stent that has been released into the blood vessel and the electrodes located in the stent focal region being activated after the stent focal region has been dilated.

A luminal covering (155) is attached to the compression stent (5) proximal region and stent distal region (110) via a covering-stent attachment (335) as shown in FIG. 21D; the luminal covering (155) can be attached to the stent frame along the length of the stent proximal region (105) and stent distal region (110). The stent luminal covering (155) extends throughout the entire focal region; the stent luminal covering (155) extends through at least a portion of the stent proximal region (105) and stent distal region (110). The covering-stent attachment (335) can be formed by a thermal bond, chemical bond, encapsulation processing, adhesive bond, or other methods of attachment. The stent luminal covering (155) ensures that smooth muscle cell (SMC) hyperplasia does not extend into the vessel lumen (30) and cause luminal stenosis. The luminal covering (155) in the stent focal region (100) is not attached to the stent focal region (100) of this embodiment; the luminal covering (155) in the stent focal region (100) is able to resiliently return to a luminal covering equilibrium diameter (160) that is equal to the native lumen diameter (35) and has a uniform covering diameter throughout the length of the compression stent (5) following vessel wall treatment and removal of the dilation balloon (20). The isodiametric luminal covering (155) serves to prevent thrombosis by providing uniform blood flow through the isodiametric lumen (340) and prevent cellular intrusion into the vessel lumen (30) that can cause vessel stenosis. The stent focal region (100) in this embodiment retains an enlarged stent focal region diameter (125) (range of up to 100% enlargement of a stent end region diameter (250)) and continues to apply an outward force (345) onto the vessel wall (40) until it has attained its stent focal region equilibrium diameter which is within the range of 30-100% enlargement of the native vessel diameter.

As shown in FIG. 21D, a focal covering can be attached to the stent focal region of the compression stent (5) in any of the embodiments if desired to inhibit migration of the stent focal region (100) through the vessel wall (40). Also shown in FIG. 21D is an electromagnetic coupler (510) that is in electrical continuity with the stent electrode (270). The electromagnetic coupler (510) is fixedly attached to the compression stent including positioning it on the surface of the stent proximal region (105). The electromagnetic coupler includes a coil that is able to receive an electromagnetic signal and electromagnetic energy from an external electromagnetic energy generator located outside of the body. A coil located in the energy generator is able to couple with the coil located in the electromagnetic coupler (510) to provide ablative energy to the electrodes at a time period of days, weeks, or months following the implantation of the compression stent into the blood vessel. The electromagnetic generator is able to transmit energy wirelessly through the body of the patient to cause the stent electrodes (270) to become heated and cause nerve ablation at a time period that is later than the initial implantation period when the compression stent was implanted. Thus nerve ablation can be readministered at a later time if necessary to ablate nerves that have regained their transmission capability.

It is noted as an alternative embodiment shown in FIG. 21E that the luminal covering (155) can be attached via a covering-stent attachment (335) to the stent focal region (100) if the stent focal region (100) has a stent focal region equilibrium diameter (i.e., the stent focal region has a natural diameter that it is equal to the stent end region diameter (250)) that is equal to the native vessel lumen diameter (35). In this embodiment the stent is delivered within a small (i.e., 6-12 French) external sheath (15) and is released to form an isodiametric tubular shape or isodiametric lumen (340) that is similar in diameter or up to 15% larger than the native vessel diameter. The stent proximal region diameter (115) and stent distal region diameter (120) do not extend the diameter of the native vessel lumen (30) but are intended to be equal in diameter to the native lumen diameter (35). Upon expansion via the dilation balloon (20) the stent focal region (100) as shown in FIG. 21C must be able to expand to a stent focal region diameter (125) at least 30% larger (range 30-100% larger) than the native vessel lumen diameter (35) and 30-100% larger than the stent end region diameter (250). For the case of fully expanding the collagen fibers located in the adventitial layer (65), it is necessary to expand the stent focal region (100) to a stent focal region diameter (125) 80% larger (range 50-100% larger) than the native vessel lumen diameter (35) and 80% larger (range 50-100% larger) than the stent end region diameter (250). An expansion of the stent focal region to 50% larger than the native vessel lumen would provide significant thinning of the vessel wall to create an improved ablation of the renal nerves than found in normal renal nerve ablation procedures without application of compression to the vessel wall. The stent focal region (100) must then be able to retract back to a stent focal region diameter (125) that is equal to the native arterial diameter after the deflated dilation balloon has been removed as shown in FIG. 21E.

It is further noted for the embodiments shown in FIGS. 21A-21E the electrical connection from the stent electrode (270) to the RF generator (320) can be made via a stent conduction wire (280) that forms an electrical interface with the external sheath (15) instead of with the pusher that is shown in FIG. 21E. For this embodiment (see FIG. 21F) a sheath-wire interface (350) can be located at or near the distal end of the external sheath (15) as shown in FIG. 21F. Electrical contact can be made by the stent conduction wire (280) and the sheath-wire interface (350) wherein the compression stent (5) is only partially released (see FIG. 21F) from the external sheath (15) and prior to complete release of the compression stent (5) from the external sheath (15). The RF energy is transmitted from the RF generator (320) to the sheath-wire interface (350) via a sheath conduction wire (355) located in the wall of the external sheath (15). The compression stent (5) in this embodiment would only be completely released from the external sheath (15) after the RF energy had been delivered to the stent electrode (270). Other electrode connections are anticipated that can be made between the stent electrodes (270) and the various components located within the delivery sheath including the pusher, for example.

Figure 22A:
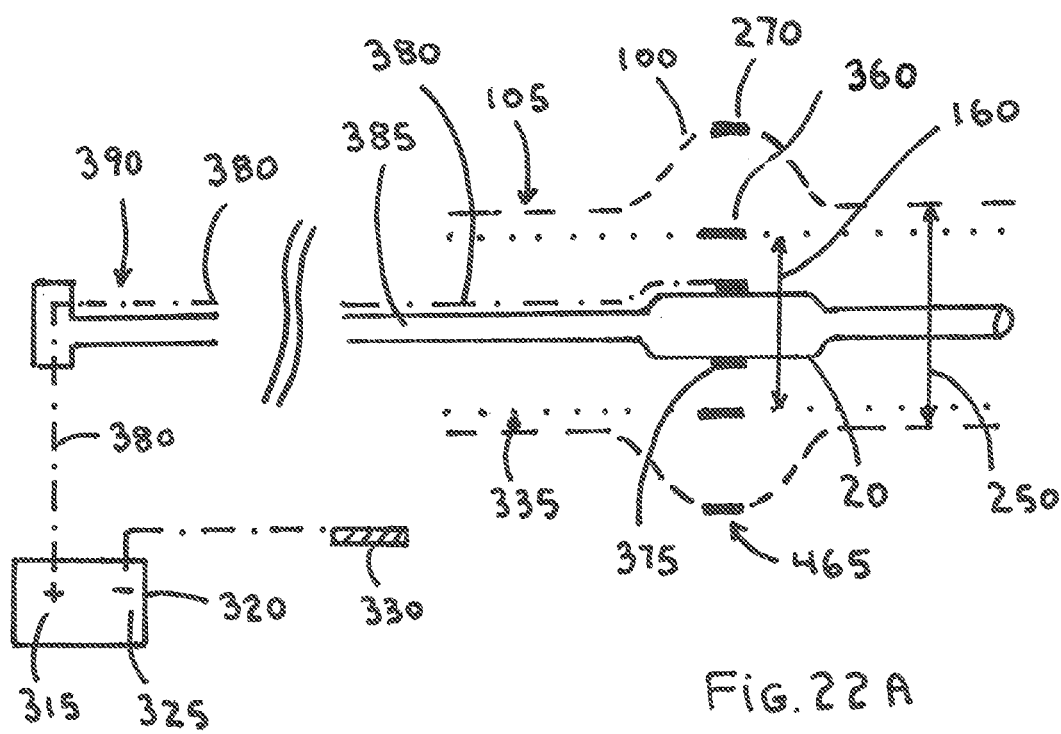
FIG. 22A is a plan view of a self-expanding compression stent that has electrodes located in the stent focal region and the electrodes receiving their energy via a radiofrequency generator that delivers its energy via a conduction wire located in the dilation catheter shaft.
Figure 22B:
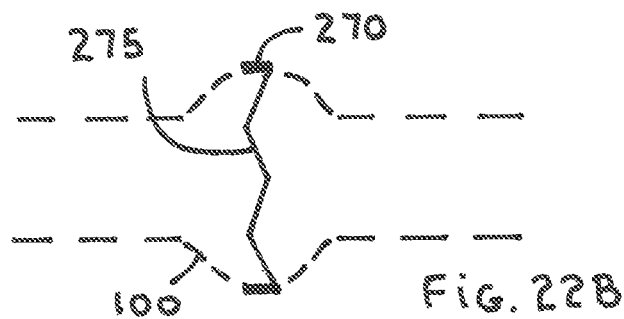
FIG. 22B is a plan view of an expandable stent electrode in an expanded configuration; the electrode forms a portion of the stent focal region.
Figure 22C:
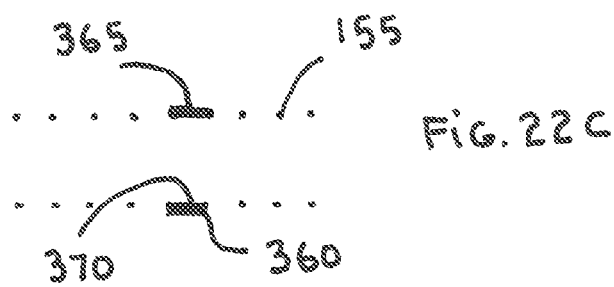
FIG. 22C is a plan view of the compression stent electrode and covering in an equilibrium configuration following expansion that returns to a diameter that matches the diameter of the native blood vessel.

An alternate embodiment for the self-expanding compression stent (5) having RF energy, for example, (or other energy) delivery capability while the arterial wall is being compressed is shown in FIGS. 22A-22E. FIG. 22A shows the compression stent (15) in an expanded equilibrium configuration in free space. The compression stent (5) has a stent electrode (270) positioned around a perimeter of the stent focal region (100). The stent electrode (270) can be a zig-zag stent element (275) of the stent focal region (100) as shown in FIG. 22B. The stent electrode (270) is formed from a metal that is able to conduct electrical current; a thin coating of a platinum metal onto a SE stent element can serve as a stent electrode (270), for example. A luminal covering (155) is attached via a covering-stent attachment (335) to stent proximal region (105) and stent distal region (110); the luminal covering (155) extends throughout the entire stent focal region (100). The luminal covering equilibrium diameter (160) of the luminal covering (155) in the stent focal region (100) is equal to the native lumen diameter (35) and equal to the stent end region diameter (250). The luminal covering (155) in the stent focal region (100) has a covering electrode (360) attached to it as shown in FIG. 22C; the covering electrode (360) provides electrical continuity across the wall of the stent luminal covering (155) in the stent focal region (100). This electrical continuity can be formed by providing an outer stent-covering surface (365) of the covering electrode (360) that faces toward the stent electrode (270) and providing an inner covering-balloon surface (370) of the covering electrode (360) that faces toward the dilation balloon (20). The dilation balloon (20) has a balloon electrode (375) located on the dilation balloon (20); the balloon electrode (375) is connected via balloon conduction wire (380) which extends along the balloon catheter shaft (385) to the proximal end (390) of the catheter shaft where it connects to a first pole (315) of an RF generator (320) (or other energy generator such as a microwave generator, for example. The opposing pole (325) of the RF generator (320) is electrically connected to an opposing electrode located on the patient's skin, such as located on the patient's back, for example.

The compression stent (5) of this embodiment is delivered to the renal artery vessel lumen (30) contained within an external sheath (15) and loaded onto a dilation balloon (20) with the stent focal region (100) adjacent the balloon focal region (135) as described in the embodiment of FIGS. 20A-20D. The compression stent (5) is shown in an expanded configuration in FIG. 22D with the dilation balloon (20) dilated. The arterial vessel wall (40) has formed a compressed wall thickness (185) from the compression stent (5) due to the expansion of the dilation balloon (20). With the compression stent (5) in an expanded configuration RF energy is transmitted via the conduction wire to the balloon electrode (375) which conveys the electrical energy via contact with the balloon-covering surface through the covering electrode (360) to the stent-covering surface that makes electrical contact with the stent electrode (270) to convey electrical energy into the vessel wall tissue to cause thermal, compressive, and other ablation for the renal nerves (70). For a unipolar RF electrode, the energy is transmitted through the body tissues to an opposing electrode located on the patient's skin surface. The nerves (70) located in the vessel wall (40) will be ablated more consistently due to the compression of the vessel wall (40) as the ablative energy is being transmitted than if the vessel wall (40) had a larger native vessel wall thickness (45).

Following ablation of the nerves (70) located in the arterial wall, the dilation balloon (20) can be deflated and removed from the body. The compression stent (5) can remain at a stent focal region diameter (125) that is 30-100% larger than the native artery lumen diameter (35) as shown in FIG. 22E and 30-100% larger than the stent end region diameter (250). The luminal covering (155) located in the stent focal region (100) will resiliently return to a diameter that is equal to the native lumen diameter (35) and equal to the proximal region equilibrium diameter (115) and stent distal region diameter (120) (herein also referred to as the stent end region diameter (250)). The isodiametric lumen (340) of the final compression stent lumen (395) will ensure that thrombosis does not occur; the luminal covering (155) will prevent cellular infiltration into the vessel lumen (30) resulting in vessel stenosis.

Figure 22D:
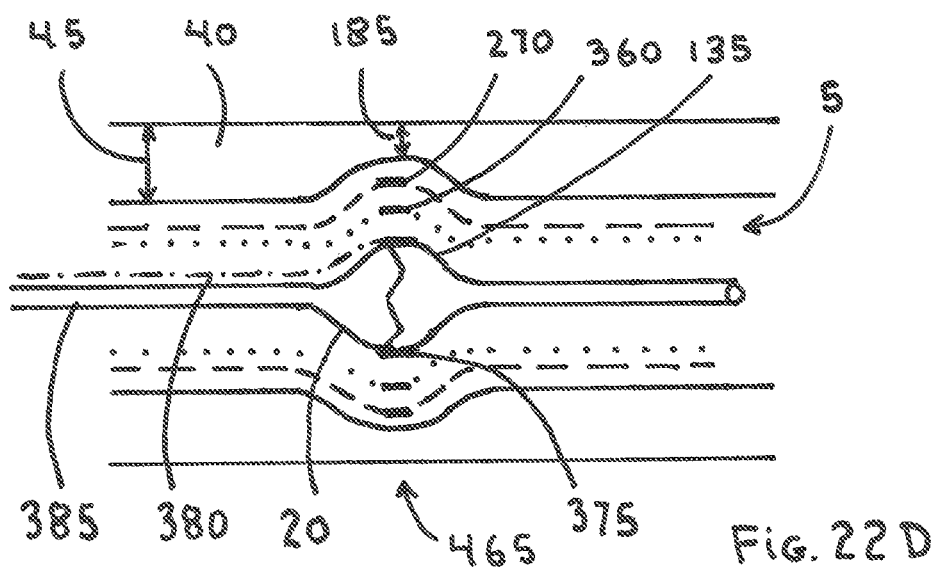
FIG. 22D is a plan view of a self-expanding compression stent in an expanded configuration via inflation of the dilation balloon than delivers the radiofrequency energy from the radiofrequency generator; the vessel wall has become thinned allowing radiofrequency energy to ablate the nerves more consistently.

In an alternate embodiment, the device as shown in FIG. 22D with the dilation balloon (20) inflated could have a focal region equilibrium diameter that is the same diameter as the stent proximal region diameter (115) and stent distal region diameter when the dilation balloon (20) is deflated and removed as shown in FIG. 22F. In this embodiment, the luminal covering (155) in the stent focal region (100) can be attached via a stent-covering attachment to the compression stent (5) in the stent focal region (100). Following expansion of the stent focal region (100) by the dilation balloon (20), both the stent focal region (100) and the luminal covering (155) attached to the stent focal region (100) will return to a stent focal region diameter (125) that is equal to the stent end region diameter (250).

The stent electrode (270) described in the embodiments of FIGS. 21A-21E and 22A-22E can be bipolar electrodes (398) rather than unipolar electrodes (465). The stent bipolar electrodes (398) are shown in FIG. 23A. The bipolar electrodes can be formed from two zig-zag stent elements (275), for example, that form a portion of the stent focal region (100).

In one embodiment two separate conduction wires, a first conduction wire (400) and a second conduction wire (405) that are electrically insulated from each other are connected to a first stent electrode (410) and a second stent electrode (415), respectively, as shown in FIG. 23B. Each conduction wire extends separately to the pusher member (255) and follows a separate conduction wire to the proximal end (390) of the external sheath (15) as described in the embodiment of FIGS. 21A-21D. A first conduction wire (400) connects to a first pole (315) (or positive pole) of the RF generator (320), and a second conduction wire (405) connects to a second pole (or negative pole) of the RF generator (320). Activation of the bipolar electrodes (398) via a signal from the RF generator (320) results in current from the first stent electrode (410) through the tissues of the vessel wall (40) to the second stent electrode (415). Heating of the tissues of the vessel wall (40) and the nerves (70) will result in ablation of renal nerve conduction.

In an alternate embodiment, the bipolar stent electrodes (398) described in FIG. 23A can receive its RF energy signal from bipolar balloon electrodes (495) located on the dilation balloon (20) as shown in FIG. 23C. The bipolar balloon electrodes (495) would each have a separate conduction wire that is insulated and extending from one bipolar balloon electrode (495) to the proximal end (390) of the dilation catheter. Each bipolar balloon electrode (495) would be connected to a separate pole of an RF generator (320); the first balloon electrode (420) would connect via a first conduction wire (400) to the first pole (315) of the RF generation and the second balloon electrode (425) would connect via a second conduction wire (405) to a second pole of the RF generator (320), for example. As described for the embodiment of FIGS. 22A-22E for the unipolar stent electrode (465), the bipolar signal would be transmitted from the RF generator (320) to the first balloon electrode (420) and second balloon electrode (425) and then transmitted separately and insulated from each other through two separate covering electrodes (360) to the two separate stent electrodes (270), a first stent electrode (410) and a second stent electrode (415), respectively. The bipolar electrical RF signal is delivered via the two stent bipolar electrodes (398) to the tissues of the vessel wall (40) which is heated thermally and causes the renal nerves (70) to become ablated due to thermal trauma at temperatures greater than 47 degrees C. It is understood that more than two bipolar electrodes (398) can be located on the dilation balloon (20) and more than two bipolar stent electrodes (can be located in the stent focal region (100). Thus multiple pairs of bipolar stent electrodes (each bipolar electrode pair (480) (shown in FIG. 23F) being a positive and a negative electrode, i.e., stent electrodes attached to a positive and negative poles of the RF generator (320)) placed on the outer surface of the compression stent (5) in the stent focal region (100) can deliver RF energy to the vessel wall tissues at multiple locations around the perimeter of the arterial wall.

Electrodes such as stent electrodes (270) can be placed directly on the compression stent (5) as shown in FIGS. 21A-21E and 23A and 23B; electrodes can be located also on the covering (such as covering electrodes (360)) and on the dilation balloon (20) (such as balloon electrodes (375))

as shown in FIGS. 22A-22F and 23C. Furthermore it has been described that the electrodes can be unipolar electrodes (465) as shown in FIGS. 21A-21E and 22A-22F or they can be bipolar electrodes (398) as shown in FIGS. 23A-23C. Other configuration for the electrodes have been contemplated and are herein further described as configured onto the compression stent (5), but it is understood that similar electrode configurations can also be configured onto a dilation balloon (20) and an electrical signal (or other energy signal) can then be transmitted either directly to the surrounding arterial wall or transmitted from the balloon and through the covering (90) to the stent to the artery wall to cause ablation of the nerves (70).

Figure 23E:
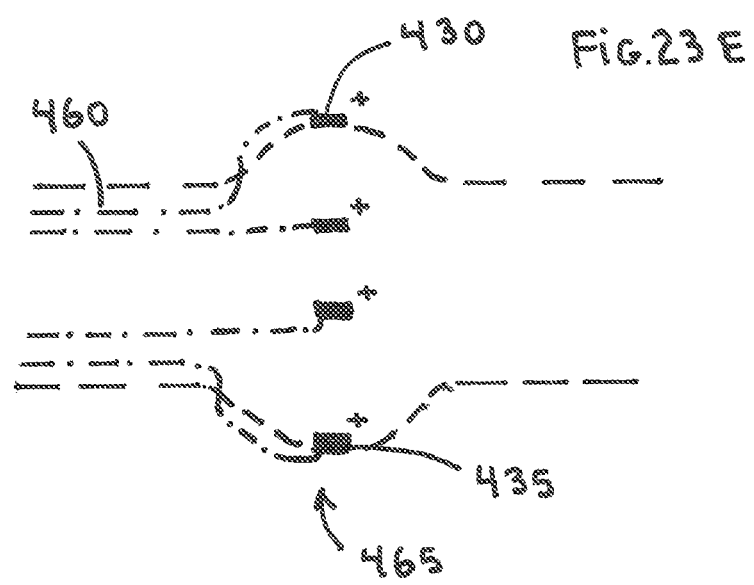
FIG. 23E shows individual conduction wires delivering energy to individual monopolar electrodes.
Figure 23:
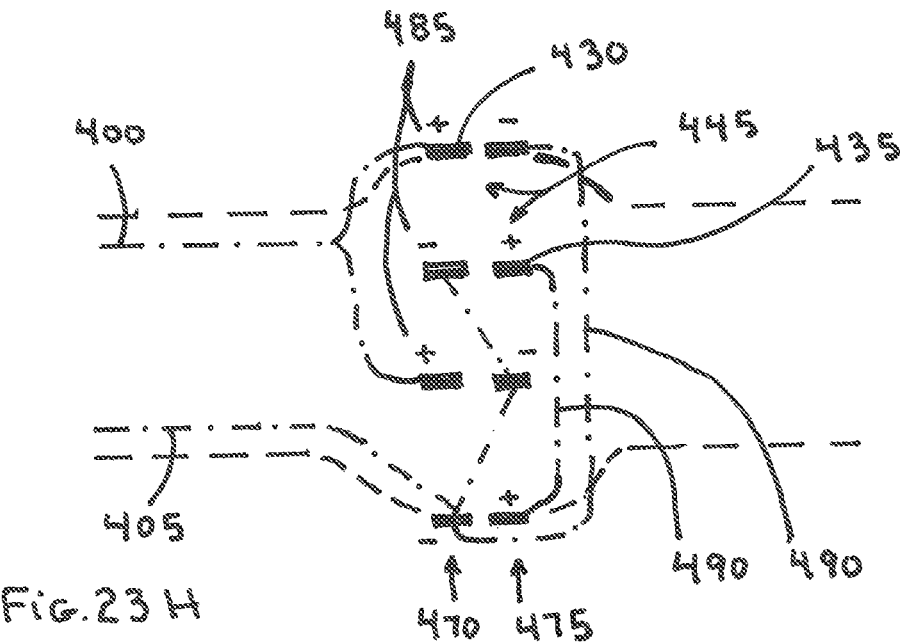
FIG. 23A is a plan view of a compression stent in an expanded configuration having bipolar electrodes located in the focal region of the stent.
FIG. 23B is a plan view of the compression stent with bipolar electrodes being released from a delivery sheath and expanding outwards to an expanded configuration.
FIG. 23F is a plan view of a bipolar electrode configuration having two rows located along the perimeter of the surface of the stent focal region.
FIG. 23G is a plan view of a bipolar electrode configuration having a single row of electrodes along a perimeter of the stent focal region.
FIG. 23H is a plan view of a configuration of bipolar electrodes located along the perimeter of the stent focal region.
FIG. 23J is a plan view of a configuration of bipolar electrodes having two rows of electrodes with each row having a specific polarity.
Figure 23:
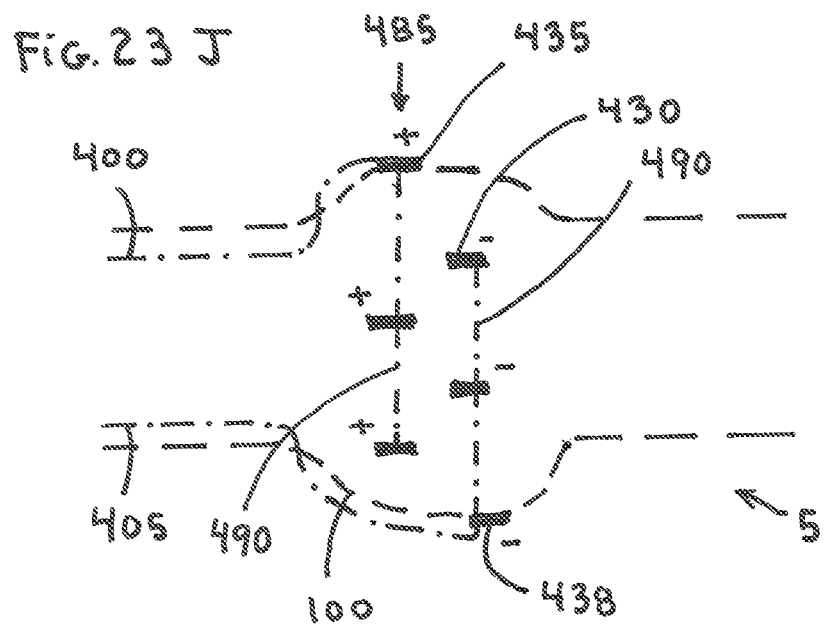

FIG. 23D shows one configuration for the electrodes (i.e., electrode configuration for either the compression stent (5) or the dilation balloon (20)) of the present invention positioned along the perimeter of the stent focal region (100), for example. Individual electrodes (430) of the same polarity such as a positive polarity or positive electrode (435), for example, are positioned along a perimeter of the stent focal region (100). The electrodes can form a circular pattern (440), for example, or they can form a zig-zag pattern (445) as shown in FIG. 23H such that they do not align along a circular path around the perimeter. Locating the electrodes as individual electrodes (430) with a spacing between them can provide for a higher current density at each point than could be obtained with a single ring electrode that can place a lower current density along at least a portion of a ring electrode (where the electrode is a continuous ring extending around the perimeter of the stent focal region (100), for example). Approximately 8 individual electrodes (430) (range 3-16) can be located along the perimeter of stent focal region (100) (or balloon focal region), for example. Also, the current to each of the individual electrodes (430) can be controlled by the RF generator (320) such that the current or energy is more evenly distributed around the entire perimeter of the arterial wall. Each individual electrode can connect to a common conduction wire (450) (such as a stent conduction wire (280), for example) which extends proximally to form electrical continuity with the RF generator (320). Activation of the common conduction wire (450) via the RF generator (320) will cause each of the electrodes located on the stent to become activated at the same time and with a similar amount of energy that is dependent upon the impedance of the surrounding tissue. Local control of the current delivery to each electrode can be accomplished, if desired, using a micro circuit (455) located on the stent or on the covering (90) or on the dilation balloon (20) that controls current delivery to each of the individual electrodes (430) depending upon tissue impedance. Each of the individual electrodes (430) can alternately be connected separately to a separate and electrically insulated singular conduction wire (460) that forms electrical continuity with the RF generator (320) as shown in FIG. 23E. In this case, each electrode on the stent (or on the dilation balloon (20), for example) can be controlled from the RF generator (320) to provide a controlled amount or energy to each electrode to achieve, for example, a specific temperature, specific current delivery, a specific tissue impedance, or other indicative factor to assist in determining that an appropriate amount of energy has been delivered to achieve proper tissue ablation. Temperature, for example, can be measured locally at the site of tissue contact with the electrode using a thermocouple that can be positioned in the stent focal region (100) near or contiguous with the individual electrode. For the unipolar electrodes (465) as shown in FIGS. 23D and 23E, a counter electrode is located on the surface of the patient's body such as the back, abdomen, or other appropriate area as discussed earlier.

Another configuration for the bipolar electrodes (398) is shown in FIG. 23F having two separate electrode rows (485) of individual electrodes (430) that extend along the perimeter of the stent focal region (100); one row being separated in an axial direction (505) from another electrode row (485). The first electrode row (470) is comprised of individual electrodes (430) of one polarity, positive, for example. Each electrode is connected to a first conduction wire (400) that forms an electrical continuity back to the positive pole of the RF generator (320) as described previously. The second electrode row (475) is comprised of individual electrodes (430) of another polarity, negative, for example, each individual electrode is connected to a second conduction wire (405) that forms an electrical continuity back to the negative pole of the RF generator (320) as described previously; thus this embodiment describes bipolar electrodes (398). Activation of the bipolar electrodes (398) generates a conduction from a positive individual electrode to one or more negative individual electrodes (430) causing current to flow through the tissue and generating heat within the tissue. The control of the amount of current and energy delivered to the vessel wall (40) is accomplished at the RF generator (320); temperature can be monitored at the electrode site by a thermocouple, for example that is located on the compression stent (5), covering (90), or dilation balloon (20) and is electrically connected to the RF generator (320) to assist in controlling the energy output at an appropriate level to achieve ablation. As discussed for the configuration shown in FIG. 23D, each individual electrode of the embodiment of FIG. 23F can alternately be connected to the RF generator (320) via a singular conduction wire (460) that follows an insulated conduction path, if desired to provide individual control to each bipolar electrode pair (480) of electrodes that are in proximity or neighboring another electrode of an opposite polarity. Each individual electrode of this embodiment would be electrically insulated from other electrodes such that each electrode could be controlled separately by the RF generator (320).

Another configuration for a bipolar electrodes (398) is shown in FIG. 23G having a single electrode row (485) of individual electrodes (430) extending along a perimeter but having the electrodes alternate in their polarity such that a positive electrode (435) is located between two negative electrodes (438) and a negative electrode (438) is located between two positive electrodes (435). The positive electrodes (435) can be connected to a first conduction wire (400) that forms an electrical continuity with a positive pole, for example, of the RF generator (320). The negative electrodes (438) can be connected to a second conduction wire (405) that forms an electrical continuity with a negative pole, for example, of the RF generator (320). An insulated jump wire (490) can be used to provide electrical continuity between individual electrodes (430) of a similar polarity. Activation of the electrodes via the RF generator (320) produces a ring of energy delivery along the perimeter of the arterial wall causing ablation of the nerves (70) found in the vessel wall (40). If desired, each positive electrode (435) and each negative electrode can be provided a separate insulated singular conduction wire (460) (as discussed in prior embodiments of the present invention) that forms electrical continuity between each electrode and the RF generator (320) to provide individual monitoring of current delivery, and tissue resistance or impedance that will direct the operator regarding tissue ablation and knowledge of whether the treatment has been completed in a particular area of tissue located along the perimeter of the arterial wall.

FIG. 23H shows another configuration for the bipolar electrodes (398) that has two electrode rows (485) of individual electrodes (430) and each electrode row (485) has alternating polarity of the neighboring electrode along the perimeter. The pattern of positive individual electrodes (430) along the perimeter of the compression stent (5) follows a zig-zag pattern (445). A first conduction wire (400) can make electrical connection with each of the positive electrodes (435), for example. Alternately a first conduction wire (400) can make a connection with one positive electrode (435) and a positive jump wire (490), for example, or other conduction path can be used to form an electrical connection between one positive electrodes (435) and a second positive electrode (435). A second conduction wire (405) can similarly make electrical continuity with the negative electrodes (438), for example. Having two rows of alternating positive and negative electrodes (438) provides a very uniform and continuous ablation of tissues along a perimeter of the vessel wall (40). As discussed for the previous configurations, singular conduction wires (460) can form electrically insulated conduction path to the RF generator (320) to provide improved control of energy delivery to a specific individual electrodes (430) as indicated by the current delivery, and impedance measurements obtained by the RF generator (320) or via micro circuitry (455) located on the stent.

Another configuration for the bipolar electrodes (398) that has two electrode rows (485) and each electrode row (485) has alternating polarity of the neighboring individual electrodes (430) along the perimeter is shown in FIG. 23J. This configuration is similar to that shown in FIG. 23H except that the electrodes found in the first electrode row (470) are staggered from the individual electrodes (430) found in the second electrode row (475). Each individual electrode of a specific polarity can be connected to another electrode of similar polarity via a jump wire (490), for example. The configuration of 23J provides a current flow through the vessel wall (40) that extends with both a circumferential direction and an axial direction to provide a longer path for the current and a greater volume amount of ablated tissue and less likely chance that a physical entity located in the vessel wall (40) can obstruct or act as a heat sink to block or disrupt the ablation around the perimeter of the artery.

Other configurations for the electrodes located on the stent or located on a dilation balloon (20) are contemplated. The configurations presented in this patent application are not intended to limit the scope of possible electrode configurations.

The two bipolar electrodes (398) located on the stent focal region (100) can furthermore be used to determine if the treatment used to block the renal nerve signal was successful. A separate signal can be sent to a first stent electrode (410) via a first conduction wire (400) and detection can be performed at the second stent electrode (415) (via the second conduction wire (405)) to determine if the sent signal is able to be transmitted via renal nerves (70) to the second electrode. By comparing the ability to detect such a signal prior to performing the ablative therapy (such as the RF ablation therapy) and after performing the ablation therapy, a determination can be made if the renal nerves (70) have been successfully ablated. This determination can be made following an ablation delivery in order to identify if the RF therapy, for example, is complete and if it has been successful.

Figure 24A:
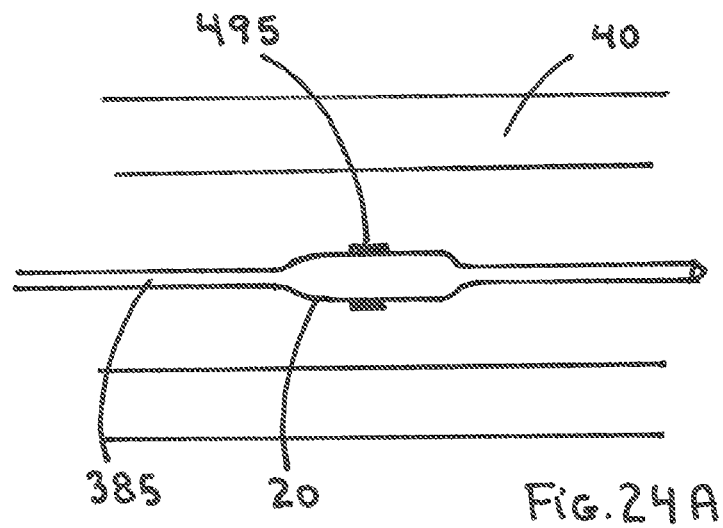
FIG. 24A is a plan view of a dilation balloon having a monopolar or bipolar electrode located on the surface of the balloon focal region.
Figure 24B:
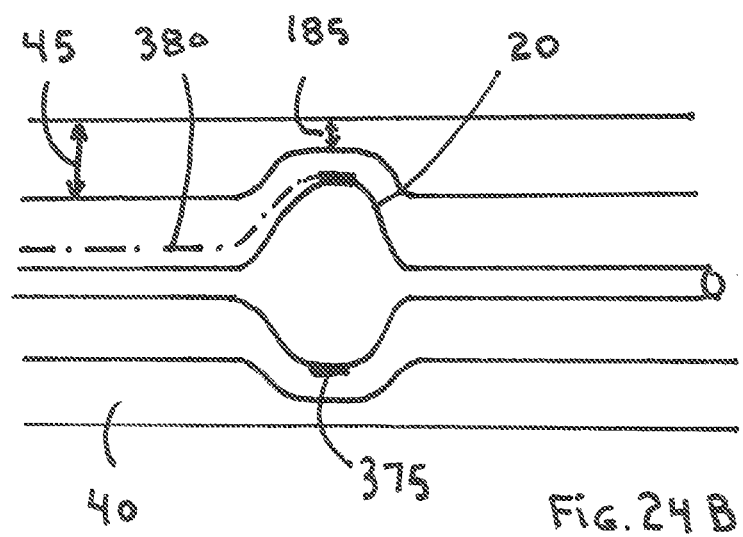
FIG. 24B is a plan view of a conduction wire providing radiofrequency energy to the electrode located on the balloon focal region in an expanded configuration within a native blood vessel and ready for delivery of the radiofrequency energy.

Another further embodiment for a system for providing RF ablation to an arterial vessel wall (40) is shown in FIG. 24A-24D. A dilation balloon (20) having a unipolar balloon electrode (375) or bipolar balloon electrodes (495) located on the outer surface of the dilation balloon (20) is entered into the renal artery and located at the site to perform the ablation of the nerves (70) located in the vessel wall (40) (see FIG. 24A). The balloon is dilated from 30-100% of the native vessel diameter to compress the native arterial wall from a native vessel wall thickness (45) to a compressed vessel wall thickness (185) as shown in FIG. 24B. While the balloon is dilated, RF energy, microwave energy, thermal energy or ultrasound energy is applied via the balloon conduction wire (380) to the balloon electrode (375 and 495); alternately, chemical ablative materials are injected into the vessel wall (40). The dilation balloon (20) is then deflated (FIG. 24C) and the balloon catheter is then removed from the body. A covered stent (500) with a covering (90) attached through at least a portion of its length is then delivered across the location of the ablation as shown in FIG. 24D; the covered stent (500) extends at least 3 mm on each side of the ablation region; the covering (90) ensures that cellular proliferation and migration into the vessel lumen (30) is prevented and to ensure that thrombosis does not initiate vessel occlusion or stenosis.

Reference numerals used to describe structural elements of one embodiment are intended to be applied to another embodiments to describe the same structural element and have the same description for all similar structural elements. Other embodiments of the present invention are anticipated and the presented embodiments are not intended to limit the scope of the invention.

The invention claimed is:

1. A method for ablating nerves located in a wall of a tubular member of a body, the tubular member having an unexpanded tubular member diameter in a native state, the method comprising the sequential steps,
    A. delivering an implantable device comprising a stent configured for transcatheter delivery within the body to a location within the tubular member radially adjacent to the nerves being ablated, said stent comprising,
        i. a stent delivery configuration during said delivery step,
        ii. a stent first region having a stent first region delivery diameter,
        iii. said stent first region having one or more electrodes being permanently affixed to said stent first region, and
        iv. a stent second region located axially adjacent to said stent first region, said stent second region not having any of said one or more electrodes affixed thereto,
    B. expanding said stent from said stent delivery configuration to a stent expanded configuration, said stent first region being expanded outwards from said stent first region delivery diameter to a stent first region expanded diameter configured to enlarge the unexpanded tubular member diameter by at least 30% and placing said one or more electrodes closer to the nerves than if the tubular member were not enlarged by said stent,
    C. receiving ablative energy by said one or more electrodes with said stent first region having said first region expanded diameter to ablate the nerves located in the wall of the tubular member at a distance closer to said one or more electrodes than from a vessel wall luminal surface in the native state, and
    D. implanting said stent within the tubular member.

2. The method of claim 1 wherein said stent is configured to self-expand and said device further comprising an external sheath positioned around said stent to hold said stent in said stent delivery configuration, said expanding step further comprising removing said external sheath from around said stent to allow said stent first region to expand to said stent first region expanded diameter.

3. The method of claim 2 wherein said stent has a covering attached to said stent second region, said stent second region having a stent second region diameter in said stent expanded configuration equal to the unexpanded tubular member diameter, said covering preventing a flow of blood radially through a wall of said stent and preventing migration of cells onto said stent after implant, said covering being unattached to said first stent region such that said covering has a covering diameter extending throughout said covering that is equal to the unexpanded tubular member diameter during said implanting step.

4. The method of claim 2 wherein said stent has a covering attached to said stent first region, said covering having a covering diameter extending therethrough equal to said stent first region expanded diameter during said implanting step.

5. The method of claim 1 wherein said device further comprises a dilation balloon located at the end of a balloon dilation catheter, wherein during said delivering step and said expanding step, said stent first region is positioned over said dilation balloon.

6. The method of claim 5 wherein said stent is configured to be balloon expandable, said expanding step comprising inflating said dilation balloon to expand said stent first region to said stent first region expanded diameter at least 30% larger than the unexpanded tubular diameter, said implanting step comprising implanting said stent with said stent first region at least 30% larger than the unexpanded tubular member diameter.

7. The method of claim 6 wherein said stent has a covering attached to said stent first region, said covering preventing blood flow radially through a wall of said stent and preventing cell migration onto said stent after implant, said covering being permanently attached to said first stent region and having a covering diameter equal to the stent first region expanded diameter during said implanting step.

8. The method of claim 6 wherein said stent has a covering attached to said stent second region having a stent second region diameter equal to the unexpanded tubular member diameter after said expanding step, said covering being unattached to said first stent region and having an elastic character such that said covering has a covering diameter after said expanding step extending throughout said covering and being equal to the unexpanded tubular member diameter during said implanting step.

9. The method of claim 5 wherein said stent is configured to self-expand, and
said device further comprising an external sheath positioned over said stent to hold said stent in said stent delivery configuration during said delivering step, said expanding step further comprising, i. removing said external sheath, before expanding said stent from said stent delivery configuration to said stent expanded configuration, and ii. inflating said dilation balloon to expand said stent first region outwards to said stent first region expanded diameter.

10. The method of claim 9 wherein said implanting step includes implanting said stent in said stent first region expanded configuration.

11. The method of claim 10 wherein said stent first region has a covering permanently attached to said stent first region, said covering preventing blood flow radially across a wall of said stent and preventing cell migration onto said stent after implant, said covering having a first region covering diameter equal to said stent first region expanded diameter during the implanting step.

12. The method of claim 10 wherein said stent has a covering attached to said stent second region, said stent second region having a stent second region diameter equal to the unexpanded tubular member diameter during said expanding step, said covering being unattached to said first stent region and having an elastic character such that said covering has a covering diameter extending therethrough and equal to the unexpanded tubular member diameter during said implanting step.

13. The method of claim 9 wherein following said expanding step, and following said receiving ablative energy step, and prior to said implanting step said stent first region returns to a stent first region implanted diameter equal to the unexpanded tubular member diameter for implant during said implanting step.

14. The method of claim 9 wherein said stent has a covering attached to said stent first region, said covering having an elastic character such that said covering diameter reduces to a covering diameter equal to the unexpanded tubular member diameter prior to said implanting step.

15. The method of claim 1 wherein the step of receiving ablative energy includes receiving radiofrequency energy by said one or more electrodes.

16. The method of claim 1 wherein said one or more electrodes are a unipolar electrodes, said device further comprising a counter electrode in addition to said one or more electrodes, said counter electrode configured to be placed along an external location in contact with the body.

17. The method of claim 1 wherein said one or more electrodes are unipolar or bipolar electrodes comprising a negative electrode and a positive electrode.

18. The method of claim 1 wherein said one or more electrodes receive the ablative energy via wireless transmission via electromagnetic coupling.

19. The method of claim 18 wherein the step of receiving ablative energy by said one or more electrodes occurs at a time period of hours, days, or weeks after said implanting step of said device into the tubular member of the body.

20. The method of claim 1 wherein said ablative energy is provided to said one or more electrodes via an electrical conduction wire located in a delivery catheter, said electrical conduction wire being uncoupled from said one or more electrodes during said implanting step.

* * * * *